US010961299B2

(12) United States Patent
Feng et al.

(10) Patent No.: US 10,961,299 B2
(45) Date of Patent: Mar. 30, 2021

(54) **TETRA-SPECIFIC, OCTAMERIC BINDING AGENTS AND ANTIBODIES AGAINST *CLOSTRIDIUM DIFFICILE* TOXIN A AND TOXIN B FOR TREATMENT OF *C. DIFFICILE* INFECTION**

(71) Applicants: Hanping Feng, Ellicott City, MD (US); Yongjun Guan, Clarksville, MD (US); Yongrong Zhang, Columbia, MD (US); Zhiyong Yang, Ellicott City, MD (US); Lianfa Shi, Baltimore, MD (US)

(72) Inventors: Hanping Feng, Ellicott City, MD (US); Yongjun Guan, Clarksville, MD (US); Yongrong Zhang, Columbia, MD (US); Zhiyong Yang, Ellicott City, MD (US); Lianfa Shi, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/548,901

(22) PCT Filed: Feb. 5, 2016

(86) PCT No.: PCT/US2016/016852
§ 371 (c)(1),
(2) Date: Aug. 4, 2017

(87) PCT Pub. No.: WO2016/127104
PCT Pub. Date: Aug. 11, 2016

(65) Prior Publication Data
US 2018/0244760 A1    Aug. 30, 2018

Related U.S. Application Data

(60) Provisional application No. 62/113,046, filed on Feb. 6, 2015.

(51) Int. Cl.
*C07K 16/12* (2006.01)
*A61P 31/04* (2006.01)
*A61K 39/00* (2006.01)

(52) U.S. Cl.
CPC .......... *C07K 16/1282* (2013.01); *A61P 31/04* (2018.01); *A61K 2039/505* (2013.01); *C07K 2317/24* (2013.01); *C07K 2317/30* (2013.01); *C07K 2317/31* (2013.01); *C07K 2317/35* (2013.01); *C07K 2317/52* (2013.01); *C07K 2317/524* (2013.01); *C07K 2317/526* (2013.01); *C07K 2317/569* (2013.01); *C07K 2317/60* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| 2010/0056439 | A1 | 3/2010 | Beckmann et al. |
| 2013/0058962 | A1 | 3/2013 | Shoemaker et al. |
| 2014/0242080 | A1 | 8/2014 | Jaeger et al. |
| 2014/0294826 | A1 | 10/2014 | Shoemaker |

FOREIGN PATENT DOCUMENTS

| WO | 2009/032782 | 3/2009 |
| WO | 2011/107507 | 9/2011 |
| WO | 2014/151910 | 9/2014 |
| WO | 2017/066468 | 4/2017 |

OTHER PUBLICATIONS

Exons, Introns, Codons & their Equivalents. 2019 by Steven M. Carr. Retrieved Mar. 31, 2020 at https://www.mun.ca/biology/scarr/Exons_Introns_Codons.html.*
International Search Report and Written Opinion of the International Searching Authority, dated Aug. 16, 2016 in corresponding International Application No. PCT/US16/16852.
Extended European Search Report dated Jun. 26, 2018 in European Application No. 16747370.1.
Conrath et al., "Camel Single-domain Antibodies as Modular Building Units in Bispecific and Bivalent Antibody Constructs", The Journal of Biological Chemistry, 276(10):7346-7350 (2001).
Yang et al., "A Novel Multivalent, Single-Domain Antibody Targeting TcdA and TcdB Prevents Fulminant *Clostridium difficile* Infection in Mice", Journal of Infectious Diseases, 210(6):964-972 (2014).
Spiess et al., "Alternative molecular formats and therapeutic applications for bispecific antibodies", Molecular Immunology, 67(2):95-106 (2015).
Andersen et al., "Neutralization of *Clostridium difficile* Toxin B Mediated by Engineered Lactobacilli That Produce Single-Domain Antibodies", Infection and Immunity, 84(2):395-406 (2016).
Schmidt et al., "A Tetraspecific VHH-Based Neutralizing Antibody Modifies Disease Outcome in Three Animal Models of *Clostridium difficile*", Clinical and Vaccine Immunology, 23(9):774-784 (2016).
Yang et al., "Intravenous adenovirus expressing a multi-specific, single-domain antibody neutralizing TcdA and TcdB protects mice from *Clostridium difficile* infection", Pathogens and Disease, 74(7):1-8 (2016).

* cited by examiner

*Primary Examiner* — Oluwatosin A Ogunbiyi
(74) *Attorney, Agent, or Firm* — Wenderoth, Lind & Ponack, L.L.P.

(57) ABSTRACT

Novel, antibody-based binding agents derived from human and camelid immunoglobulins are described. These binding agents recognize and bind with specificity to *Clostridium difficile* toxin A and/or toxin B and in some cases exhibit toxin neutralizing activity. These binding agents can be used to treat or prevent primary and recurrent CDI. The binding agents include camelid $V_HH$ peptide monomers, linked groups of $V_HH$ peptide monomers, $V_HH$ peptide monomers joined to antibody Fc domains, and $V_HH$ peptide monomers joined to IgG antibodies.

12 Claims, 14 Drawing Sheets
Specification includes a Sequence Listing.

Figure 11A

Habab binds to TxA

Figure 11B

Habab binds to TxB

Figure 12A

Coat TcdA to detect TcdB

- TcdB=1000ng/ml
- TcdB=200ng/ml
- TcdB=40ng/ml
- TcdB=8ng/ml
- TcdB=1.6ng/ml

Figure 12B

Coat TcdB to detect TcdA

- TcdA=1000ng/ml
- TcdA=200ng/ml
- TcdA=40ng/ml
- TcdA=8ng/ml
- TcdA=1.6ng/ml

Figure 16

| | Diarrhea | | | Weight Change | | | | Survival |
|---|---|---|---|---|---|---|---|---|
| | occurrence | Day1 score | Day2 score | Overall | Day2 | Day3 | Day4 | |
| 200ug/kg | - | - | - | - | √ | - | √ | √ |
| 1mg/kg | √ | - | √ | - | √ | √ | - | √ |
| 5mg/kg | √ | √ | √ | √ | √ | √ | √ | √ |

Figure 17

| | Diarrhea | | | Weight Change | | | | Survival |
|---|---|---|---|---|---|---|---|---|
| | occurrence | Day1 score | Day2 score | Overall | Day2 | Day3 | Day4 | |
| 200ug/kg | √ | √ | - | - | - | - | - | - |
| 1mg/kg | - | - | - | - | - | - | √ | - |
| 5mg/kg | - | - | - | √ | - | - | √ | - |

US 10,961,299 B2

TETRA-SPECIFIC, OCTAMERIC BINDING AGENTS AND ANTIBODIES AGAINST *CLOSTRIDIUM DIFFICILE* TOXIN A AND TOXIN B FOR TREATMENT OF *C. DIFFICILE* INFECTION

STATEMENT OF FEDERALLY SPONSORED RESEARCH AND DEVELOPMENT

This invention was made with government support under Grant No. DK084509 and Grant No. AI109776 awarded by the National Institutes of Health. The government has certain rights in the invention.

SEQUENCE LISTING

A sequence listing in electronic (ASCII text file) format is filed with this application and incorporated herein by reference. The name of the ASCII text file is "2016_0045A_ST25"; the file was created on Feb. 5, 2016; the size of the file is 108 KB.

BACKGROUND

The bacterium *Clostridium difficile* is the most common cause of nosocomial antibiotic-associated diarrhea as well as the etiologic agent of pseudomembranous colitis. It is estimated that over 500,000 cases of *C. difficile*-associated disease (CDI) occur annually in the United States, with the annual mortality rate ranging from about 3-17%, depending on the strains.

Available options for treating CDI patients are limited and the recurrence rate is high (20-35% of patients). The risk of further episodes of CDI in recurrent patients can be more than 50% and a subset of patients will have multiple recurrences. Recurrent CDI can be caused by the same strain or different ones. With the emergence of hypervirulent and antibiotic-resistant strains, the incidence of mortality in patients with *C. difficile* infection is increasing rapidly.

Standard therapy includes antibiotic treatment (vancomycin and metronidazole), which is not fully effective and has a disruptive effect on gut microflora leading to multiple relapses. While other interventions have been tried (e.g., probiotics, toxin-absorbing polymers, and toxoid vaccines), neither prevention nor treatment strategies have kept up with the increased incidence and seriousness of this infection.

Newer immune-based therapies have been shown to be somewhat effective in clinical trials and include intravenous immunoglobulin (IVIG) against severe CDI and human monoclonal antibodies against recurrent CDI. Fidaxomicin, a narrow spectrum macrocyclic antibiotic, has shown an effect similar to oral vancomycin on CDI but was significantly better at lowering the relapse rate.

It is a frustrating condition that is difficult to treat and may affect patients for months or even years, causing tremendous morbidity and mortality. Accordingly, there is a need for new treatments for both primary and recurrent CDI and preventions for subjects at risk of developing CDI.

BRIEF SUMMARY OF INVENTION

*C. difficile*-associated disease is mainly caused by two large exotoxins, i.e., toxin A (TcdA) and toxin B (TcdB), produced by the bacteria. These toxins are structurally similar, 300-kDa single-chain proteins that exhibit similar modes of action on host cells. Both toxins target host Rho GTPases, leading to enzyme inactivation, followed by cytoskeleton disorganization and apoptosis. In intestinal epithelial cells, TcdA catalyzes glucosylation of the Rho GTPases, leading to reorganization of the actin cytoskeleton with accompanying morphological changes such as complete rounding of cells and destruction of the intestinal barrier function. The toxins can individually cause CDI in animals, and TcdA$^-$ TcdB$^-$ strains of the bacteria are avirulent.

Systemic and mucosal antibodies against the toxins confer protection against CDI. Because TcdA and TcdB are essential virulence factors for *C. difficile*, antibodies produced against both toxins can treat and protect against toxigenic *C. difficile* infection in animal models.

The present invention builds on existing knowledge regarding anti-TcdA and anti-TcdB antibodies for the treatment and prevention of CDI, and the symptoms of CDI. Provided herein are novel, antibody-based binding agents derived from human and camelid immunoglobulins. These binding agents recognize and bind with specificity to *C. difficile* TcdA and/or TcdB. Some of these binding agents exhibit toxin-neutralizing activity. These binding agents can be used to treat or prevent primary and recurrent CDI, as well as the symptoms of primary and recurrent CDI.

As discussed in detail below, camelid animals produce a class of functional immunoglobulins that lack light chains and are thus heavy chain-only antibodies (HCAbs). The $V_H$ domain of HCAbs, called $V_HH$, is similar to the conventional human $V_H$ domain but has unique sequence and structural characteristics. DNA encoding this domain can be readily cloned and expressed in microbes to yield soluble protein monomers that retain the antigen-binding properties of the parent HCAb. These $V_HH$ peptide monomer binding agents are small (~15 kDa), easy to produce, and generally more stable than conventional antibody fragments. They can also be produced as fusion proteins with human antibodies, such as IgG, and fragments of human antibodies, such as Fc domains.

The binding agents of the present invention thus include simple $V_HH$ peptide monomers and linked groups of $V_HH$ peptide monomers (comprising 2, 3, 4, or more monomers), as well as more complex binding agents that comprise $V_HH$ peptide monomers joined to antibody Fc domains, as well as $V_HH$ peptide monomers joined to partial or full IgG antibodies.

In a first embodiment, the present invention is directed to binding agents comprising $V_HH$ peptide monomers and linked groups of $V_HH$ peptide monomers comprising two, three, four, or more monomers, each of which binds TcdA and/or TcdB, preferably with specificity. Thus, the invention encompasses $V_HH$ peptide binding agents comprising at least one $V_HH$ peptide monomer, wherein each $V_HH$ peptide monomer has binding specificity for a unique epitope of *C. difficile* toxin A (TcdA) or toxin B (TcdB). In certain aspects, these binding agents comprise two, three, four, or more linked $V_HH$ peptide monomers. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In certain aspects of this embodiment, the binding agents bind to TcdA and/or TcdB with specificity. In certain aspects of this embodiment, the binding agents exhibit TcdA and/or TcdB neutralizing activity.

In a specific aspect of this embodiment, the binding agent comprises four linked $V_HH$ peptide monomers where two of the monomers have binding specificity for epitopes of TcdA and two of the monomers have binding specificity for epitopes of TcdB. The epitopes of TcdA may be the same or different. The epitopes of TcdB may be the same or different.

In a specific aspect of this embodiment, the binding agent comprises the amino acid sequence set forth in SEQ ID NO:19 or a sequence variant thereof having at least 95% sequence identity thereto, and wherein the sequence variant retains TcdA and/or TcdB binding specificity, or the sequence variant retains toxin neutralizing activity, or both. In some instances, variant amino acids of the sequence variant are located in framework regions of the $V_HH$ peptide monomers.

In a second embodiment, the invention is directed to binding agents comprising $V_HH$ peptide monomers joined to IgG antibodies, where the binding agents bind TcdA and/or TcdB. In these IgG-based binding agents, the variable regions of the light and heavy chains of IgG antibodies are replaced by one, two, three, four or more of the $V_HH$ peptide monomers.

In certain aspects of this embodiment, these binding agents comprise two, three, four, or more linked $V_HH$ peptide monomers joined to the amino termini of IgG light and heavy chains in place of the variable regions. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In a first sub-embodiment, the invention is directed to tetra-specific, octameric binding agents comprising an IgG antibody, two sets of linked first and second $V_HH$ peptide monomers, and two sets of linked third and fourth $V_HH$ peptide monomers, wherein the IgG antibody comprises two arms, each arm comprising a heavy chain lacking a variable region and a light chain lacking a variable region, and each chain having an amino terminus, wherein for each arm of the antibody, one set of linked first and second $V_HH$ peptide monomers is joined to the amino terminus of the light chain, and one set of linked third and fourth $V_HH$ peptide monomers is joined to the amino terminus of the heavy chain, and wherein the $V_HH$ peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer).

In this sub-embodiment, the first, second, third and fourth $V_HH$ peptide monomers each has binding specificity for a different epitope.

In certain aspects of this sub-embodiment, two of the $V_HH$ peptide monomers have binding specificity for epitopes of TcdA and two of the $V_HH$ peptide monomers have binding specificity for epitopes of TcdB.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the light (kappa) chain of the binding agent comprises the amino acid sequence set forth in SEQ ID NO:46 (AA6/E3 kappa) or a sequence variant having at least 95% sequence identity thereto, and the heavy chain of the binding agent comprises the amino acid sequence set forth in SEQ ID NO:44 (AH3/5D heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin-neutralizing activity, or both. The variant amino acids of the sequence variants may be located in framework regions of the $V_HH$ peptide monomers.

In a second sub-embodiment, the invention is directed to bi-specific or tetra-specific, tetrameric binding agents comprising an IgG antibody and first, second, third and fourth $V_HH$ peptide monomers, wherein the IgG antibody comprises two arms, each arm comprising a heavy chain lacking a variable region and a light chain lacking a variable region, and each chain having an amino terminus, wherein for a first arm of the antibody, the first $V_HH$ peptide monomer is joined to the amino terminus of the light chain, and the second $V_HH$ peptide monomer is joined to the amino terminus of the heavy chain, wherein for a second arm of the antibody, the third $V_HH$ peptide monomer is joined to the amino terminus of the light chain, and the fourth $V_HH$ peptide monomer is joined to the amino terminus of the heavy chain, and wherein the $V_HH$ peptide monomers have binding specificity for an epitope of *Clostridium difficile* toxin A (TcdA) or toxin B (TcdB). When the binding agent is "tetra-specific", it recognizes four different toxin epitopes; when "bi-specific" it recognizes two different toxin epitopes. The binding agents are "tetrameric" as they bear four $V_HH$ peptide monomers (when bi-specific, the first and third monomer have the same sequence and bind the same epitope, and the second and fourth monomers have the same sequence and bind the same epitope; when tetra-specific, each of the monomers has a different sequence and binds a different epitope).

When the binding agent is bi-specific, the first and second monomers have binding specificity for different epitopes, the first and third monomers have identical amino acid sequences, and the second and fourth monomers have identical amino acid sequences. One of the $V_HH$ peptide monomers may have binding specificity for an epitope of TcdA and one of the $V_HH$ peptide monomers may have binding specificity for an epitope of TcdB.

When the binding agent is tetra-specific, each of the $V_HH$ peptide monomers has binding specificity for a different epitope. Two of the $V_HH$ peptide monomers may have binding specificity for epitopes of TcdA and two of the $V_HH$ peptide monomers may have binding specificity for epitopes of TcdB.

In certain aspects of this sub-embodiment, each of the $V_HH$ peptide monomers has binding specificity for epitopes of TcdA.

In certain aspects of this sub-embodiment, each of the $V_HH$ peptide monomers has binding specificity for epitopes of TcdB.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the light (kappa) chain of the binding agent comprises the amino acid sequence set forth in SEQ ID NO:40 (AA6 kappa) or a sequence variant having at least 95% sequence identity thereto, and the heavy chain of the binding agent comprises the amino acid sequence set forth in SEQ ID NO:36 (AH3 heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin neutralizing activity, or both. The variant amino acids of the sequence variant may be located in framework regions of the $V_HH$ peptide monomers.

In another specific aspect of this sub-embodiment, the light (kappa) chain of the binding agent comprises the amino acid sequence set forth in SEQ ID NO:42 (E3 kappa) or a sequence variant having at least 95% sequence identity thereto, and the heavy chain of the binding agent comprises the amino acid sequence set forth in SEQ ID NO:38 (5D heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin neutralizing activity, or both. The variant amino acids of the sequence variants may be located in framework regions of the $V_HH$ peptide monomers.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

In a third embodiment, the invention is directed to binding agents comprising $V_HH$ peptide monomers joined to antibody Fc domains, where the binding agents bind TcdA and/or TcdB. In these Fc domain-based binding agents, one, two, three, four or more of the $V_HH$ peptide monomers are joined to the hinge, $C_H2$ and $C_H3$ regions of each arm of Fc domain of an antibody heavy chain. Thus, the peptide monomers replace the Fab regions of an antibody.

In certain aspects of this embodiment, these binding agents comprise two, three, four, or more linked $V_HH$ peptide monomers joined to the amino termini of the arms of the Fc domains. The $V_HH$ peptide monomers include, but are not limited to, the $V_HH$ peptide monomers 5D (SEQ ID NO:1), E3 (SEQ ID NO:3), AA6 (SEQ ID NO:5) and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In a first sub-embodiment, the invention is directed to tetra-specific, octameric binding agents comprising an antibody Fc domain and two sets of linked first, second, third and fourth $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first, second, third and fourth $V_HH$ peptide monomers is joined to the amino terminus of the arm, and where the $V_HH$ peptide monomers have binding specificity for an epitope of Clostridium difficile toxin A (TcdA) or toxin B (TcdB). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer).

In certain aspects of this sub-embodiment, the first, second, third and fourth $V_HH$ peptide monomers each has binding specificity for a different epitope.

In certain aspects of this sub-embodiment, two of the $V_HH$ peptide monomers have binding specificity for epitopes of TcdA and two of the $V_HH$ peptide monomers have binding specificity for epitopes of TcdB.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the binding agent comprises the amino acid sequence set forth in SEQ ID NO:22 (ABAB-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In a second sub-embodiment, the invention is directed to bi-specific, tetrameric binding agents comprising an antibody Fc domain and two sets of linked first and second $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first and second $V_HH$ peptide monomers is joined to the amino terminus of the arm, and where the $V_HH$ peptide monomers have binding specificity for an epitope of Clostridium difficile toxin A (TcdA) or toxin B (TcdB). This binding agent is termed "bi-specific" as it recognizes two different toxin epitopes. It is termed "tetrameric" as it bears four $V_HH$ peptide monomers (two copies of the first monomer, and two copies of the second monomer).

In certain aspects of this sub-embodiment, the first and second $V_HH$ peptide monomers have binding specificity for the same or different epitopes.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the binding agent comprises the amino acid sequence set forth in SEQ ID NO:32 (AH3/5D-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In another specific aspect of this sub-embodiment, the binding agent comprises the amino acid sequence set forth in SEQ ID NO:34 (AA6/E3-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

The invention includes humanized variants of each the binding agents provided in the various embodiments and aspects defined herein. Likewise, the invention includes epitope binding fragments of each the binding agents provided in the various embodiments and aspects defined herein.

The invention includes pharmaceutical formulations comprising one or more of the binding agents defined herein and a pharmaceutically acceptable carrier or diluent.

The invention includes polynucleotides comprising nucleotide sequences encoding each the binding agents provided in the various embodiments and aspects defined herein, as well as complementary strands thereof. The invention also includes expression vectors comprising the polynucleotides, and host cells comprising the expression vectors. The invention further includes methods of producing the binding agents define herein, comprising culturing the host cells under conditions promoting expression of the binding agents encoded by the expression vectors, and recovering the binding agents from the cell cultures.

In a fourth embodiment, the invention is directed to methods of treating or preventing a disease symptom induced by *C. difficile* in a subject comprising administering a therapeutically-effective amount of one or more binding agents as defined herein to a subject having *C. difficile* infection or a risk of developing *C. difficile* infection.

In a fifth embodiment, the invention is directed to methods of neutralizing *C. difficile* toxin TcdA and/or TcdB in a subject infected by *C. difficile* comprising administering a therapeutically-effective amount of one or more binding agents as defined herein to a subject having *C. difficile* infection.

In a sixth embodiment, the invention is directed to methods of treating or preventing *C. difficile* infection in a subject comprising administering a therapeutically-effective amount of one or more of the binding agents as defined herein to a subject having *C. difficile* infection or a risk of developing *C. difficile* infection.

In certain aspects of the sixth embodiment, the method further comprises administering a therapeutically-effective amount of an antibiotic to the subject.

In certain aspects of the methods, the binding agent is in a pharmaceutical formulation comprising the binding agent and a pharmaceutically acceptable carrier or diluent.

In certain aspects of the methods, the therapeutically-effective amount of the binding agent is between 10 ug/kg and 100 mg/kg of the agent per body weight of the subject.

In certain aspects of the methods, the agent is administered to the subject orally, parenterally or rectally.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

(FIG. 2C) Diagram of two heterodimers against TcdA or TcdB. $His_{(6)}$ tag on N-terminus facilitates purification; a flexible spacer (FS) separate the two $V_HH$s. (FIG. 2D) Dimer 5D/E3 increases its neutralizing activity at least 10-fold over a simple mix of the two $V_HH$s. Heterodimers fully protected mice from lethal ip challenge with TcdB (FIG. 2E) or TcdA (FIG. 2F).

Figure 5:
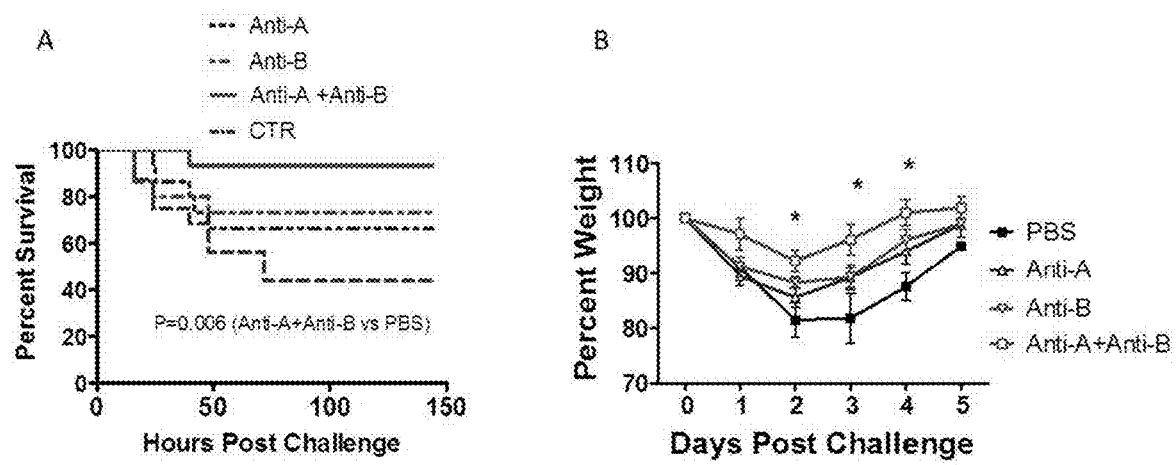
FIG. 5. Anti-toxin sera against both toxins protect mice from CDI. Mice were i.p. injected with 50 ul alpaca anti-sera against TcdA ("Anti-A"), TcdB ("Anti-B"), TcdA+TcdB ("Anti-A+Anti-B") or with 100 ul presera or PBS ("CTR") for 4 hours before *C. difficile* spore (UK1 strain, $10^6$ spores/mouse) inoculation. Mouse survival (FIG. 5A; Anti-A+

Anti-B vs. PBS, p=0.006) and weight loss (FIG. 5B) are illustrated (*, p<0.05 between Anti-A+Anti-B vs. control).

Figure 6:
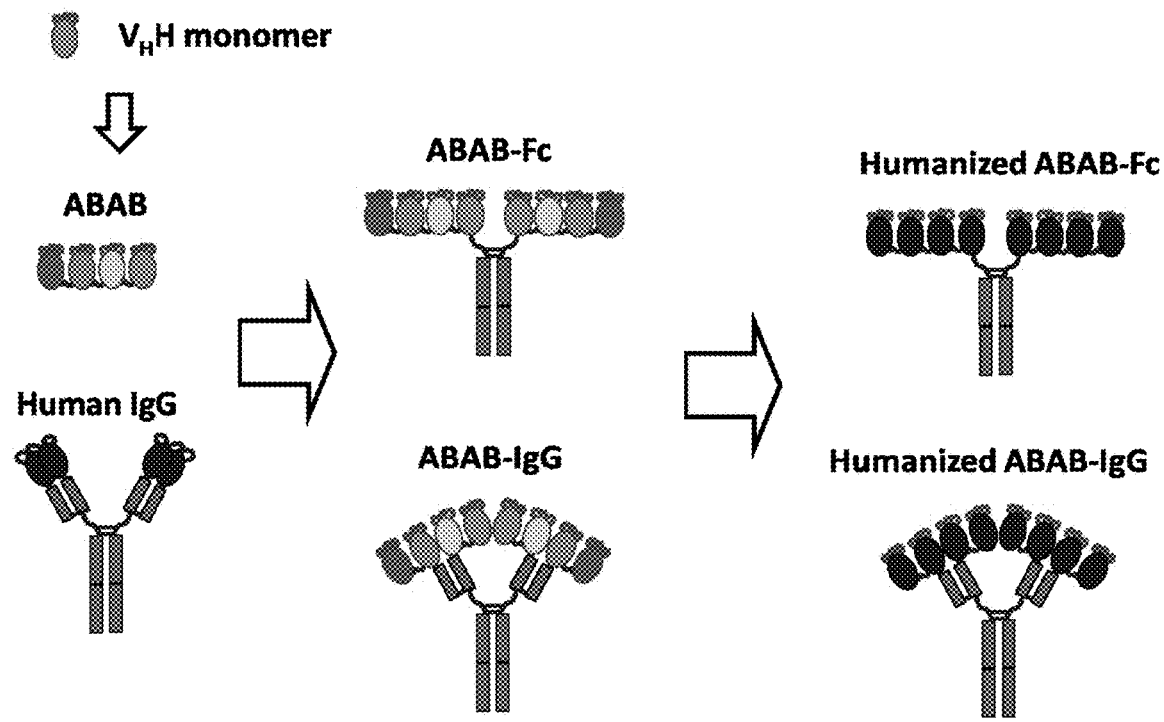

FIG. 6. Illustration of strategies for making binding agents of the invention.

Figure 7:
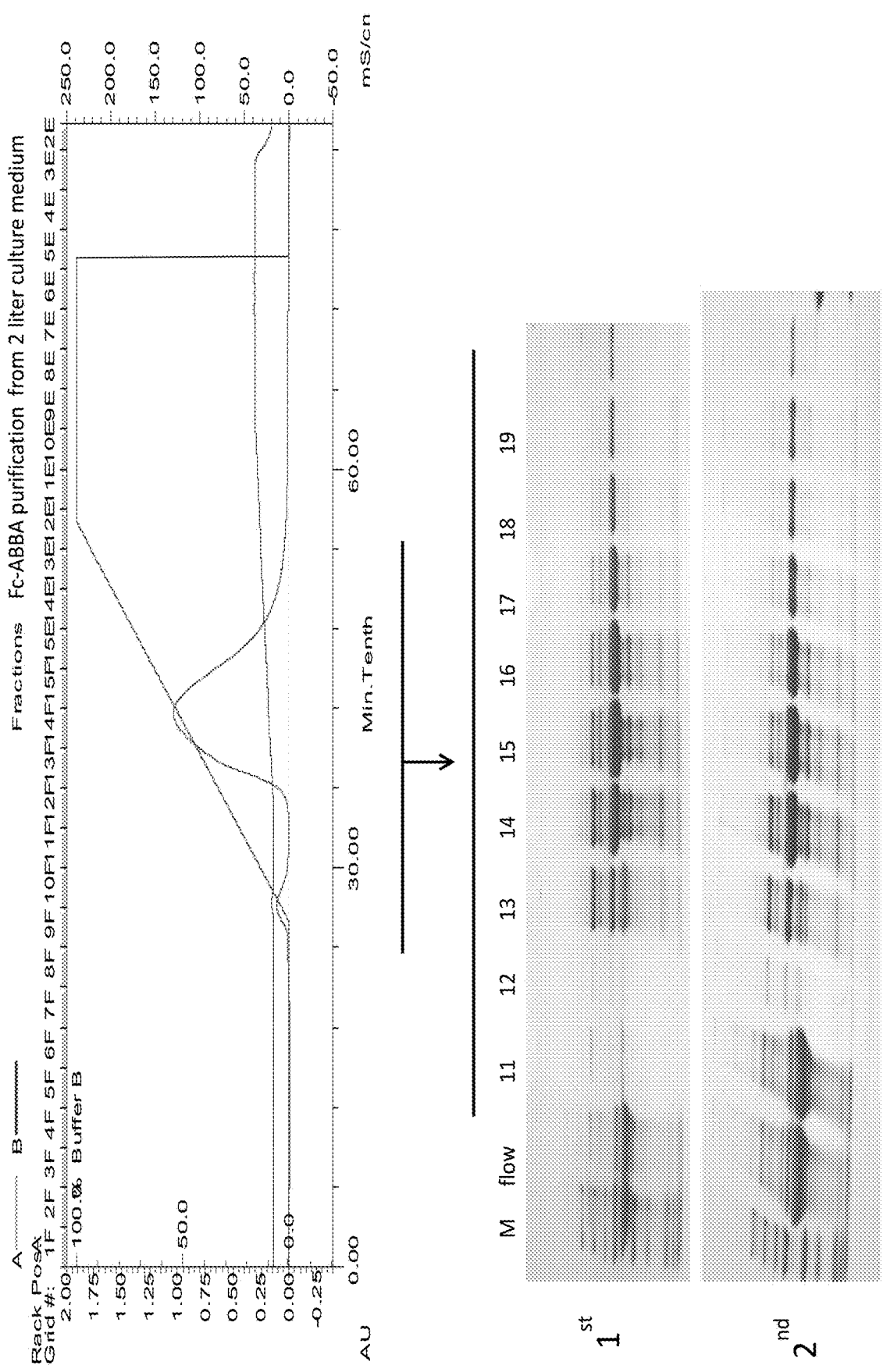

FIG. 7. Fractionation and purification of ABAB-Fc ("Fc-ABBA") from cell cultures.

Figure 8:
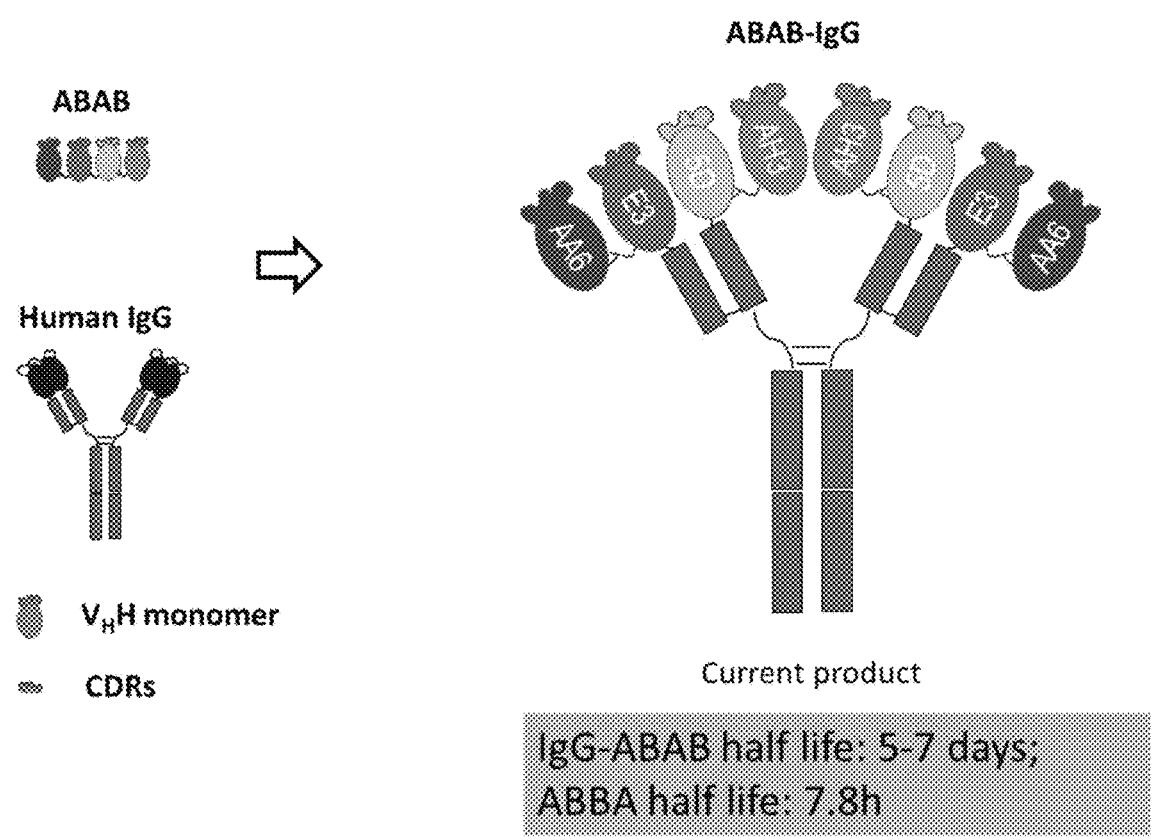

FIG. 8. The diagram of the ABAB and ABAB-IgG molecules.

Figure 9:
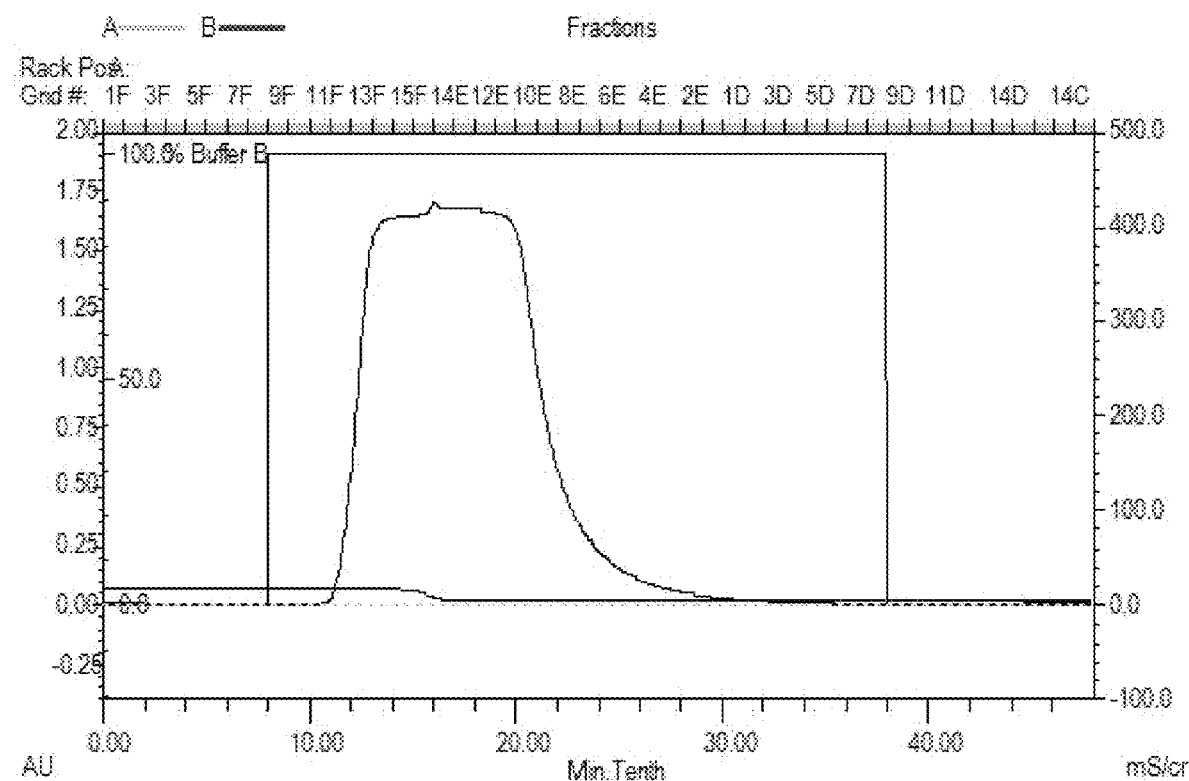

FIG. 9. Fractionation of culture supernatant from HEK293 cells expressing ABAB-IgG1. The peak shows the UV OD reading of the eluted ABAB-IgG1 from Protein A beads.

Figure 10:
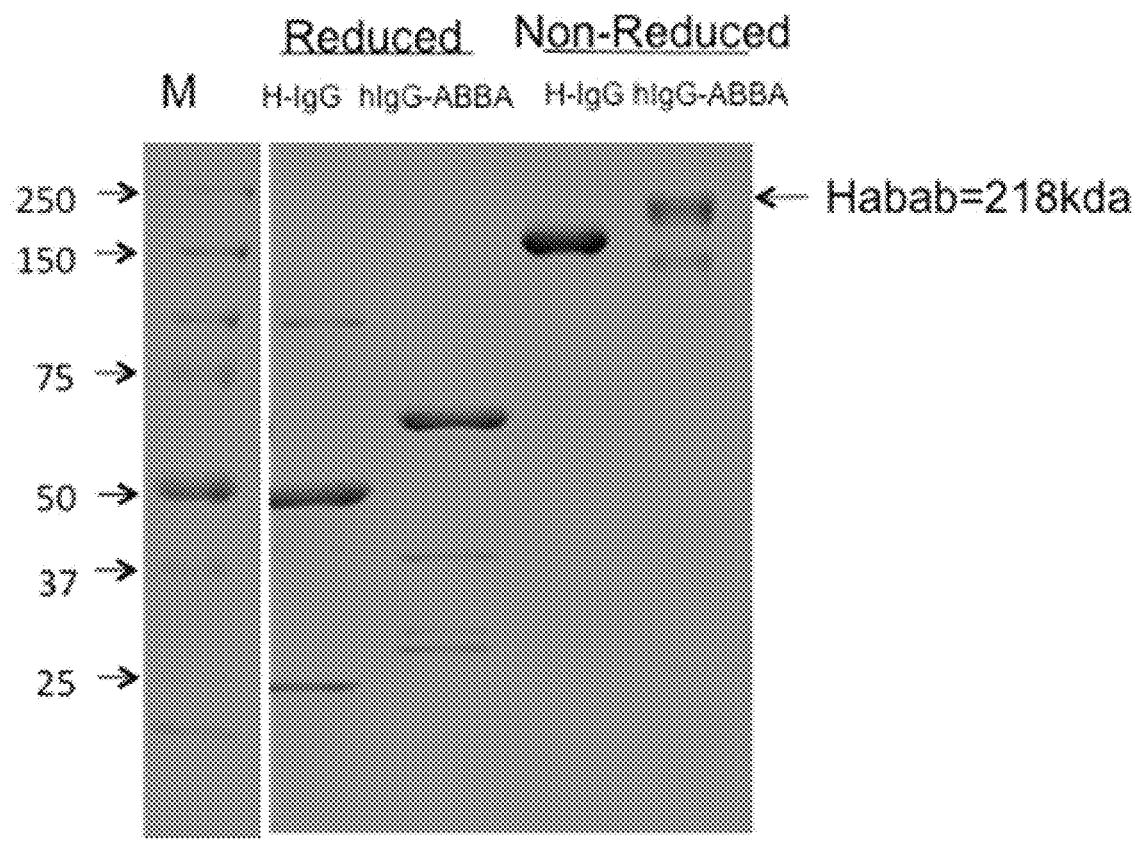

FIG. 10. SDS-PAGE of reduced and non-reduced electrophoresis of purified ABAB-IgG1 ("IgG-ABBA" and "Habab").

Figures 11A, 11B:
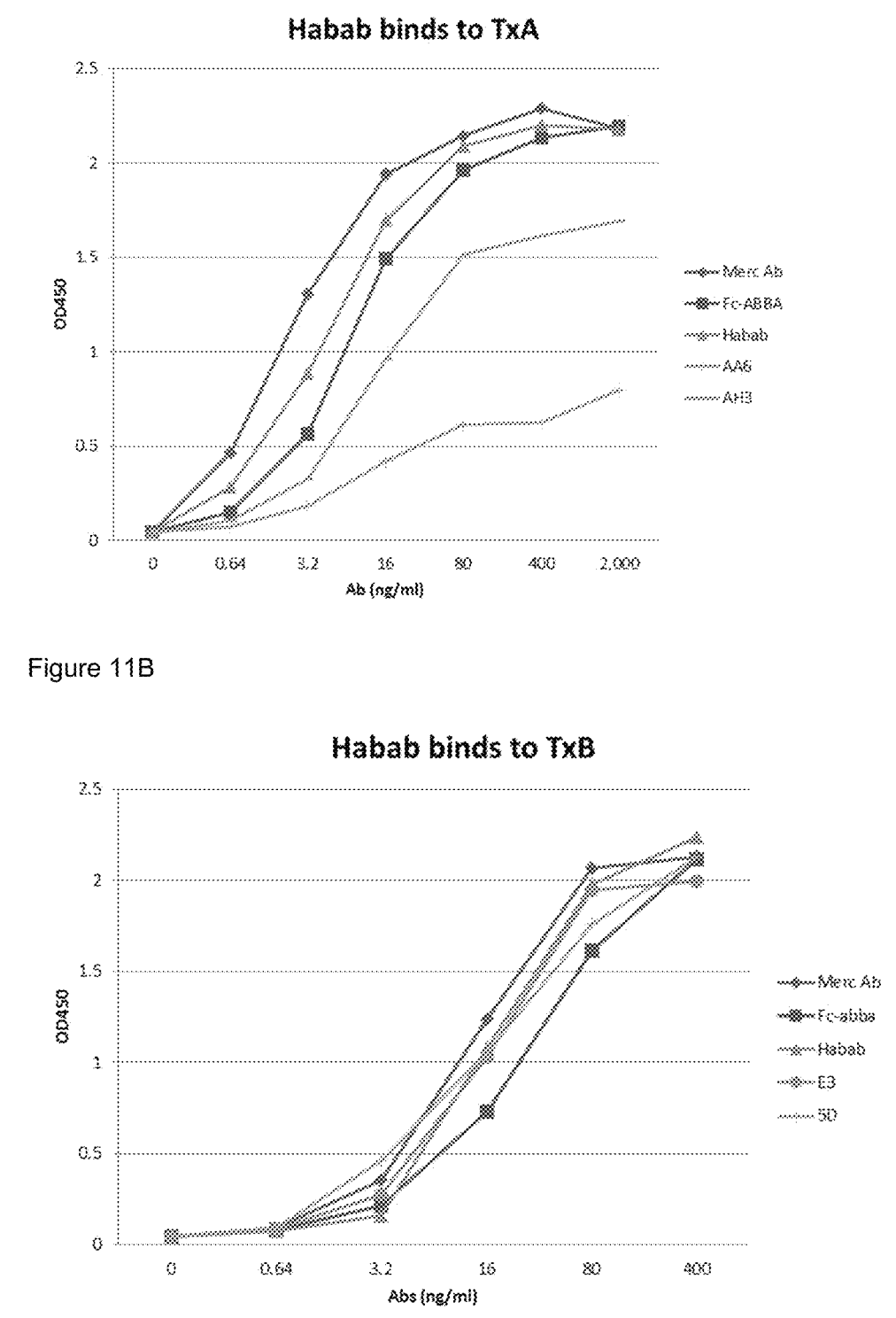

FIGS. 11A-11B. ELISA analysis of binding of ABAB-IgG to TcdA (FIG. 11A) and TcdB (FIG. 11B) as compared with the binding of the individual VHHs to the respective toxins.

FIGS. 12A-12B. Sandwich ELISA analysis of simultaneous binding of the tetraspecific antibody IgG-ABAB to both TcdA and TcdB. FIG. 12A shows serially diluted ABAB-IgG added to ELISA plates coated with TcdA (TxA), followed by TcdB (TxB). FIG. 12B shows serially diluted ABAB-IgG added to ELISA plates coated with TcdB (TxB), followed by TcdA (TxA).

Figure 13A:
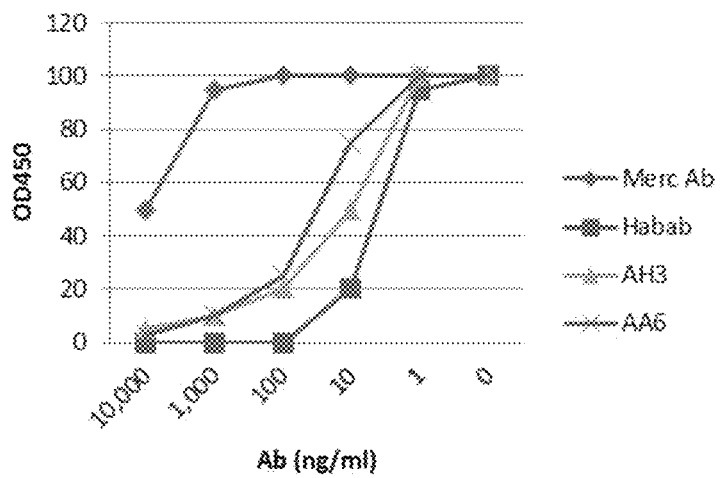
Figure 13B:
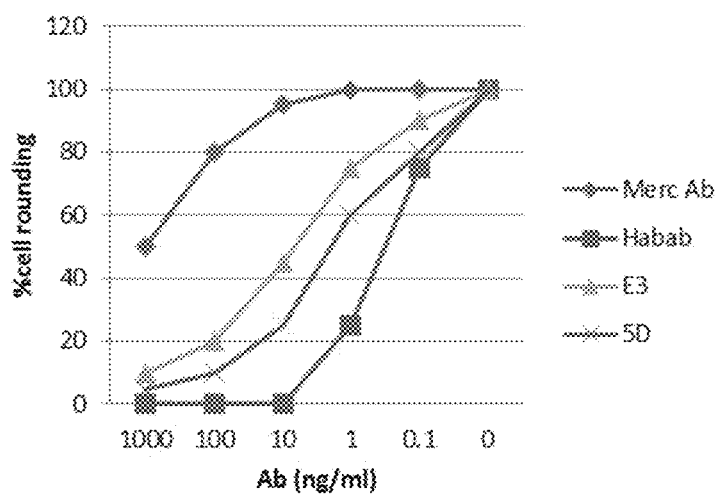

FIGS. 13A-13B. ABAB-IgG neutralizing activities against TcdA (FIG. 13A) and TcdB (FIG. 13B).

Figure 14:
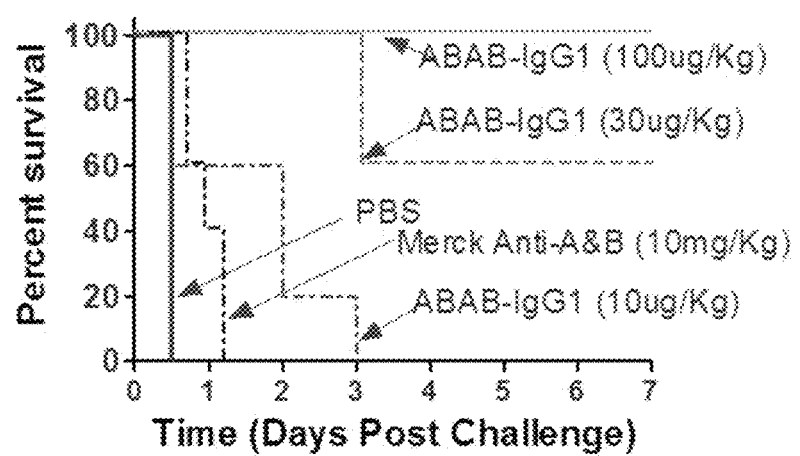

FIG. 14. Graph showing in vivo neutralizing activity of ABAB-IgG against *C. difficile* infection in mice versus Merck antibodies against TcdA and TcdB.

Figure 15:
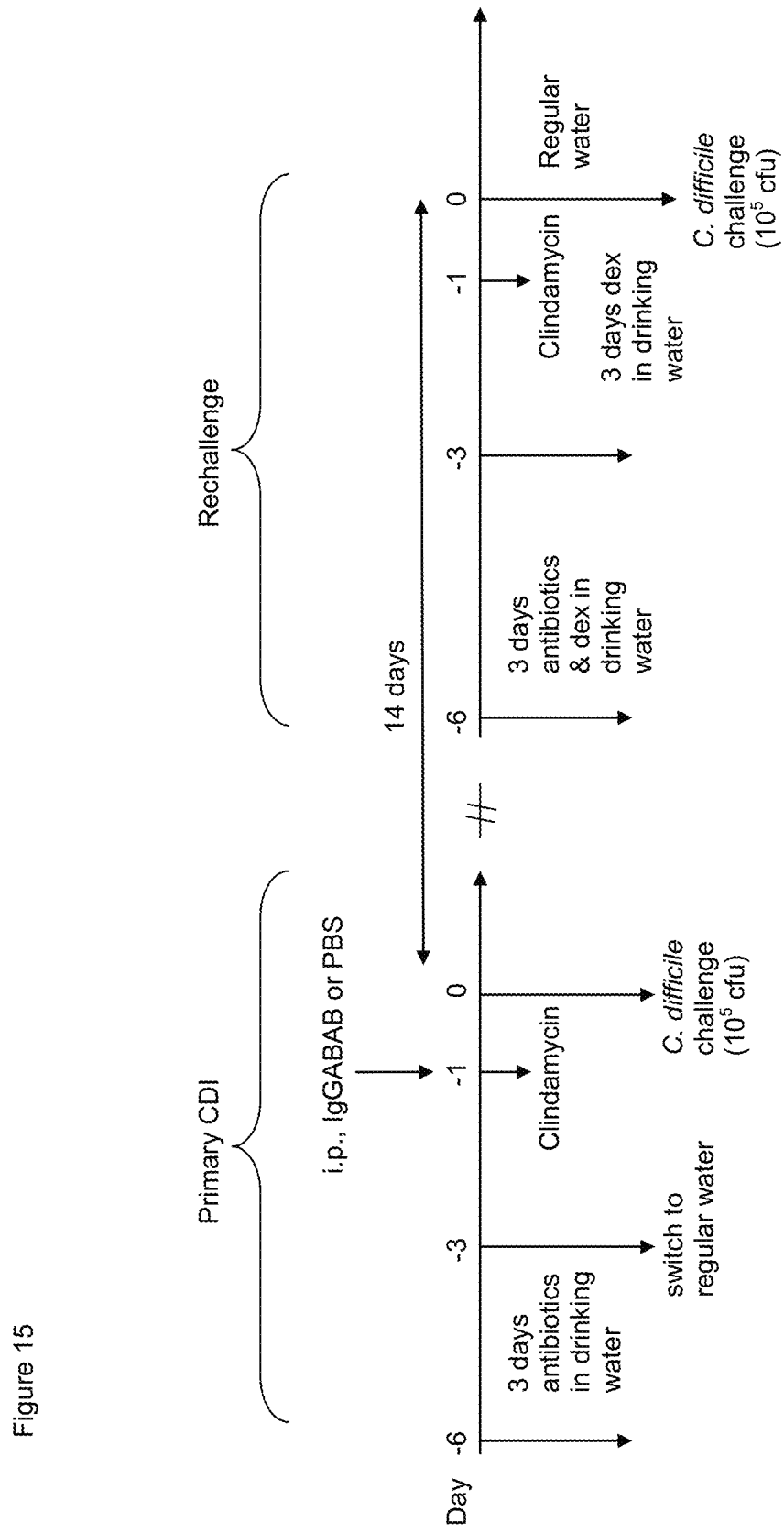

FIG. 15. Design of studies on the effects of prophylactic ABAB-IgG against *C. difficile* infection.

FIG. 16. Effect of ABAB-IgG against CDI: prophylactic treatment—Summary.

FIG. 17. Effect of ABAB-IgG against CDI: Re-challenge—Summary.

DETAILED DESCRIPTION OF THE INVENTION

I. Definitions

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

The primary effectors of CDI in animals are the *C. difficile* exotoxins TcdA and TcdB (toxin A and B). These toxins are structurally similar, 300-kDa single-chain proteins that exhibit similar modes of action on host cells. Both toxins target host Rho GTPases, leading to enzyme inactivation, followed by cytoskeleton disorganization and apoptosis. In intestinal epithelial cells, TcdA catalyzes glucosylation of the Rho GTPases, leading to reorganization of the actin cytoskeleton with accompanying morphological changes such as complete rounding of cells and destruction of the intestinal barrier function. The toxins can individually cause CDI in animals, and TcdA$^-$ TcdB$^-$ strains of the bacteria are avirulent.

Numerous independent studies have demonstrated that systemic and mucosal antibodies against the toxins confer protection against CDI. Because TcdA and TcdB are essential virulence factors for *C. difficile*, antibodies produced against both toxins can protect against toxigenic *C. difficile* infection in animal models. In humans, high serum levels of antitoxin antibodies are associated with reduced disease severity and incidence of relapse. Therefore, a preventative rationale for systemically and orally administered antitoxin antibodies exists. However, monoclonal antibodies targeting a single epitope are typically low affinity, and use of such antibodies runs the risk of inducing mutations within the epitopes of the toxins thereby creating additional strains. Thus, neutralizing antitoxins targeting multiple, key, and conserved toxin epitopes are highly desirable.

Camelid animals produce a class of functional immunoglobulins that lack light chains and are thus heavy chain-only antibodies (HCAbs). HCAbs bind to target antigens with binding properties equivalent to those achieved by conventional human IgG. The $V_H$ region of HCAbs, called $V_HH$, is similar to conventional $V_H$ domains but has unique sequence and structural characteristics. DNA encoding this domain can readily be cloned and expressed in microbes to yield soluble protein monomers retaining the antigen-binding properties of the parent HCAb. These $V_HH$ peptide monomer binding agents are small (~15 kDa), easy to produce, and generally more stable than conventional antibody fragments. They can also be produced in concert with IgG antibodies and antibody Fc domains.

The present invention utilizes the advantageous characteristics of HCAbs in the production of binding agents that can be used in the treatment and prevention of CDI. $V_HH$ peptide monomers were screened for TcdA and TcdB epitope recognition and binding. Those monomers that exhibited epitope binding and had toxin-neutralizing activity were linked to produce the binding agents of the invention. The binding agents include simple $V_HH$ peptide monomers and linked groups of $V_HH$ peptide monomers (comprising 2, 3, 4, or more monomers), as well as more complex binding agents that comprise $V_HH$ peptide monomers joined to antibody Fc domains, as well as $V_HH$ peptide monomers joined to IgG antibodies (see FIG. 6).

$V_HH$ Monomers & $V_HH$ Heterodimers

Figure 1:
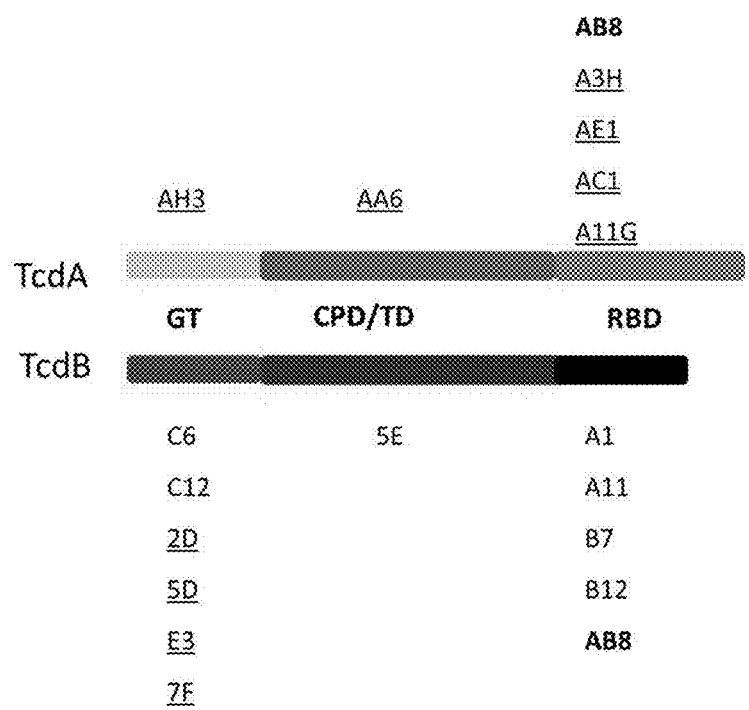
FIG. 1. A diagram of *C. difficile* toxins TcdA and TcdB, showing the glucosyltransferase domains (GT), cysteine protease domains (CPD), translocation domains (TD) and receptor binding domains (RBD) of each toxin. $V_HH$s that recognize and bind the different toxin domains are shown. Those that are underlined are those that have toxin-neutralizing activity.

The inventors established an efficient platform to screen $V_HH$ monomers against specific domains of both *C. difficile* toxins. Using highly immunogenic atoxic holotoxins for immunization, and bioactive chimeric toxins (with normal domain functions) for screening, panels of $V_HH$ monomers binding to different domains of TcdA or TcdB were prepared. A majority of these $V_HH$ monomers possessed potent neutralizing activity and their binding to specific domains was determined (FIG. 1).

Several of the $V_HH$ monomers bind to highly conserved TcdA/TcdB epitopes. For example, the E3 $V_HH$ monomer binds to the Rho GTPase binding site and blocks glucosylation; the AH3 $V_HH$ monomer binds to the GT domain of the toxin; the 7F $V_HH$ monomer binds to cysteine protease cleavage sites and blocks GT domain cleavage and release. Some $V_HH$ monomers have potent toxin neutralizing activity, capable of blocking toxin cytotoxic activity at nM concentrations (monomers underlined in FIG. 1; see also FIGS. 2A and 2B). Table 1 references amino and nucleic acid sequences in the Sequence Listing for some of these $V_HH$ peptide monomers, both wild-type and codon-optimized versions. While both the optimized and non-optimized versions can be used in the production of the various binding agents of the present invention, the codon-optimized versions are preferred for expression in mammalian cells.

The present invention includes each of the $V_HH$ peptide monomers referenced in Table 1 as well as sequence variants thereof having at least 90%, 91%, 92%, 93%, 94%, 95%, 96%, 97%, 98%, or 99% sequence identity over the entire length of the peptide sequence and retaining the toxin binding and/or neutralizing activity of the wild-type peptide. The present invention also includes polynucleotide sequences encoding each of the $V_HH$ peptide monomers of Table 1 and the sequence variants thereof, as well as complementary strands thereof.

TABLE 1

| Name | Codon Optimized? | Location of epitope | SEQ ID NO for Amino Acid Seq. | SEQ ID NO for Nucleic Acid Seq. |
|---|---|---|---|---|
| 5D | Yes | TcdB glucosyltransferase domain | 1 | 2 |
| E3 | Yes | TcdB glucosyltransferase domain | 3 | 4 |
| AA6 | Yes | TcdA cysteine protease domain | 5 | 6 |
| AH3 | Yes | TcdA glucosyltransferase domain | 7 | 8 |
| 5D | No | TcdB glucosyltransferase domain | 48 | 49 |
| E3 | No | TcdB glucosyltransferase domain | 50 | 51 |
| AA6 | No | TcdA cysteine protease domain | 52 | 53 |
| AH3 | No | TcdA glucosyltransferase domain | 54 | 55 |

To enhance the binding activity of the peptide monomers, $V_HH$ peptide homo- and hetero-dimer binding agents were created, where two $V_HH$ peptide monomers are linked (FIG. 2C). Homodimer binding agents comprise two identical monomers that bind identical epitopes on two different toxins. Heterodimer binding agents comprise two different monomers that bind two distinct epitopes of the same toxin or distinct epitopes on two different toxins. The $V_HH$ heterodimers were found to possess substantially enhanced neutralizing activities compared with equimolar mixtures of the individual $V_HH$ peptide monomers comprising the heterodimers (FIG. 2D). Indeed, heterodimers 5D/E3 and AH3/AA6 were found to fully protect mice from lethal systemic TcdB or TcdA challenge respectively, whereas mixed 5D and E3, or AA6 alone were only partially protective (FIGS. 2E and F).

The $V_HH$ monomers in the homo- and hetero-dimers are linked using a short, flexible linker of between 10 and 20 amino acids. Suitable linkers include those provided in Table 2. Table 2 also includes codon-optimized versions of the three linkers. While both the optimized and non-optimized versions can be used in the production of the various binding agents of the present invention, the codon-optimized versions are preferred for expression in mammalian cells.

TABLE 2

| Name | Codon Optimized? | SEQ ID NO for Amino Acid Seq. | SEQ ID NO for Nucleic Acid Seq. |
|---|---|---|---|
| Linker-1 | Yes | 9 | 10 |
| Linker-2 | Yes | 11 | 12 |
| Linker-3 | Yes | 13 | 14 |
| Linker-1 | No | 56 | 57 |
| Linker-2 | No | 58 | 59 |
| Linker-3 | No | 60 | 61 |

It will be understood by the skilled artisan that minor changes can be made to the sequence of the flexible linker without departing from the properties of the peptide. Sequence variants of the flexible linker having at least 90%, 91%, 92%, 93%, 94%, 95%, 96%, 97%, 98%, or 99% sequence identity over the entire length of the peptide sequence and retaining properties of the linker upon which they are based may thus be used.

The present invention includes $V_HH$ peptide homodimer binding agents comprising pairs of any of the monomers listed in Table 1, linked by a flexible linker as defined above. The present invention also includes $V_HH$ peptide heterodimer binding agents comprising any combination of two of the monomers listed in Table 1, linked by a flexible linker as defined above. Exemplary heterodimers are provided in Table 3.

TABLE 3

| Name | SEQ ID NO for Amino Acid Seq. | SEQ ID NO for Nucleic Acid Seq. |
|---|---|---|
| AH3-5D | 15 | 16 |
| AA6-E3 | 17 | 18 |
| 5D-E3 | 62 | 63 |
| AH3-AA6 | 64 | 65 |

The present invention also includes sequence variants of the $V_HH$ peptide homo- and hetero-dimers having at least 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each the $V_HH$ peptide homo-hetero-dimers and the sequence variants thereof, as well as complementary strands thereof.

The invention also includes $V_HH$ peptide homo- and hetero-trimer binding agents where three monomers are linked using the flexible linkers defined above in Table 2. Any combination of the monomers of Table 1 may be used, including trimers comprising three copies of the same monomer, trimers comprising two copies of one monomer and a single copy of another, and trimers comprising three different monomers. Sequence variants of the $V_HH$ peptide homo- and hetero-trimers are included in the invention, having at least 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each the $V_HH$ peptide homo-hetero-trimers and the sequence variants thereof, as well as complementary strands thereof.

ABAB

The success of the peptide monomers and heterodimers allowed the inventors to develop binding agents comprising four linked $V_HH$ peptide monomers. This was a goal of the research as earlier work had shown that the most useful agents in the treatment and prevention of CDI would be single antibodies that can simultaneously neutralize both TcdA and TcdB as this would be necessary in order to convey full protection against most pathogenic C. difficile strains. By creating tetra-specific binding agents that recognize and bind two epitopes on each of the toxins, the binding and neutralizing activity of the proteins might be strengthened. Therefore, four domain (tetra-specific) $V_HH$ binding agents were generated.

The tetra-specific, tetrameric binding agents can be prepared from any combination of the monomers of Table 1, where the monomers are linked using the flexible linkers of Table 2. These binding agents will range from those having four copies of the same monomer, to those having three copies of the same monomer, to those having two copies of the same monomer, to those having four unique monomers, and variations therein. Sequence variants of the tetramers are included in the invention, having at least 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each tetramer and the sequence variants thereof, as well as complementary strands thereof.

ABAB is a particular binding agent of the invention that comprises four linked $V_HH$ monomers, each of which has binding specificity for a different epitope of TcdA or TcdB. ABAB (sometimes also termed "ABBA" herein and in the figures) is thus a tetra-specific, tetrameric binding agent that consists of four distinct neutralizing $V_HH$ monomers, two against TcdA and two against TcdB. This structural feature allows ABAB to bind simultaneously to two distinct neutralizing epitopes on each toxin. As described below, affinity/avidity and neutralizing activity of ABAB is more than 3-logs higher than human monoclonal antibodies (HuMabs) currently undergoing clinical trials for treatment of CDI.

ABAB binding agent was prepared by linking $V_HH$ monomers AH3, 5D, E3, and AA6 (Table 1) using flexible linkers (Table 2). This binding agent targets conserved, non-overlapping epitopes and has excellent toxin neutralizing activity. In the design of ABAB (FIG. 3), $V_HH$ peptide monomers AH3 and AA6 were separated by placing the 5D between them because AH3 and AA6 bind to GT and TD respectively (FIG. 1), which are spatially distant to each other. This design allowed AH3 and AA6 to bind to TcdA simultaneously.

The complete amino acid sequence comprising ABAB is provided in SEQ ID NO:19; the nucleic acid sequence encoding the protein is provided in SEQ ID NO:20. The present invention thus includes the ABAB binding agent provided in SEQ ID NO:19, as well as sequence variants of the ABAB binding agent having at least 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding the ABAB binding agent (e.g., SEQ ID NO:20) and the sequence variants thereof, as well as complementary strands thereof.

In one variation of the ABAB binding agent, a $His_{(6)}$-tag (HHHHHH; SEQ ID NO:66) was provided at the amino terminus of the protein to aid in purification and an E-tag (GAPVPYPDPLEPR; SEQ ID NO:67) was provided at the carboxy terminus of the protein to aid in detection (see FIG. 3). Because $V_HH$ monomers have a half-life of 2-3 hr, in another variation an albumin-binding peptide (ABP, DICLPRWGCLWD; SEQ ID NO:21) was placed at the carboxyl end of the construct to increase its serum half-life to 10 hr (see FIG. 3).

These binding agents bind to TcdA and/or TcdB with specificity. In certain aspects of the invention, the binding agents exhibit TcdA and/or TcdB neutralizing activity.

For the sake of clarity it can be noted that as used herein, "mono-specific", "bi-specific", "tri-specific", "tetra-specific", etc., mean the particular binding agent binds to 1, 2, 3, 4, etc., different epitopes, respectively. As used herein, "monomeric", "dimeric", "trimeric", "tetrameric", etc., mean that the particular binding agent has 1, 2, 3, 4, etc., separate $V_HH$ peptide monomers that bind to the epitopes, respectively. Thus, a mono-specific, dimeric binding agent would display two $V_HH$ peptide monomers that bind to the same epitope (e.g., a homodimer), and a bi-specific, dimeric binding agent would have two $V_HH$ peptide monomers that bind to two different epitopes (e.g., a heterodimer). A tetra-specific, octameric binding agent has eight $V_HH$ peptide monomers that recognize four different epitopes.

$V_HH$-Fc

It is well known that chimeric Fc-fusion proteins have the potential of increasing the half-life of a protein in vivo. This strategy has been applied in several FDA approved drugs, such as Etanercept. A proof-of principle study has shown that single-chain antibodies can be correctly assembled and expressed by B cells of transgenic mice carrying a mini-Ig construct encoding a dromedary $V_HH$ and the Fc domain of human IgG. Also, a chimeric anti-EGFR/EGFRvIII $V_HH$, EG2-Fc exhibited excellent tumor accumulation in vivo and has pharmacokinetic properties that could improve glioblastoma targeting.

The present invention includes binding agents comprising $V_HH$ peptide monomers joined to antibody Fc domains ($V_HH$-Fc), where the binding agents bind TcdA and/or TcdB. In these Fc domain-based binding agents, one, two, three, four or more of the $V_HH$ peptide monomers are joined to the hinge, $C_H2$ and $C_H3$ regions of the Fc domain of an antibody heavy chain. Thus, the peptide monomers replace the Fab regions of the antibody.

The $V_HH$ peptide monomers may be any of those provided in Table 1 above and include 5D (SEQ ID NO:1), E3 (SEQ ID NO:3), AA6 (SEQ ID NO:5) and AH3 (SEQ ID NO:7) $V_HH$ peptide monomers. Where two or more monomers are linked, the monomers may be linked by flexible peptide linkers, generally comprising between 10 and 20 amino acids. Suitable linkers include those linkers provided in Table 2, such as linker-1 (SEQ ID NO:9), linker-2 (SEQ ID NO:11), and linker-3 (SEQ ID NO:13).

While the $V_HH$-Fc will typically be composed of two identical chains that self-assemble intracellularly after production, the invention also includes $V_HH$-Fc binding agents comprising two different Fc chains. In such circumstances, the sequence of the $V_HH$ monomer(s) alone may differ between the two Fc chains, or the Fc chains themselves may differ in sequence, or both the $V_HH$ monomer(s) and the Fc chains may differ in sequence.

One type of $V_HH$-Fc binding agent is an octameric binding agent comprising an antibody Fc domain and first, second, third and fourth $V_HH$ peptide monomers, where the $V_HH$ peptide monomers have binding specificity for an epitope of *Clostridium difficile* toxin A (TcdA) or toxin B (TcdB), where the first, second, third and fourth $V_HH$ peptide monomers are linked together and joined to amino termini of both antibody Fc domains, and where the antibody Fc domain comprises the hinge, $C_H2$ and $C_H3$ regions of an antibody heavy chain. Because this binding agent has four $V_HH$ peptide monomers, it can be mono-specific (where all of the monomers bind the same epitope), bi-specific (where the monomers bind two different epitopes), tri-specific (where the monomers bind three different epitopes), or tetra-specific (where the monomers bind four different epitopes).

A specific example of a tetra-specific $V_HH$-Fc binding agent is the ABAB-Fc binding agent, a tetra-specific, octameric binding agent comprising an antibody Fc domain and two sets of linked first, second, third and fourth $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first, second, third and fourth $V_HH$ peptide monomers is joined to the amino terminus of the arm, and where the $V_HH$ peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer). ABAB-Fc was found to exhibit specific binding and neutralizing activity.

ABAB-Fc binding agent was prepared by generating an expression vector encoding the $V_HH$ peptide monomers AH3/5D/AA6/E3 (linked in the noted order) joined to a human IgG1 Fc domain. The $V_HH$ peptide monomers were separated by flexible linkers of Table 2. The nucleic acid sequence encoding each chain is provided in SEQ ID NO:23. The amino acid sequence of each chain is provided in SEQ ID NO:22. Upon self-assembly of pairs of the chains after expression, the tetra-specific, octameric binding agent resulted. The invention includes the ABAB-Fc binding agent of SEQ ID NO:22 and sequence variants having at least 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding these sequence variants and complementary strands thereof.

Mono-specific $V_HH$-Fc binding agents (AH3-Fc, 5D-Fc, E3-Fc, AA6-Fc) and bi-specific $V_HH$-Fc binding agents (e.g., AH3/5D-Fc and AA6/E3-Fc) were also made using this Fc-fusion system. With respect to mono-specific binding agents, single $V_HH$ peptide monomers were joined to human IgG1 Fc domains. Upon expression and assembly, pairs of the chains resulted in mono-specific, dimeric binding agents (when the chains were identical) or bi-specific, dimeric binding agents (when the chains were different). With respect to bi-specific binding agents, two linked $V_HH$ peptide monomers ($V_HH$ homo- or hetero-dimers) were joined to human IgG1 Fc domains. Upon expression and assembly, pairs of the chains resulted in bi-specific, tetrameric binding agents (when the chains were identical) or tetra-specific, tetrameric binding agents (when the chains were different). Table 4 provides the sequences for some these binding agents.

TABLE 4

| Name | SEQ ID NO for Amino Acid Seq. | SEQ ID NO for Nucleic Acid Seq. |
| --- | --- | --- |
| 5D-Fc | 24 | 25 |
| E3-Fc | 26 | 27 |
| AA6-Fc | 28 | 29 |
| AH3-Fc | 30 | 31 |
| AH3-5D-Fc | 32 | 33 |
| AA6-E3-Fc | 34 | 35 |

Specific pairings with one monomer include: 5D-Fc+5D-Fc; E3-Fc+E3-Fc; AA6-Fc+AA6-Fc; AH3-Fc+AH3-Fc; 5D-Fc+E3-Fc; 5D-Fc+AA6-Fc; 5D-Fc+AH3-Fc; E3-Fc+AA6-Fc; E3-Fc+AH3-Fc; and AA6-Fc+AH3-Fc. Specific pairings with two monomers include: AH3-5D-Fc+AH3-5D-Fc; AA6-E3-Fc+AA6-E3-Fc; and AH3-5D-Fc+AA6-E3-Fc.

Bi-specific, tetrameric $V_HH$-Fc binding agents were produced comprising an antibody Fc domain and two sets of linked first and second $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first and second $V_HH$ peptide monomers is joined to the amino terminus of the arm, and where the $V_HH$ peptide monomers have binding specificity for an epitope of *Clostridium difficile* toxin A (TcdA) or toxin B (TcdB). This binding agent is termed "bi-specific" as it recognizes two different toxin epitopes. It is termed "tetrameric" as it bears four $V_HH$ peptide monomers (two copies of the first monomer, and two copies of the second monomer). The first and second $V_HH$ peptide monomers may have binding specificity for the same or different epitopes. The $V_HH$ peptide monomers may independently have binding specificity for an epitope in the glucosyltransferase domain, cysteine protease domain, translocation domain or receptor binding domain of TcdA or TcdB.

A specific example of a bi-specific, tetrameric $V_HH$-Fc binding agent comprises the amino acid sequence set forth in SEQ ID NO:32 (AH3/5D-Fc). The invention also includes sequence variants thereof having at least 95% sequence identity, where the sequence variant retains toxin-neutralizing activity. The variant amino acids of the sequence variant may be located in framework regions of the $V_HH$ peptide monomers.

A specific example of a bi-specific, tetrameric $V_HH$-Fc binding agent comprises the amino acid sequence set forth in SEQ ID NO:34 (AA6/E3-Fc). The invention also includes sequence variants thereof having at least 95% sequence identity, where the sequence variant retains toxin-neutralizing activity. The variant amino acids of the sequence variant may be located in framework regions of the $V_HH$ peptide monomers.

The V$_H$H-Fc binding agents bind to TcdA and/or TcdB with specificity. In certain aspects of the invention, the binding agents exhibit TcdA and/or TcdB neutralizing activity.

V$_H$H-IgG

The present invention also includes binding agents comprising V$_H$H peptide monomers joined to more of an antibody that the Fc domain alone. V$_H$H-IgG binding agents comprise one, two, three, four or more of the V$_H$H peptide monomers are joined to the light (kappa or lambda) and heavy chains of an IgG antibody lacking the variable regions of the antibody. Thus, the peptide monomers replace the variable regions of the antibody.

The V$_H$H peptide monomers may be any of those provided in Table 1 above and include 5D (SEQ ID NO:1), E3 (SEQ ID NO:3), AA6 (SEQ ID NO:5) and AH3 (SEQ ID NO:7) V$_H$H peptide monomers. Where two or more monomers are linked, the monomers may be linked by flexible peptide linkers, generally comprising between 10 and 20 amino acids. Suitable linkers include those linkers provided in Table 2, such as linker-1 (SEQ ID NO:9), linker-2 (SEQ ID NO:11), and linker-3 (SEQ ID NO:13).

V$_H$H-IgG binding agents include octameric binding agents comprising an IgG antibody and first, second, third and fourth V$_H$H peptide monomers, wherein the V$_H$H peptide monomers have binding specificity for an epitope of *Clostridium difficile* toxin A (TcdA) or toxin B (TcdB), wherein first and second V$_H$H peptide monomers are linked together and joined to amino termini of both light chains of the antibody, wherein the light chains lack the antibody variable regions, and wherein third and fourth V$_H$H peptide monomers are linked together and joined to amino termini of both heavy chains of the antibody, wherein the heavy chains lack the antibody variable regions. Because this binding agent has four V$_H$H peptide monomers, it can be monospecific (where all of the monomers bind the same epitope), bi-specific (where the monomers bind two different epitopes), tri-specific (where the monomers bind three different epitopes), or tetra-specific (where the monomers bind four different epitopes).

A specific example of a tetra-specific V$_H$H-IgG binding agent is the ABAB-IgG binding agent, a tetra-specific, octameric binding agent comprising an IgG antibody, two sets of linked first and second V$_H$H peptide monomers, and two sets of linked third and fourth V$_H$H peptide monomers, wherein the IgG antibody comprises two arms, each arm comprising a heavy chain lacking a variable region and a light chain lacking a variable region, and each chain having an amino terminus, wherein for each arm of the antibody, one set of linked first and second V$_H$H peptide monomers is joined to the amino terminus of the light chain, and one set of linked third and fourth V$_H$H peptide monomers is joined to the amino terminus of the heavy chain, and wherein the V$_H$H peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight V$_H$H peptide monomers (two copies of the first monomer, two copies of the second monomer, two copies of the third monomer, and two copies of the fourth monomer). In certain aspects, the first, second, third and fourth V$_H$H peptide monomers may each have binding specificity for a different epitope. In certain aspects, two of the V$_H$H peptide monomers may have binding specificity for epitopes of TcdA and two of the V$_H$H peptide monomers may have binding specificity for epitopes of TcdB. In certain aspects, the V$_H$H peptide monomers independently have binding specificity for an epitope in the glucosyltransferase domain, cysteine protease domain, translocation domain or receptor binding domain of TcdA or TcdB.

A specific example of a tetra-specific, octameric ABAB-IgG binding agent comprises a light (kappa) chain having the amino acid sequence set forth in SEQ ID NO:46 (AA6/E3 kappa) or a sequence variant having at least 95% sequence identity thereto, and a heavy chain having the amino acid sequence set forth in SEQ ID NO:44 (AH3/5D heavy) or a sequence variant having at least 95% sequence identity thereto. In this aspect, the sequence variants retain toxin-neutralizing activity. The variant amino acids of the sequence variant may be located in framework regions of the V$_H$H peptide monomers. This binding agent was produced by preparing two separate expression vectors, the first encoding the V$_H$H peptide monomers AH3/5D (linked in the noted order) joined to the human IgG1 antibody heavy chain lacking the variable region and the second encoding the V$_H$H peptide monomers AA6/E3 (linked in the noted order) joined to the human IgG1 antibody light (kappa) chain lacking the variable region. The nucleotide sequence encoding the AA6/E3-IgG1 light (kappa) chain is provided in SEQ ID NO:47. The nucleotide sequence encoding the AH3/5D-IgG1 heavy chain is provided in SEQ ID NO:45. The invention includes sequence variants of ABAB-IgG having at least 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding these sequence variants and complementary strands thereof.

Bi-specific or tetra-specific, tetrameric IgG binding agents are included in the invention. Such binding agents comprise an IgG antibody and first, second, third and fourth V$_H$H peptide monomers, wherein the IgG antibody comprises two arms, each arm comprising a heavy chain lacking a variable region and a light chain lacking a variable region, and each chain having an amino terminus, wherein for a first arm of the antibody, the first V$_H$H peptide monomer is joined to the amino terminus of the light chain, and the second V$_H$H peptide monomer is joined to the amino terminus of the heavy chain, wherein for a second arm of the antibody, the third V$_H$H peptide monomer is joined to the amino terminus of the light chain, and the fourth V$_H$H peptide monomer is joined to the amino terminus of the heavy chain, and where the V$_H$H peptide monomers have binding specificity for an epitope of *Clostridium difficile* toxin A (TcdA) or toxin B (TcdB). When the binding agent is "tetra-specific", it recognizes four different toxin epitopes; when "bi-specific" it recognizes two different toxin epitopes. The binding agents "tetrameric" as they bear four V$_H$H peptide monomers (when bi-specific, the first and second monomer have the same sequence and bind the same epitope, and the third and fourth monomers have the same sequence and bind the same epitope; when tetra-specific, each of the monomers has a different sequence and binds a different epitope).

When the binding agent is bi-specific, the first and third monomers have binding specificity for different epitopes, the first and second monomers have identical amino acid sequences, and the third and fourth monomers have identical amino acid sequences. In certain aspects, one of the V$_H$H peptide monomers has binding specificity for an epitope of TcdA and one of the V$_H$H peptide monomers has binding specificity for an epitope of TcdB.

When the binding agent is tetra-specific, each of the V$_H$H peptide monomers has binding specificity for a different epitope. In certain aspects, two of the $V_HH$ peptide monomers have binding specificity for epitopes of TcdA and two of the $V_HH$ peptide monomers have binding specificity for epitopes of TcdB.

In certain aspects, each of the $V_HH$ peptide monomers has binding specificity for epitopes of TcdA. In other aspects, each of the $V_HH$ peptide monomers has binding specificity for epitopes of TcdB.

In certain aspects, the $V_HH$ peptide monomers independently have binding specificity for an epitope in the glucosyltransferase domain, cysteine protease domain, translocation domain or receptor binding domain of TcdA or TcdB.

A specific example of a bi-specific, tetrameric IgG binding agent comprises a light (kappa) chain having the amino acid sequence set forth in SEQ ID NO:40 (AA6 kappa) and a heavy chain having the amino acid sequence set forth in SEQ ID NO:36 (AH3 heavy). The invention also includes sequence variants thereof having at least 95% sequence identity, where the sequence variant retains toxin neutralizing activity. The variant amino acids of the sequence variant may be located in framework regions of the $V_HH$ peptide monomers.

Another specific example of a bi-specific, tetrameric IgG binding agent comprises a light (kappa) chain having the amino acid sequence set forth in SEQ ID NO:42 (E3 kappa) and a heavy chain having the amino acid sequence set forth in SEQ ID NO:38 (5D heavy). The invention also includes sequence variants thereof having at least 95% sequence identity, where the sequence variant retains toxin neutralizing activity. The variant amino acids of the sequence variant may be located in framework regions of the $V_HH$ peptide monomers.

Table 5 provides the sequences used to generate bi-specific $V_HH$-IgG binding agents. Other suitable pairings include (i) 5D-IgG1-heavy chain+AA6-light (kappa or lambda) chain, and (ii) AH3-IgG1-heavy chain+E3-light (kappa or lambda) chain.

TABLE 5

| Name | SEQ ID NO for Amino Acid Seq. | SEQ ID NO for Nucleic Acid Seq. |
| --- | --- | --- |
| AH3-IgG1-heavy chain | 36 | 37 |
| 5D-IgG1-heavy chain | 38 | 39 |
| AA6-IgG1-kappa chain | 40 | 41 |
| E3-IgG1-kappa chain | 42 | 43 |

However, the present invention includes IgG1 heavy chains joined to any of AH3, 5D, AA6 and E3, and IgG1 light (kappa or lambda) chains joined to any of AH3, 5D, AA6 and E3. Further, all possible combinations of the heavy and light (kappa or lambda) chains are encompassed herein.

Humanized Binding Agents

Due to their small size and the high degree of identity of their framework to the human $V_H$ framework of family III, $V_HH$ peptide monomers are expected to exhibit low immunogenicity when administered to humans. While the systemic application of small monovalent $V_HH$ monomers seems to induce little, if any, neutralizing antibody responses, protein immunogenicity generally increases with size and complexity. Two major hurdles for repeated and/or long-term in vivo use of $V_HH$ monomers are their likely short half-life and potential immunogenicity. To increase the valence and circulating half-life, $V_HH$ monomers can be fused with human IgG and Fc domains as discussed herein. To address possible immunogenicity, the $V_HH$ monomers can be humanized as needed without compromising their expression level, affinity, solubility, and stability. These strategies should result in good expression, stability, and solubility of humanized $V_HH$ monomers (h$V_HH$ monomers), while retaining the antigen specificity and affinity of the loop donor $V_HH$.

h$V_HH$ monomers that gain highest identity to human $V_H$ gene(s) and possess the highest binding/neutralizing activity are selected, after which they are transformed into the $V_HH$-Fc and $V_HH$-IgG constructs to generate fully humanized binding agents, such as fully humanized ABAB-IgG and ABAB-Fc binding agents. The protein sequences of these humanized binding agents can be essentially identical to that of a human antibody variant, despite the non-human origin of some of its CDR segments that are responsible for the ability of the antibody to bind to its target antigen. Therefore, this strategy decreases the chance for potential immunogenicity in vivo and thus increase their safety and half-life in vivo.

The binding agents of the present invention thus encompasses humanized versions of each of the binding agents defined herein, comprising h$V_HH$ peptide monomers.

Antibody Fragments

The binding agents of the invention include epitope binding fragments of each of the $V_HH$-Fc and $V_HH$-IgG binding agents defined herein. Because the $V_HH$-Fc and $V_HH$-IgG binding agents are comparable in structure to human IgG antibodies, where the variable regions are replace by the $V_HH$ monomers, terms for human antibody fragments are also applicable to the such binding agents. The fragments include, but are not limited to, Fab fragments, F(ab')$_2$ fragments, single chain Fv (scFv) antibodies, and fragments produced by an Fab expression library, as well as bi-specific antibody and triple-specific antibodies.

The $V_HH$-Fc and $V_HH$-IgG binding agents of the invention include fully human, humanized, and chimeric binding agents. The binding agents may be monoclonal or polyclonal. Further, the binding agents may be recombinant binding agents.

The binding agents may be produced in any species of animal, though preferably from a mammal such as a human, simian, mouse, rat, rabbit, guinea pig, horse, cow, sheep, goat, pig, dog or cat. For example, the binding agents can be human or humanized, or any binding agent preparation suitable for administration to a human.

Polynucleotide, Expression Vectors, Host Cells and Method of Making

The invention includes polynucleotides comprising nucleotide sequences encoding each the binding agents provided herein, as well as complementary strands thereof.

The invention also includes expression vectors comprising the polynucleotides, and host cells comprising the expression vectors. Suitable expression vectors include, e.g., pcDNA3.1 and pSec-His. Suitable host cells include, e.g., Chinese hamster ovary cells (CHO cells) and human embryonic kidney cells 293 (HEK 293 cells).

The invention further includes methods of producing the binding agents defined herein, comprising culturing the host cells under conditions promoting expression of the binding agents encoded by the expression vectors, and recovering the binding agents from the cell cultures.

Methods of Treatment and Prevention

The binding agents of the invention can be used in methods of treating or preventing a disease symptom induced by C. difficile in a subject. These methods generally comprise administering a therapeutically-effective amount of one or more binding agents as defined herein to a subject having C. difficile infection or a risk of developing C. difficile infection.

The binding agents of the invention can also be used in of neutralizing C. difficile toxin TcdA and/or TcdB in a subject infected by C. difficile. These methods generally comprise administering a therapeutically-effective amount of one or more binding agents as defined herein to a subject having C. difficile infection.

The binding agents of the invention can further be used in methods of treating C. difficile infection in a subject. These methods generally comprise administering a therapeutically-effective amount of one or more of the binding agents as defined herein to a subject having C. difficile infection. These same methods can be used to treat CDI, as defined herein.

The binding agents can also be used in immunoprophylaxis in order to prevent immediate CDI threats. In addition, passive immunoprophylaxis can be used to prevent both immediate and longer-term CDI threats. Each approach has its own particular advantages and is suitable to target a particular high-risk population. These methods generally comprises administering a therapeutically-effective amount of one or more of the binding agent as defined herein to a subject a risk of developing C. difficile infection.

Each of the methods of the invention may include administration of the one or more binding agents in a pharmaceutical formulation comprising the binding agents and a pharmaceutically acceptable carrier or diluent.

As used herein, the terms "treat", "treating", and "treatment" have their ordinary and customary meanings, and include one or more of: blocking, ameliorating, or decreasing in severity and/or frequency a symptom of a C. difficile infection or a C. difficile-related disease in a subject; and/or partly or fully inhibiting the biological activity and/or promoting the immunologic clearance of C. difficile TcdA and/or TcdB in a subject infected with C. difficile; and/or growth, division, spread, or proliferation of C. difficile cells or a C. difficile infection in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

As used herein, the terms "prevent", "preventing" and "prevention" have their ordinary and customary meanings, and include one or more of, stopping, averting, avoiding, alleviating or blocking C. difficile from colonizing, developing or progressing in a subject; and/or partly or fully inhibiting the biological activity and/or toxic effects of TcdA and/or TcdB in a subject infected with C. difficile; and/or stopping, averting, avoiding, alleviating or blocking the growth, division, spread, or proliferation of bacterial cells or bacterial infection in a subject. Prevention means stopping by at least about 95% versus a subject to which the prevention has not been administered. Preferably, the stopping is about 100%, about 99%, about 98%, about 97%, about 96% or about 95%. The results of the prevention may continue for a period of days (such as 1, 2, 3, 4, 5, 6 or 7 days), weeks (such as 1, 2, 3 or 4 weeks) or months (such as 1, 2, 3, 4, 5, 6 or more months).

The method of treating and preventing provided herein can be supplemented by also administering a therapeutically-effective amount of an antibiotic to the subject. Preferably, the antibiotic will have antibacterial activity against C. difficile.

Pharmaceutical Formulations

While the binding agents may be administered directly to a subject, the methods of the present invention are preferably based on the administration of a pharmaceutical formulation comprising one or more binding agents and a pharmaceutically acceptable carrier or diluent. Thus, the invention includes pharmaceutical formulations comprising one or more of the binding agents defined herein and a pharmaceutically acceptable carrier or diluent.

Pharmaceutically acceptable carriers and diluents are commonly known and will vary depending on the particular binding agent being administered and the mode of administration. Examples of generally used carriers and diluents include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising binding agents will typically have been prepared and cultured in the absence of any non-human components, such as animal serum (e.g., bovine serum albumin).

Pharmaceutical formulations comprising one or more binding agents may be administered to a subject using modes and techniques known to the skilled artisan. Characteristic of CDI disease may make it more amenable to treatment and prevention using colonic delivery of therapeutic agents, i.e., targeted delivery of binding agents to the lower GI tract, e.g., the large intestine or colon. Other modes of delivery include, but are not limited to, oral, anal, via intravenous injection or aerosol administration. Other modes include, without limitation, intradermal, subcutaneous (s.c., s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

Depending on the means of administration, the dosage may be administered all at once, such as with an oral formulation in a capsule or liquid, or slowly over a period of time, such as with an intramuscular or intravenous administration.

The amount of binding agents, alone or in a pharmaceutical formulation, administered to a subject is an amount effective for the treatment or prevention of infection. Thus, therapeutically effective amounts are administered to subjects when the methods of the present invention are practiced. In general, between about 1 ug/kg and about 1000 mg/kg of the binding agent per body weight of the subject is administered. Suitable ranges also include between about 50 ug/kg and about 500 mg/kg, and between about 10 ug/kg and about 100 mg/kg. However, the amount of binding agent administered to a subject will vary between wide limits, depending upon the location, source, extent and severity of the infection, the age and condition of the subject to be treated, etc. A physician will ultimately determine appropriate dosages to be used.

Administration frequencies of the binding agents and pharmaceutical formulations comprising the binding agents will vary depending on factors that include the location of the bacterial infection, the particulars of the infection to be treated or prevented, and the mode of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment or prevention will be based on location and severity of the infection being treated or the relative risk of contracting the infection, and will be best determined by the attending physician. However, continuation of treatment is contemplated to last for a number of days, weeks, or months.

In each embodiment and aspect of the invention, the subject is a human, a non-human primate, bird, horse, cow, goat, sheep, a companion animal, such as a dog, cat or rodent, or other mammal. The subjects to which the methods of the present invention can be applied include subjects having an underlying disease or condition that makes them more susceptible to *C. difficile* infections.

The invention also provides a kit comprising one or more containers filled with one or more binding agents or pharmaceutical formulations comprising binding agents. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

IV. Examples $V_HH$ Monomer and Heterodimer Binding Agents

An efficient platform to screen single domain (monomeric), mono-specific $V_HH$ peptide monomers against specific domains of toxins TcdA and TcdB was established. Using highly immunogenic atoxic holotoxins for immunization, and bioactive chimeric toxins (with normal domain functions) for screening, panels of $V_HH$ monomers binding to different domains of TcdA or TcdB were prepared. A majority of these $V_HH$ monomers possessed potent neutralizing activity and their binding to specific domains was determined (FIG. 1). The atoxic holotoxins have point mutations at their enzymatic glucosyltransferase domains as described previously (Wang et al., 2012). The bioactive chimeric toxins were created by switching the functional domains between TcdA and TcdB, which was also described previously (Wang, et al., 2012).

Several of the $V_HH$ monomers bind to highly conserved TcdA/TcdB epitopes. For example, $V_HH$ E3 binds to the Rho GTPase binding site and blocks glucosylation; $V_HH$ AH3 binds to the GT domain of the toxin; $V_HH$ 7F binds to cysteine protease cleavage sites and blocks GT domain cleavage and release. Some $V_HH$ monomers have potent neutralizing activity capable of blocking toxin cytotoxic activity at nM concentrations (See Table 1; FIGS. 2A and B).

To enhance the binding activity, two domain (dimeric), bi-specific $V_HH$ heterodimers were created (Table 3; FIG. 2C), allowing a single protein to target two distinctive epitopes of the toxins. These bi-specific $V_HH$ heterodimers possessed substantially enhanced neutralizing activities compared with equimolar mixtures of the same two $V_HH$ monomers (FIG. 2D). Heterodimers 5D/E3 and AH3/AA6 were found to fully protect mice from lethal systemic TcdB or TcdA challenge respectively, whereas mixed 5D and E3, or AA6 alone were only partially protective (FIGS. 2E and F).

The $V_HH$ monomers comprising the heterodimers were linked using a flexible linker selected from SEQ ID NOs: 9-13 (Table 2).

ABAB Binding Agent

A four domain (tetrameric), tetra-specific $V_HH$ binding agent termed ABAB was generated by linking $V_HH$ monomers AH3, 5D, E3, and AA6. This tetra-specific, tetrameric binding agent targets conserved, non-overlapping epitopes and it has excellent toxin neutralizing activity. In the design of ABAB (FIG. 3), $V_HH$ peptide monomers AH3 and AA6 were separated by placing the 5D monomers between them because AH3 and AA6 bind to GT and TD respectively (FIG. 1), which are spatially distant to each other. This design allowed AH3 and AA6 to bind to TcdA simultaneously.

Figure 3:
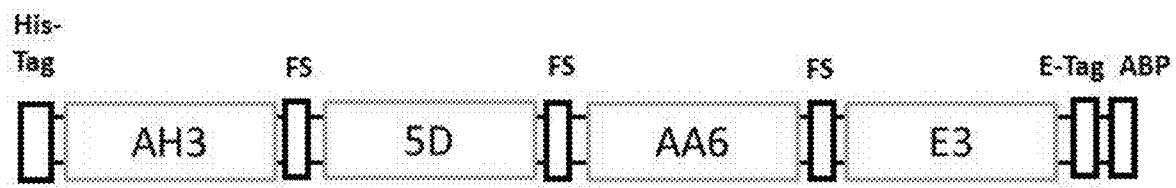
FIG. 3. Diagram of ABAB. His-tag and E-tag are epitope tags for purification and detection, respectively. FS: flexible linker; ABP: albumin binding peptide.

In the construction of the ABAB binding agent, flexible linkers were placed between the $V_HH$ monomers (see FIG. 3). The complete nucleic acid sequence encoding ABAB is provided in SEQ ID NO:20; the amino acid sequence of the protein is provided in SEQ ID NO:19.

In certain variants, a $His_{(6)}$-tag was provided at the amino terminus of the protein to aid in purification, an E-tag was provided at the carboxy terminus of the protein to aid in detection, and/or an albumin-binding peptide (ABP, DICLPRWGCLWD; SEQ ID NO:21) was placed at the carboxyl end of the construct to increase serum half-life of the protein (See FIG. 3).

ABAB was found to exhibit substantial enhanced binding affinity (Table 6) and neutralizing activity (Table 7) over the individual monomers. In Table 7, Vero cells were exposed to 5 ng/ml of TcdA in the presence of serially diluted AA6, AH3, ABAB or Merck anti-TcdA HuMab (Lowy et al., 2010). The minimal doses of antibodies protecting cells from TcdA-induced cell rounding are shown.

TABLE 6

|  | $V_H$Hs | $K_{on}$ (Ms$^{-1}$) | $K_{off}$ (s$^{-1}$) | $K_D$ (nM) |
|---|---|---|---|---|
| TcdA | AH3 | $2.20 \times 10^4$ | $7.10 \times 10^{-4}$ | 32.0 |
|  | AA6 | $3.52 \times 10^4$ | $6.92 \times 10^{-4}$ | 19.7 |
|  | ABAB | $6.96 \times 10^5$ | $1.21 \times 10^{-6}$ | 0.002 |
| TcdB | 5D | $1.52 \times 10^6$ | $9.94 \times 10^{-4}$ | 0.65 |
|  | E3 | $2.95 \times 10^6$ | $9.4 \times 10^{-5}$ | 0.03 |
|  | ABAB | $1.79 \times 10^6$ | $3.57 \times 10^{-6}$ | 0.002 |

TABLE 7

| AA6 | AH3 | ABAB | Merck Anti-TcdA HuMab |
|---|---|---|---|
| 8 nM | 8 nM | 0.25 nM | >10 nM |

ABAB was also found to compete with all four individual $V_HH$ peptide monomers in a competition ELISA and can simultaneously bind to both TcdA and TcdB as determined by sandwich ELISA. Furthermore, ABAB is broadly reactive, capable of neutralizing toxins from the 13 different *C. difficile* strains that represent most of the current epidemic strains.

Figure 4A:
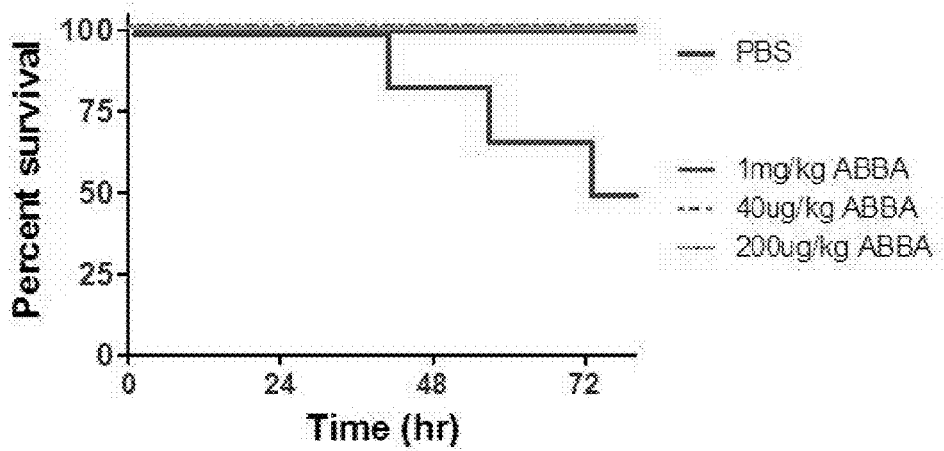
FIGS. 4A-4B. ABAB is highly potent in protecting mice from *C. difficile* spore (FIG. 4A) and toxin (FIG. 4B) challenge. MK HuMabs: a mixture of Merck anti-TcdA and anti-TcdB human monoclonal antibodies that are undergoing clinical trials.
Figure 4B:
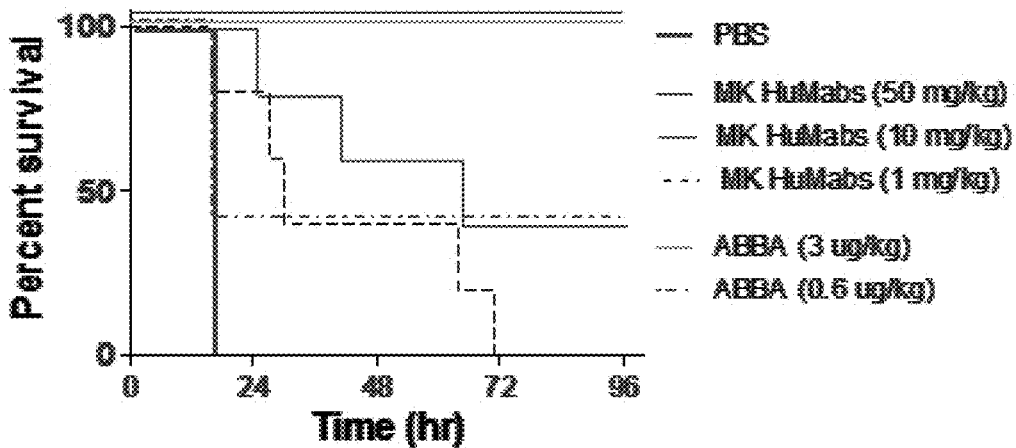

Since ABAB shows high potency in binding to and neutralizing both toxins, its efficacy in treating fulminant CDI was evaluated. A single injection with as low as 40 μg/kg of ABAB one-day post *C. difficile* spore challenge reversed fulminant CDI in mice. None of the ABAB-treated mice died whereas 50% of control mice became moribund by 3 days post-infection (FIG. 4, left panel). ABAB is 4-log more potent in preventing mortality after systemic challenge with TcdA and TcdB than the Merck HuMabs (FIG. 4, right panel) (Lowy et al., 2010). Thus, ABAB possesses extraordinary in vivo efficacy against *C. difficile* toxins and spore challenge.

Animal and human studies demonstrated that passively administered antitoxin antibodies provide protection against CDI. The initial studies here also showed that antitoxin polysera protected mice from primary CDI (FIG. 5) and recurrent/relapse CDI. These findings and results from FIG. 4 supported the hypothesis and provided the rationale for development of a parenteral ABAB immunization strategy for preventing CDI. To achieve the goal of optimizing ABAB for systemic delivery, chimeric and humanized ABAB were generated as illustrated in FIG. 6, i.e., $V_HH$-Fc and $V_HH$-IgG binding agents as well as the humanized proteins h$V_HH$-Fc and h$V_HH$-IgG, after which leading proteins were evaluated for in vivo neutralizing activity and protection in animal models. Details regarding the preparation and testing of the additional binding agents are provided in the following paragraphs.

ABAB-Fc

ABAB-Fc binding agent was prepared by generating an expression vector encoding the $V_HH$ peptide monomers AH3/5D/AA6/E3 (linked in the noted order) joined to a human IgG1 Fc domain. The $V_HH$ peptide monomers were separated by flexible linkers of Table 2. The nucleic acid sequence encoding the protein is provided in SEQ ID NO:23. ABAB-Fc was expressed and purified from stable transfected HEK293 cell line culture supernatant using protein A beads (FIG. 7) under conditions permitting disulfide bond formation and bi-valent molecule production. The expression levels were about 20 mg/L of culture supernatant. ABAB-Fc is fully functional in binding and neutralizing both TcdA and TcdB. The amino acid sequence of ABAB-Fc is provided in SEQ ID NO:22.

Mono-specific $V_HH$-Fc binding agents (AH3-Fc, 5D-Fc, E3-Fc, AA6-Fc) and bi-specific $V_HH$-Fc binding agents (AH3/5D-Fc) and AA6/E3-Fc) were also made using this Fc-fusion system. Table 4 above provides the sequences for these additional binding agents.

ABAB-IgG

As illustrated in FIG. 6, bi-specific $V_HH$-IgG (AH3/5D-IgG and E3/AA6-IgG) can be generated by fusing monomers with human IgG heavy and light (kappa or lambda) chains separately. Tetra-specific $V_HH$-IgG (ABAB-IgG) binding agents can be generated by fusing dimers with human IgG heavy and light chains separately. Co-transfecting the heavy and light chain constructs generates the AH3/5D-IgG, E3/AA6-IgG and ABAB-IgG chimeric proteins. The separation of two $V_HH$s into heavy and light chains likely improves the yield and stability of bi-specific and tetra-specific $V_HH$ chimeric proteins. This allows determination of whether $V_HH$-human IgG chimeric antibody helps the stability and efficacy of ABAB in vivo. Similarly, further improvement of in vivo half-life of ABAB-IgG can also be tested in ABAB-IgG variants with enhanced binding affinity to FcRn receptor.

Bi-specific (AH3/5D-IgG1 and E3/AA6-IgG1) and tetra-specific (ABAB-IgG1) IgG1 binding agents were prepared by co-transfecting expression vectors encoding the heavy and light (kappa) chain of each binding agent. The $V_HH$ peptide monomers were separated by flexible linkers of Table 2.

Bi-specific, tetrameric $V_HH$-IgG1 binding agents were produced by preparing two separate expression vectors, the first encoding a $V_HH$ peptide monomer joined to the human IgG1 antibody heavy chain (CH1-Hinge-CH2-CH3) lacking the heavy chain variable region and the second encoding a $V_HH$ peptide monomer joined to the human IgG1 antibody light (kappa) chain (CK) lacking the light chain variable region. These binding agents are bi-specific and tetrameric in that each light chain of the resulting binding agent is linked to a first $V_HH$ monomer and each heavy chain of the resulting binding agent is linked to a second $V_HH$ monomer. Table 5 above provides the sequences for these additional binding agents. Suitable pairings include (i) AH3-IgG1-heavy chain+AA6-light (kappa or lambda) chain, (ii) 5D-IgG1-heavy chain+E3-light (kappa or lambda) chain, (iii) 5D-IgG1-heavy chain+AA6-light (kappa or lambda) chain, and (iv) AH3-IgG1-heavy chain+E3-light (kappa or lambda) chain.

Tetra-specific, octameric ABAB-IgG binding agents were prepared. These binding agents are tetra-specific and octameric in that each light (kappa or lambda) chain of the resulting binding agent is joined to two (a first and second) linked $V_HH$ monomers and each heavy chain of the resulting binding agent is joined to a two (a third and fourth) linked $V_HH$ monomer, where the first, second, third and fourth monomers binds to a different epitope.

A particular tetra-specific, octameric ABAB-IgG (FIG. 8) binding agent was produced by preparing two separate expression vectors, the first encoding the $V_HH$ peptide monomers AH3/5D (linked in the noted order) joined to the human IgG1 antibody heavy chain (CH1-Hinge-CH2-CH3) lacking the heavy chain variable region and the second encoding the $V_HH$ peptide monomers AA6/E3 (linked in the noted order) joined to the human IgG1 antibody light (kappa) chain (CK) lacking the light chain variable region. The nucleotide sequence encoding the AH3/5D-IgG1 heavy chain is provided in SEQ ID NO:45; the amino acid sequence is provided in SEQ ID NO:44. The nucleotide sequence encoding the AA6/E3-IgG1 kappa chain is provided in SEQ ID NO:47; the amino acid sequence is provided in SEQ ID NO:46.

The bi-specific (AH3/5D-IgG1 and E3/AA6-IgG1) and tetra-specific (ABAB-IgG1) IgG1 binding agents were expressed and purified from stable transfected HEK293 cell line culture supernatant using protein A beads (see FIG. 9 for ABAB-IgG1) under conditions permitting disulfide bond formation and bi-valent molecule production. SDS-PAGE shows more than 90% purity of the purified ABAB-IgG1 with total molecular weight (light and heavy chains together) around 218 KDa on non-reduced gel (FIG. 10). The molecular weight of heavy chain is 68 KDa and light chain is 41 KDa showed on reduced gel.

The binding of ABAB-IgG1 to TcdA and TcdB was determined. FIGS. 11A-11B illustrate the comparison of binding ABAB-IgG1 to both toxins with the individual components (AH3, AA6, E3, and 5D). FIG. 11A shows the results of experiments where plates were coated with 1 ug/ml TcdA (TxA). Serially diluted ABAB-IgG was added in concentrations of 0, 0.64, 3.2, 16, 80, 400 and 2,000 ng/ml. The plates were washed and Merck Ab (anti-TcdA), Fc-ABBA (ABAB-Fc), Habab (ABAB-IgG), and $V_HH$ anti-TcdB monomers AA6 and AH3 were added in the indicated amounts (ng/ml). Appropriate labeled antibodies were used for detection. FIG. 11B shows the results of experiments where plates were coated with 1 ug/ml TcdB (TxB). Serially diluted ABAB-IgG was added in concentrations of 0, 0.64, 3.2, 16, 80 and 400 ng/ml. The plates were washed and Merck Ab (Anti-TcdB), Fc-abba (ABAB-Fc), Habab (ABAB-IgG), and $V_HH$ anti-TcdB monomers E3 and 5D were added in the indicated amounts (ng/ml). Appropriate labeled antibodies were used for detection.

As expected, the tetra-specific antibody can bind to TcdA and TcdB simultaneously as determined by sandwich ELISA (FIGS. 12A-12B). In a first set of experiments, plates were coated with 1 ug/ml TcdA (TxA). Serially diluted ABAB-IgG (Habab) was added in concentrations of 0, 1.6, 8, 40, 200 and 1000 ng/ml. The plates were washed and the following amounts of TcdB were added: 1.6, 8, 40, 200, and 1000 ng/ml. Mouse anti-TxB antibodies (500×) and goat anti-mouse-IgG-HRP (3000×) antibodies were used for detection. The results provided in FIG. 12A show that TxB is detected by coating TxA, suggesting IgG-ABAB binds to TxA/B simultaneously. In a second set of experiments, plates were coated with 1 ug/ml TcdB (TxB). Serially diluted ABAB-IgG (Habab) was added in concentrations of 0, 1.6, 8, 40, 200 and 1000 ng/ml. The plates were washed and the following amounts of TcdA were added: 1.6, 8, 40, 200, and 1000 ng/ml. Mouse anti-TxA antibodies (500×) and goat anti-mouse-IgG-HRP (3000×) antibodies were used for detection. The results provided in FIG. 12B show that TxA is detected by coating TxB, again suggesting IgG-ABAB binds to TxA/B simultaneously.

The neutralizing activities of ABAB-IgG1 against cytopathic effects of the toxins on cultured cells were also examined. TcdA (100 ng/ml, FIG. 13A) was mixed with serially diluted Merck anti-TcdA human monoclonal antibody, ABAB-IgG1 (Hababa), and $V_HH$ anti-TcdA monomers AA6 and AH3 before adding to Vero cell monolayers in 100 ul culture medium and incubated at 37° C. for 24 hours. The results provided in FIG. 13A show that ABAB-IgG1 is at least 1000-fold more potent than Merck antibodies in neutralizing TcdA. In similar experiments, TcdB (10 pg/ml, FIG. 13B) was mixed with serially diluted Merck anti-TcdB human monoclonal antibody, ABAB-IgG1 (Hababa), and $V_HH$ anti-TcdB monomers E3 and 5D before adding to Vero cell monolayers in 100 ul culture medium and incubated at 37° C. for 24 hours. The results provided in FIG. 13B show that ABAB-IgG1 is at least 1000-fold more potent than Merck antibodies in neutralizing TcdB.

The in vivo neutralizing activities of ABAB-IgG1 were studied in a mouse model of CDI, the results of which are shown in FIG. 14. Mice were challenged with lethal dose of a mixed TcdA and TcdB (25 ng each toxin per mouse) and 4 hour later, ABAB-IgG (10, 30 or 100 ug/kg), a mixture of Merck anti-toxin A and anti-toxin B antibodies (10 mg/kg) or PBS was administered to the mice. The results demonstrate that the neutralizing activity of ABAB-IgG was much greater than the Merck antibody, and at lower concentrations.

Animal Testing of ABAB-IgG

The ABAB-IgG1 binding agent was tested in both prophylactic treatment and re-challenge survival assays. FIG. 15 provides the experimental design of both studies. 6-8 week old female C57 mice were used, and the conditions included PBS: 10 ml/kg, i.p., n=14; ABAB-IgG: 200 ug/kg, i.p., n=10; ABAB-IgG: 1 mg/kg, i.p., n=10; ABAB-IgG: 5 mg/kg, i.p., n=10.

The table in FIG. 16 provides a summary of the results seen with prophylactic treatment of mice against *C. difficile* spores. ABAB-IgG or PBS was administered one day prior to administrating of *C. difficile* spores. As can be seen, ABAB-IgG showed dose-related prophylactic protection against CDI, where 5 mg/kg showed complete protection on all the parameters examined and 200 ug/kg was found to be more potent than 200 ug/kg of bi-specific $V_HH$ fusion antibody ABA (Yang et al., 2014).

The table in FIG. 17 provides a summary of the results seen with re-challenge of mice against *C. difficile* spores. ABAB-IgG or PBS was administered 15 days prior to administrating of *C. difficile* spores. As can be seen, one dose of ABAB-IgG showed some protection against the CDI caused by re-challenge of spores, but the protection was much less efficient compared to that during the primary challenge. This may be due to the drop of the antibody level with time and the generation of antibody in the PBS group following primary challenge.

Expression, Purification and Evaluation of Binding Agents

Figure 2:
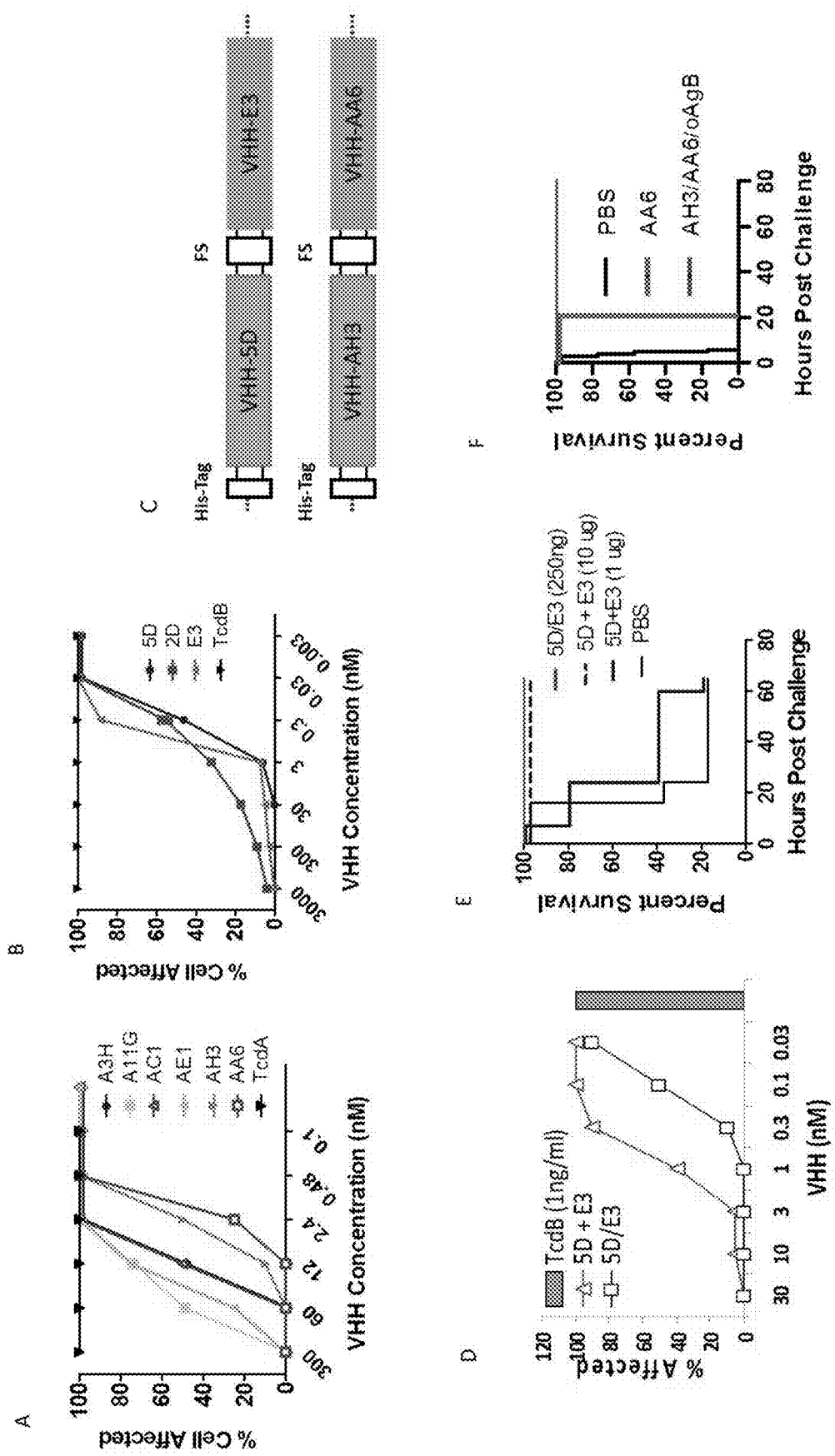
FIG. 2. Monomeric or dimeric $V_HH$s possess potent neutralizing activity. $V_HH$s block cell rounding induced by TcdA (FIG. 2A) or TcdB (FIG. 2B) at nM concentrations.

A variety of selection criteria is used to select the binding agents generated in the experiments described in the approaches herein. First, each of the constructs defined herein can be used in transient transfections of 293T cells for making small-scale recombinant proteins by Protein A affinity chromatography. The production yield of each construct can be determined by quantitative ELISA. Second, binding activity of recombinant proteins can be screened using ELISA and surface plasmon resonance (SPR) to select constructs that preserve their original binding activities against the toxins. Third, the proteins are evaluated for neutralizing activity in in vitro assays (FIG. 2).

Accumulating observations indicate that polyreactivity and/or autoreactivity of in vivo recombinant binding agents are potential issues related to their in vivo safety and half-life. The application of the selected ABAB binding agents as a systemic binding agent for preventing primary acute CDI likely requires that the chimeric and humanized ABAB proteins are limited in polyreactivity and/or autoreactivity. Progress in protein proteomics has made it possible to screen for polyreactivity and autoreactivity of recombinant antibodies in vitro, which is a great tool for surrogate therapeutic antibodies. Therefore, selected humanized binding agents with good yield, high binding affinity, and potent neutralizing activity can be further tested for potential polyreactivity and autoreactivity using the auto-antigen microarray test and ProtoArray protein microarrays (Invitrogen).

From the above in vitro assays, candidate ABAB-Fc and ABAB-IgG binding agents can be evaluated for their in vivo toxicity, serum half-life, and immunogenicity.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

Corbett, J. C. W.; Connah, M.; Mattison, K., Laser doppler electrophoresis using a diffusion barrier. U.S. Pat. No. 8,702,942 (2014).

Jachimska, B.; Wasilewska, M.; Adamczyk, Z., Characterization of globular protein solutions by dynamic light scattering, electrophoretic mobility, and viscosity measurements. *Langmuir* 24 (13), 6866-6872 (2008).

Lowy, I., et al. Treatment with monoclonal antibodies against *Clostridium difficile* toxins. *N Engl J Med* 362, 197-205 (2010).

Perdana, J.; Fox, M. B.; Schutyser, M. A. I.; Boom, R. M., Mimicking Spray Drying by Drying of Single Droplets Deposited on a Flat Surface. *Food Bioprocess Tech* 6 (4), 964-977 (2013).

Wang, H., et al. A chimeric toxin vaccine protects against primary and recurrent *Clostridium difficile* infection. *Infect Immun* 80, 2678-2688 (2012).

Yang, Z., et al. A novel multivalent, single-domain antibody targeting TcdA and TcdB prevents fulminant *Clostridium difficile* infection in mice. *J Infect Dis.* 210(6), 964-72 (2014).

What is claimed is:

1. A tetra-specific, octameric binding agent comprising:
   (a) an IgG antibody, two sets of linked first and second VHH peptide monomers, and two sets of linked third and fourth VHH peptide monomers,
   wherein the IgG antibody comprises two arms, each arm comprising a heavy chain lacking a variable region and a light chain lacking a variable region, and each chain having an amino terminus,
   wherein for each arm of the antibody, one set of linked first and second VHH peptide monomers is joined to the amino terminus of the light chain, and one set of linked third and fourth VHH peptide monomers is joined to the amino terminus of the heavy chain, and wherein the VHH peptide monomers have binding specificity for an epitope of *Clostridium difficile* toxin A (TcdA) or toxin B (TcdB); or
   (b) an antibody Fc domain and two sets of linked first, second, third and fourth VHH peptide monomers,
   wherein the antibody Fc domain comprises two arms, each arm comprising hinge, $C_H2$ and $C_H3$ regions of an antibody heavy chain, and each arm having an amino terminus,
   wherein for each arm of the Fc domain, one set of linked first, second, third and fourth $V_HH$ peptide monomers is joined to the amino terminus of the arm, and
   wherein the $V_HH$ peptide monomers have binding specificity for an epitope of *C. difficile* toxin A (TcdA) or toxin B (TcdB);
   wherein for the binding agents of (a) and (b), the $V_HH$ peptide monomers are (i) the 5D $V_HH$ monomer (SEQ ID NO: 1), (ii) the E3 $V_HH$ monomer (SEQ ID NO:3), (iii) the AA6 $V_HH$ monomer (SEQ ID NO:5), and (iv) the AH3 $V_HH$ monomer (SEQ ID NO:7);
   wherein for the binding agent of (a), the light chain of the binding agent comprises the amino acid sequence set forth in SEQ ID NO:46, and wherein the heavy chain of the binding agent comprises the amino acid sequence set forth in SEQ ID NO:44; and
   wherein for the binding agent of (b), the binding agent comprises the amino acid sequence set forth in SEQ ID NO:22.

2. The binding agent of claim 1, wherein the first, second, third and fourth $V_HH$ peptide monomers each has binding specificity for a different epitope.

3. The binding agent of claim 1, wherein two of the $V_HH$ peptide monomers have binding specificity for epitopes of TcdA and two of the $V_HH$ peptide monomers have binding specificity for epitopes of TcdB.

4. The binding agent of claim 1, wherein the $V_HH$ peptide monomers independently have binding specificity for an epitope in the glucosyltransferase domain, cysteine protease domain, translocation domain or receptor binding domain of TcdA or TcdB.

5. The binding agent of claim 1, wherein the binding agent is a binding agent of (a).

6. A method of producing a binding agent comprising culturing an isolated host cell comprising an expression vector comprising an isolated polynucleotide sequence comprising a nucleotide sequence encoding a binding agent of claim 1 under conditions promoting expression of the binding agent, and recovering the binding agent from the cell culture.

7. The binding agent of claim 1, wherein the binding agent is a binding agent of (b).

8. A pharmaceutical formulation comprising a binding agent of any one of claims 1, 5 and 7 and a pharmaceutically acceptable carrier or diluent.

9. A method of treating or preventing a disease symptom induced by *C. difficile* in a subject comprising administering a therapeutically-effective amount of one or more binding agent of any one of claims 1, 5 and 7, or pharmaceutical formulation comprising the one or more binding agent and a pharmaceutically acceptable carrier or diluent, to a subject having *C. difficile* infection or a risk of developing *C. difficile* infection.

10. A method of neutralizing *C. difficile* toxin TcdA and/or TcdB in a subject infected by *C. difficile* comprising administering a therapeutically-effective amount of one or more binding agent of any one of claims 1, 5 and 7, or pharmaceutical formulation comprising the one or more binding agent and a pharmaceutically acceptable carrier or diluent, to a subject having *C. difficile* infection.

11. A method of treating or preventing *C. difficile* disease in a subject comprising administering a therapeutically-effective amount of one or more binding agent of any one of claims 1, 5 and 7, or pharmaceutical formulation comprising the one or more binding agent and a pharmaceutically acceptable carrier or diluent, to a subject having *C. difficile* infection or a risk of developing *C. difficile* infection.

12. The method of claim 10, where the neutralizing is partial or full neutralization.

* * * * *

SEQUENCE LISTING

```
<160> NUMBER OF SEQ ID NOS: 67

<210> SEQ ID NO 1
<211> LENGTH: 127
<212> TYPE: PRT
<213> ORGANISM: Artificial Sequence
<220> FEATURE:
<223> OTHER INFORMATION: Codon-optimized VHH peptide monomer 5D

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser
        115                 120                 125

<210> SEQ ID NO 2
<211> LENGTH: 381
<212> TYPE: DNA
<213> ORGANISM: Artificial Sequence
<220> FEATURE:
<223> OTHER INFORMATION: Codon-optimized VHH peptide monomer 5D

<400> SEQUENCE: 2
caggtgcaac tggttgaatc tgggggaggc ttggtacaac tgggggatc  cctgagactc        60 tcttgcgagg cctccggatt caccttggac tactatggca tcggctggtt ccgccagccc       120
ccagggaagg agcgggaggc cgtttcatac attagtgcca gtgcccggac catactgtac       180
gcagactctg tgaagggacg ctttaccatc tctaggaca atgccaaaaa tgctgtgtac        240
ctgcaaatga acagcctcaa gcgggaggat accgcagtgt actactgcgc gagacggcgc       300
ttctccgctt ctagcgtgaa tagatggctg gccgacgact acgacgtgtg gggacggggc       360
acacaggtgg ctgtctcgag c                                                381

<210> SEQ ID NO 3
<211> LENGTH: 111
<212> TYPE: PRT
<213> ORGANISM: Artificial Sequence
<220> FEATURE:
<223> OTHER INFORMATION: Codon-optimized VHH peptide monomer E3

<400> SEQUENCE: 3
```

Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
            20                  25                  30

Thr Val Thr Trp Ser Arg Gln Ala Pro Gly Lys Ser Leu Gln Trp Val
            35                  40                  45

Ala Ser Met Thr Lys Thr Asn Asn Glu Ile Tyr Ser Asp Ser Val Lys
        50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser
            100                 105                 110

<210> SEQ ID NO 4
<211> LENGTH: 333
<212> TYPE: DNA
<213> ORGANISM: Artificial Sequence
<220> FEATURE:
<223> OTHER INFORMATION: Codon-optimized VHH peptide monomer E3

<400> SEQUENCE: 4
caagttcagc tggtcgaatc cggggggcgga ctggtccaga caggggggctc cctgaggctc    60 tcctgtgcat cttccggaag catcgccggc ttcgagaccg tgacctggtc tcgccaggct   120
cccgggaagt ctctgcagtg gtcgcttcc atgactaaga ctaacaacga gatctactct   180
gactcagtga aaggccgctt catcatttct agagataacg ctaaaaacac agtgtatctg   240
cagatgaata gtctcaaacc tgaagacaca ggcgtgtatt tctgtaaggg tcctgagctg   300
aggggccagg gcatccaggt aacagtctcg agt                                333

<210> SEQ ID NO 5
<211> LENGTH: 121
<212> TYPE: PRT
<213> ORGANISM: Artificial Sequence
<220> FEATURE:
<223> OTHER INFORMATION: Codon-optimized VHH peptide monomer AA6

<400> SEQUENCE: 5

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
            35                  40                  45

Ala Thr Ile Asn Thr Asp Gly Ser Thr Met Arg Asp Asp Ser Thr Lys
        50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser
            115                 120

```
<210> SEQ ID NO 6
<211> LENGTH: 363
<212> TYPE: DNA
<213> ORGANISM: Artificial Sequence
<220> FEATURE:
<223> OTHER INFORMATION: Codon-optimized VHH peptide monomer AA6

<400> SEQUENCE: 6
caactgcagc tggtagagac aggggggcggc ttagttcagc ctggagggtc tctcagactg      60
tcatgcgctg cctctggctt taccttcagt gactacgtga tgacatgggt ccgccaagct     120
ccagggaagg ggcctgagtg gatcgctact attaatacag atggcagcac aatgcgggac     180
gactccacaa aggggcggtt caccatttcc agagacaacg ccaagaatac tctgtaccct     240
cagatgacca gtctgaaacc cgaggacact gctctgtact attgtgcaag aggccgggtg     300
atctctgctt ccgctatcag aggcgcagta aggggccctg aacacaagt aactgtctcg     360 agc                                                                   363

<210> SEQ ID NO 7
<211> LENGTH: 126
<212> TYPE: PRT
<213> ORGANISM: Artificial Sequence
<220> FEATURE:
<223> OTHER INFORMATION: Codon-optimized VHH peptide monomer AH3

<400> SEQUENCE: 7

Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
            20                  25                  30

Ile Gly Trp Phe Arg Gln Ala Pro Gly Lys Glu Arg Glu Gly Val Ser
        35                  40                  45

Cys Ile Ser Ser Ser Gly Asp Ser Thr Lys Tyr Ala Asp Ser Val Lys
    50                  55                  60

Gly Arg Phe Thr Thr Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Ala Phe Arg Ala Thr Met Cys Gly Val Phe Pro Leu Ser Pro Tyr Gly
            100                 105                 110

Lys Asp Asp Trp Gly Lys Gly Thr Leu Val Thr Val Ser Ser
        115                 120                 125

<210> SEQ ID NO 8
<211> LENGTH: 378
<212> TYPE: DNA
<213> ORGANISM: Artificial Sequence
<220> FEATURE:
<223> OTHER INFORMATION: Codon-optimized VHH peptide monomer AH3

<400> SEQUENCE: 8
caggtacagc tggtggagac ggggggggctg gtacaaccag cgggtcact gaggctttcc      60 tgtgccgcat ctgggttcac actggattat tcgtccatag ggtggtttcg gcaggctcct     120
ggcaaagagc gtgagggggt ctcatgtatt agtagtagtg gtgatagcac aaagtacgcc     180
gattccgtaa agggccggtt tacaacctcc aggataatg ctaagaacac cgtatatctc      240
cagatgaact ctctgaagcc cgacgatacg gccgtatatt actgtgcggc tttcagggcg     300
actatgtgcg gcgtgttccc tctgagccct acggcaagg acgactgggg caaggggacc     360
```

-continued ctggtgaccg tctcgagt                                                     378

<210> SEQ ID NO 9
<211> LENGTH: 15
<212> TYPE: PRT
<213> ORGANISM: Artificial Sequence
<220> FEATURE:
<223> OTHER INFORMATION: Codon-optimized flexible linker 1

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 45
<212> TYPE: DNA
<213> ORGANISM: Artificial Sequence
<220> FEATURE:
<223> OTHER INFORMATION: Codon-optimized flexible linker 1

<400> SEQUENCE: 10
ggcggtggag ggtctggtgg gggaggctca ggggtggag gcagc                         45

<210> SEQ ID NO 11
<211> LENGTH: 16
<212> TYPE: PRT
<213> ORGANISM: Artificial Sequence
<220> FEATURE:
<223> OTHER INFORMATION: Codon-optimized flexible linker 2

<400> SEQUENCE: 11

Gly Gly Gly Ser Gly Gly Gly Ser Gly Gly Gly Ser Gly Gly Gly Ser
1               5                   10                  15

<210> SEQ ID NO 12
<211> LENGTH: 48
<212> TYPE: DNA
<213> ORGANISM: Artificial Sequence
<220> FEATURE:
<223> OTHER INFORMATION: Codon-optimized flexible linker 2

<400> SEQUENCE: 12
ggtggcggaa gcggaggggg cagcgggggt gggagcggtg ggggcagc                    48

<210> SEQ ID NO 13
<211> LENGTH: 15
<212> TYPE: PRT
<213> ORGANISM: Artificial Sequence
<220> FEATURE:
<223> OTHER INFORMATION: Codon-optimized flexible linker 3

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 45
<212> TYPE: DNA
<213> ORGANISM: Artificial Sequence
<220> FEATURE:
<223> OTHER INFORMATION: Codon-optimized flexible linker 3

<400> SEQUENCE: 14
gggggaggcg gttcaggcgg tgggggatct ggcggggtg gatcc                        45

<210> SEQ ID NO 15

-continued

<211> LENGTH: 269
<212> TYPE: PRT
<213> ORGANISM: Artificial Sequence
<220> FEATURE:
<223> OTHER INFORMATION: AH3-5D heterodimer

<400> SEQUENCE: 15

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Gly Gly Gly Ser Gly Gly Gly Ser Gly Gly Gly Ser Gln Val
    130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
        195                 200                 205

Arg Phe Thr Ile Ser Arg Asp Asn Ala Lys Asn Ala Val Tyr Leu Gln
    210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser
            260                 265

<210> SEQ ID NO 16
<211> LENGTH: 807
<212> TYPE: DNA
<213> ORGANISM: Artificial Sequence
<220> FEATURE:
<223> OTHER INFORMATION: AH3-5D heterodimer

<400> SEQUENCE: 16
caggtacagc tggtggagac ggggggaggg ctggtacaac caggcgggtc actgaggctt     60
tcctgtgccg catctgggtt cacactggat tattcgtcca tagggtggtt tcggcaggct    120
cctggcaaag agcgtgaggg ggtctcatgt attagtagta gtggtgatag cacaaagtac    180
gccgattccg taaagggccg gtttacaacc tccagggata tgctaagaac accgtatat    240 ctccagatga actctctgaa gcccgacgat acggccgtat attactgtgc ggctttcagg    300

```
gcgactatgt gcggcgtgtt ccctctgagc ccttacggca aggacgactg gggcaagggg      360
accctggtga ccgtatcctc aggcggtgga gggtctggtg ggggaggctc agggggtgga      420
ggcagccagg tgcaactggt tgaatctggg ggaggcttgg tacaacctgg gggatccctg      480
agactctctt gcgaggcctc cggattcacc ttggactact atggcatcgg ctggttccgc      540
cagcccccag ggaaggagcg ggaggccgtt tcatacatta gtgccagtgc ccggaccata      600
ctgtacgcag actctgtgaa gggacgcttt accatctcta gggacaatgc caaaaatgct      660
gtgtacctgc aaatgaacag cctcaagcgg gaggataccg cagtgtacta ctgcgcgaga      720
cggcgcttct ccgcttctag cgtgaataga tggctggccg acgactacga cgtgtgggga      780
cggggcacac aggtggctgt ctcgagc                                          807
```

<210> SEQ ID NO 17
<211> LENGTH: 247
<212> TYPE: PRT
<213> ORGANISM: Artificial Sequence
<220> FEATURE:
<223> OTHER INFORMATION: AA6-E3 heterodimer

<400> SEQUENCE: 17

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Gly Gly Gly Ser Gly Gly
        115                 120                 125

Gly Gly Ser Gly Gly Gly Gly Ser Gln Val Gln Leu Val Glu Ser Gly
    130                 135                 140

Gly Leu Val Gln Thr Gly Gly Ser Leu Arg Leu Ser Cys Ala Ser
145                 150                 155                 160

Ser Gly Ser Ile Ala Gly Phe Glu Thr Val Thr Trp Ser Arg Gln Ala
                165                 170                 175

Pro Gly Lys Ser Leu Gln Trp Val Ala Ser Met Thr Lys Thr Asn Asn
            180                 185                 190

Glu Ile Tyr Ser Asp Ser Val Lys Gly Arg Phe Ile Ile Ser Arg Asp
        195                 200                 205

Asn Ala Lys Asn Thr Val Tyr Leu Gln Met Asn Ser Leu Lys Pro Glu
    210                 215                 220

Asp Thr Gly Val Tyr Phe Cys Lys Gly Pro Glu Leu Arg Gly Gln Gly
225                 230                 235                 240

Ile Gln Val Thr Val Ser Ser
                245
```

<210> SEQ ID NO 18
<211> LENGTH: 741

```
<212> TYPE: DNA
<213> ORGANISM: Artificial Sequence
<220> FEATURE:
<223> OTHER INFORMATION: AA6-E3 heterodimer

<400> SEQUENCE: 18
caactgcagc tggtagagac aggggggcggc ttagttcagc ctggagggtc tctcagactg    60
tcatgcgctg cctctggctt taccttcagt gactacgtga tgacatgggt ccgccaagct   120
ccagggaagg ggcctgagtg gatcgctact attaatacag atggcagcac aatgcgggac   180
gactccacaa aggggcggtt caccatttcc agagacaacg ccaagaatac tctgtacctt   240
cagatgacca gtctgaaacc cgaggacact gctctgtact attgtgcaag aggccgggtg   300
atctctgctt ccgctatcag aggcgcagta aggggccctg aacacaggt aaccgtttca   360
tccgggggag gcggttcagg cggtggggga tctggcgggg gtggatccca agttcagctg   420
gtcgaatccg ggggcggact ggtccagaca ggggctccc tgaggctctc ctgtgcatct   480
tccgaagca tcgccggctt cgagaccgtg acctggtctc gccaggctcc cgggaagtct   540
ctgcagtggg tcgcttccat gactaagact aacaacgaga tctactctga ctcagtgaaa   600
ggccgcttca tcatttctag agataacgct aaaaacacag tgtatctgca gatgaatagt   660
ctcaaacctg aagacacagg cgtgtatttc tgtaagggtc ctgagctgag gggccagggc   720
atccaggtaa cagtctcgag t                                              741

<210> SEQ ID NO 19
<211> LENGTH: 532
<212> TYPE: PRT
<213> ORGANISM: Artificial Sequence
<220> FEATURE:
<223> OTHER INFORMATION: ABAB binding agent

<400> SEQUENCE: 19

Gln Val Gln Leu Val Glu Thr Gly Gly Gly Leu Val Gln Pro Gly Gly
1               5                   10                  15
Ser Leu Arg Leu Ser Cys Ala Ala Ser Gly Phe Thr Leu Asp Tyr Ser
            20                  25                  30
Ser Ile Gly Trp Phe Arg Gln Ala Pro Gly Lys Glu Arg Glu Gly Val
        35                  40                  45
Ser Cys Ile Ser Ser Ser Gly Asp Ser Thr Lys Tyr Ala Asp Ser Val
    50                  55                  60
Lys Gly Arg Phe Thr Thr Ser Arg Asp Asn Ala Lys Asn Thr Val Tyr
65                  70                  75                  80
Leu Gln Met Asn Ser Leu Lys Pro Asp Asp Thr Ala Val Tyr Tyr Cys
                85                  90                  95
Ala Ala Phe Arg Ala Thr Met Cys Gly Val Phe Pro Leu Ser Pro Tyr
            100                 105                 110
Gly Lys Asp Asp Trp Gly Lys Gly Thr Leu Val Thr Val Ser Ser Gly
        115                 120                 125
Gly Gly Gly Ser Gly Gly Gly Ser Gly Gly Gly Ser Gln Val
    130                 135                 140
Gln Leu Val Glu Ser Gly Gly Gly Leu Val Gln Pro Gly Gly Ser Leu
145                 150                 155                 160
Arg Leu Ser Cys Glu Ala Ser Gly Phe Thr Leu Asp Tyr Tyr Gly Ile
                165                 170                 175
Gly Trp Phe Arg Gln Pro Pro Gly Lys Glu Arg Glu Ala Val Ser Tyr
            180                 185                 190
```

```
Ile Ser Ala Ser Ala Arg Thr Ile Leu Tyr Ala Asp Ser Val Lys Gly
            195                 200                 205

Arg Phe Thr Ile Ser Arg Asp Asn Ala Lys Asn Ala Val Tyr Leu Gln
    210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser Gly Gly Gly
            260                 265                 270

Ser Gly Gly Gly Ser Gly Gly Gly Ser Gly Gly Gly Ser Gln Leu Gln
        275                 280                 285

Leu Val Glu Thr Gly Gly Gly Leu Val Gln Pro Gly Gly Ser Leu Arg
    290                 295                 300

Leu Ser Cys Ala Ala Ser Gly Phe Thr Phe Ser Asp Tyr Val Met Thr
305                 310                 315                 320

Trp Val Arg Gln Ala Pro Gly Lys Gly Pro Glu Trp Ile Ala Thr Ile
                325                 330                 335

Asn Thr Asp Gly Ser Thr Met Arg Asp Asp Ser Thr Lys Gly Arg Phe
            340                 345                 350

Thr Ile Ser Arg Asp Asn Ala Lys Asn Thr Leu Tyr Leu Gln Met Thr
        355                 360                 365

Ser Leu Lys Pro Glu Asp Thr Ala Leu Tyr Tyr Cys Ala Arg Gly Arg
    370                 375                 380

Val Ile Ser Ala Ser Ala Ile Arg Gly Ala Val Arg Gly Pro Gly Thr
385                 390                 395                 400

Gln Val Thr Val Ser Ser Gly Gly Gly Ser Gly Gly Gly Gly Gly Ser
                405                 410                 415

Gly Gly Gly Gly Ser Gln Val Gln Leu Val Glu Ser Gly Gly Gly Leu
            420                 425                 430

Val Gln Thr Gly Gly Ser Leu Arg Leu Ser Cys Ala Ser Ser Gly Ser
        435                 440                 445

Ile Ala Gly Phe Glu Thr Val Thr Trp Ser Arg Gln Ala Pro Gly Lys
    450                 455                 460

Ser Leu Gln Trp Val Ala Ser Met Thr Lys Thr Asn Asn Glu Ile Tyr
465                 470                 475                 480

Ser Asp Ser Val Lys Gly Arg Phe Ile Ile Ser Arg Asp Asn Ala Lys
                485                 490                 495

Asn Thr Val Tyr Leu Gln Met Asn Ser Leu Lys Pro Glu Asp Thr Gly
            500                 505                 510

Val Tyr Phe Cys Lys Gly Pro Glu Leu Arg Gly Gln Gly Ile Gln Val
        515                 520                 525

Thr Val Ser Ser
    530

<210> SEQ ID NO 20
<211> LENGTH: 1596
<212> TYPE: DNA
<213> ORGANISM: Artificial Sequence
<220> FEATURE:
<223> OTHER INFORMATION: ABAB binding agent

<400> SEQUENCE: 20
caggtacagc tggtggagac ggggggaggg ctggtacaac caggcgggtc actgaggctt      60
tcctgtgccg catctgggtt cacactggat tattcgtcca tagggtggtt tcggcaggct     120
```

```
cctggcaaag agcgtgaggg ggtctcatgt attagtagta gtggtgatag cacaaagtac      180
gccgattccg taaagggccg gtttacaacc tccaggcata atgctaagaa caccgtatat      240
ctccagatga actctctgaa gcccgacgat acggccgtat attactgtgc ggctttcagg      300
gcgactatgt gcggcgtgtt ccctctgagc ccttacggca aggacgactg gggcaagggg      360
accctggtga ccgtatcctc aggcggtgga gggtctggtg ggggaggctc agggggtgga      420
ggcagccagg tgcaactggt tgaatctggg ggaggcttgg tacaacctgg gggatccctg      480
agactctctt gcgaggcctc cggattcacc ttggactact atggcatcgg ctggttccgc      540
cagcccccag ggaaggagcg ggaggccgtt tcatacatta gtccagtgc ccggaccata      600
ctgtacgcag actctgtgaa gggacgcttt accatctcta ggacaatgc caaaaatgct      660
gtgtacctgc aaatgaacag cctcaagcgg aggataccg cagtgtacta ctgcgcgaga      720
cggcgcttct ccgcttctag cgtgaataga tggctggccg acgactacga cgtgtgggga      780
cggggcacac aggtggctgt gtcttccggt ggcggaagcg gaggggggcag cggggggtggg      840
agcggtgggg gcagccaact gcagctggta gagacagggg gcggcttagt tcagcctgga      900
gggtctctca gactgtcatg cgctgcctct ggctttacct tcagtgacta cgtgatgaca      960
tgggtccgcc aagctccagg gaaggggcct gagtggatcg ctactattaa tacagatggc     1020
agcacaatgc gggacgactc cacaaagggg cggttcacca tttccagaga caacgccaag     1080
aatactctgt accttcagat gaccagtctg aaacccgagg acactgctct gtactattgt     1140
gcaagaggcc gggtgatctc tgcttccgct atcagaggcg cagtaagggg ccctggaaca     1200
caggtaaccg tttcatccgg gggaggcggt tcaggcggtg ggggatctgg cggggtgga     1260
tcccaagttc agctggtcga atccggggc ggactggtcc agacaggggg ctccctgagg     1320
ctctcctgtg catcttccgg aagcatcgcc ggcttcgaga ccgtgacctg gtctcgccag     1380
gctcccggga gtctctgca gtgggtcgct ccatgacta agactaacaa cgagatctac     1440
tctgactcag tgaaaggccg cttcatcatt tctagagata cgctaaaaaa cacagtgtat     1500
ctgcagatga atagtctcaa acctgaagac acaggcgtgt atttctgtaa gggtcctgag     1560
ctgagggggcc agggcatcca ggtaacagtc tcgagt                              1596
```

<210> SEQ ID NO 21
<211> LENGTH: 12
<212> TYPE: PRT
<213> ORGANISM: Artificial Sequence
<220> FEATURE:
<223> OTHER INFORMATION: Albumin-binding peptide

<400> SEQUENCE: 21

Asp Ile Cys Leu Pro Arg Trp Gly Cys Leu Trp Asp
1               5                   10

<210> SEQ ID NO 22
<211> LENGTH: 761
<212> TYPE: PRT
<213> ORGANISM: Artificial Sequence
<220> FEATURE:
<223> OTHER INFORMATION: ABAB-Fc binding agent

<400> SEQUENCE: 22

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
                20                  25                  30

```
Ser Ile Gly Trp Phe Arg Gln Ala Pro Gly Lys Glu Arg Glu Gly Val
         35                  40                  45

Ser Cys Ile Ser Ser Ser Gly Asp Ser Thr Lys Tyr Ala Asp Ser Val
     50                  55                  60

Lys Gly Arg Phe Thr Thr Ser Arg Asp Asn Ala Lys Asn Thr Val Tyr
 65                  70                  75                  80

Leu Gln Met Asn Ser Leu Lys Pro Asp Asp Thr Ala Val Tyr Tyr Cys
                 85                  90                  95

Ala Ala Phe Arg Ala Thr Met Cys Gly Val Phe Pro Leu Ser Pro Tyr
                100                 105                 110

Gly Lys Asp Asp Trp Gly Lys Gly Thr Leu Val Thr Val Ser Ser Gly
            115                 120                 125

Gly Gly Gly Ser Gly Gly Gly Ser Gly Gly Gly Ser Gln Val
        130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
            195                 200                 205

Arg Phe Thr Ile Ser Arg Asp Asn Ala Lys Asn Ala Val Tyr Leu Gln
        210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser Gly Gly Gly
            260                 265                 270

Ser Gly Gly Gly Ser Gly Gly Gly Ser Gly Gly Gly Ser Gln Leu Gln
        275                 280                 285

Leu Val Glu Thr Gly Gly Gly Leu Val Gln Pro Gly Gly Ser Leu Arg
        290                 295                 300

Leu Ser Cys Ala Ala Ser Gly Phe Thr Phe Ser Asp Tyr Val Met Thr
305                 310                 315                 320

Trp Val Arg Gln Ala Pro Gly Lys Gly Pro Glu Trp Ile Ala Thr Ile
                325                 330                 335

Asn Thr Asp Gly Ser Thr Met Arg Asp Asp Ser Thr Lys Gly Arg Phe
            340                 345                 350

Thr Ile Ser Arg Asp Asn Ala Lys Asn Thr Leu Tyr Leu Gln Met Thr
        355                 360                 365

Ser Leu Lys Pro Glu Asp Thr Ala Leu Tyr Tyr Cys Ala Arg Gly Arg
        370                 375                 380

Val Ile Ser Ala Ser Ala Ile Arg Gly Ala Val Arg Gly Pro Gly Thr
385                 390                 395                 400

Gln Val Thr Val Ser Ser Gly Gly Gly Ser Gly Gly Gly Ser
                405                 410                 415

Gly Gly Gly Gly Ser Gln Val Gln Leu Val Glu Ser Gly Gly Gly Leu
            420                 425                 430

Val Gln Thr Gly Gly Ser Leu Arg Leu Ser Cys Ala Ser Ser Gly Ser
        435                 440                 445
```

| | | | | | | | | | | | | | | |
|---|---|---|---|---|---|---|---|---|---|---|---|---|---|---|
|Ile|Ala|Gly|Phe|Glu|Thr|Val|Thr|Trp|Ser|Arg|Gln|Ala|Pro|Gly|Lys
| |450| | | | |455| | | |460| | | | |

Ser Leu Gln Trp Val Ala Ser Met Thr Lys Thr Asn Asn Glu Ile Tyr
465                 470                 475                 480

Ser Asp Ser Val Lys Gly Arg Phe Ile Ile Ser Arg Asp Asn Ala Lys
                485                 490                 495

Asn Thr Val Tyr Leu Gln Met Asn Ser Leu Lys Pro Glu Asp Thr Gly
            500                 505                 510

Val Tyr Phe Cys Lys Gly Pro Glu Leu Arg Gly Gln Gly Ile Gln Val
            515                 520                 525

Thr Val Ser Ser Gly Ser Asp Lys Thr His Thr Cys Pro Pro Cys Pro
530                 535                 540

Ala Pro Glu Leu Leu Gly Gly Pro Ser Val Phe Leu Phe Pro Pro Lys
545                 550                 555                 560

Pro Lys Asp Thr Leu Met Ile Ser Arg Thr Pro Glu Val Thr Cys Val
                565                 570                 575

Val Val Asp Val Ser His Glu Asp Pro Glu Val Lys Phe Asn Trp Tyr
            580                 585                 590

Val Asp Gly Val Glu Val His Asn Ala Lys Thr Lys Pro Arg Glu Glu
            595                 600                 605

Gln Tyr Asn Ser Thr Tyr Arg Val Val Ser Val Leu Thr Val Leu His
610                 615                 620

Gln Asp Trp Leu Asn Gly Lys Glu Tyr Lys Cys Lys Val Ser Asn Lys
625                 630                 635                 640

Ala Leu Pro Ala Pro Ile Glu Lys Thr Ile Ser Lys Ala Lys Gly Gln
                645                 650                 655

Pro Arg Glu Pro Gln Val Tyr Thr Leu Pro Pro Ser Arg Glu Glu Met
            660                 665                 670

Thr Lys Asn Gln Val Ser Leu Thr Cys Leu Val Lys Gly Phe Tyr Pro
            675                 680                 685

Ser Asp Ile Ala Val Glu Trp Glu Ser Asn Gly Gln Pro Glu Asn Asn
690                 695                 700

Tyr Lys Thr Thr Pro Pro Val Leu Asp Ser Asp Gly Ser Phe Phe Leu
705                 710                 715                 720

Tyr Ser Lys Leu Thr Val Asp Lys Ser Arg Trp Gln Gln Gly Asn Val
                725                 730                 735

Phe Ser Cys Ser Val Met His Glu Ala Leu His Asn His Tyr Thr Gln
            740                 745                 750

Lys Ser Leu Ser Leu Ser Pro Gly Lys
            755                 760

```
<210> SEQ ID NO 23
<211> LENGTH: 2286
<212> TYPE: DNA
<213> ORGANISM: Artificial Sequence
<220> FEATURE:
<223> OTHER INFORMATION: ABAB-Fc binding agent

<400> SEQUENCE: 23
caggtacagc tggtggagac gggggagggg ctggtacaac caggcggtc actgaggctt      60 tcctgtgccg catctgggtt cacactggat tattcgtcca tagggtggtt tcggcaggct    120
cctggcaaag agcgtgaggg ggtctcatgt attagtagta gtggtgatag cacaaagtac    180
gccgattccg taaagggccg gtttacaacc tccaggggata atgctaagaa caccgtatat    240
ctccagatga actctctgaa gcccgacgat acggccgtat attactgtgc ggctttcagg    300
```

```
gcgactatgt gcggcgtgtt ccctctgagc ccttacggca aggacgactg gggcaagggg    360
accctggtga ccgtatcctc aggcggtgga gggtctggtg ggggaggctc agggggtgga    420
ggcagccagg tgcaactggt tgaatctggg ggaggcttgg tacaacctgg gggatccctg    480
agactctctt gcgaggcctc cggattcacc ttggactact atggcatcgg ctggttccgc    540
cagcccccag ggaaggagcg ggaggccgtt tcatacatta gtgccagtgc ccggaccata    600
ctgtacgcag actctgtgaa gggacgcttt accatctcta gggacaatgc caaaaatgct    660
gtgtacctgc aaatgaacag cctcaagcgg aggataccg cagtgtacta ctgcgcgaga    720
cggcgcttct ccgcttctag cgtgaataga tggctggccg acgactacga cgtgtgggga    780
cggggcacac aggtggctgt gtcttccggt ggcggaagcg gagggggcag cgggggtggg    840
agcggtgggg gcagccaact gcagctggta gagacagggg gcggcttagt tcagcctgga    900
gggtctctca gactgtcatg cgctgcctct ggctttacct tcagtgacta cgtgatgaca    960
tgggtccgcc aagctccagg gaaggggcct gagtggatcg ctactattaa tacagatggc    1020
agcacaatgc gggacgactc cacaaagggg cggttcacca tttccagaga caacgccaag    1080
aatactctgt accttcagat gaccagtctg aaacccgagg acactgctct gtactattgt    1140
gcaagaggcc gggtgatctc tgcttccgct atcagaggcg cagtaagggg ccctggaaca    1200
caggtaaccg tttcatccgg gggaggcggt tcaggcggtg ggggatctgg cggggggtgga    1260 tcccaagttc agctggtcga atccgggggc ggactggtcc agacagggg ctccctgagg    1320 ctctcctgtg catcttccgg aagcatcgcc ggcttcgaga ccgtgacctg gtctcgccag    1380
gctcccggga gtctctgca gtgggtcgct tccatgacta agactaacaa cgagatctac    1440
tctgactcag tgaaaggccg cttcatcatt tctagagata cgctaaaaa cacagtgtat    1500 ctgcagatga atagtctcaa acctgaagac acaggcgtgt atttctgtaa gggtcctgag    1560
ctgaggggcc agggcatcca ggtaacagtc tcgagcggat ccgacaaaac tcacacatgc    1620
ccaccgtgcc cagcacctga actcctgggg ggaccgtcag tcttcctctt ccccccaaaa    1680
cccaaggaca cctcatgat ctcccggacc cctgaggtca catgcgtggt ggtggacgtg    1740
agccacgaag accctgaggt caagttcaac tggtacgtgg acggcgtgga ggtgcataat    1800
gccaagacaa agccgcggga ggagcagtac aacagcacgt accgtgtggt cagcgtcctc    1860
accgtcctgc accaggactg gctgaatggc aaggagtaca agtgcaaggt ctccaacaaa    1920
gccctcccag cccccatcga gaaaaccatc tccaaagcca agggcagccc cgagaaccca    1980
caggtgtaca ccctgccccc atcccgggag gagatgacca agaaccaggt cagcctgacc    2040
tgcctggtca aaggcttcta tcccagcgac atcgccgtgg agtgggagag caatgggcag    2100
ccggagaaca actacaagac cacgcctccc gtgctggact ccgacggctc cttcttcctc    2160
tatagcaagc tcaccgtgga caagagcagg tggcagcagg ggaacgtctt ctcatgctcc    2220
gtgatgcatg aggctctgca caaccactac acgcagaaga gcctctccct gtctccgggt    2280
aaatga                                                              2286
```

<210> SEQ ID NO 24
<211> LENGTH: 356
<212> TYPE: PRT
<213> ORGANISM: Artificial Sequence
<220> FEATURE:
<223> OTHER INFORMATION: 5D-Fc binding agent

<400> SEQUENCE: 24

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
                100                 105                 110

Asp Tyr Asp Val Trp Gly Arg Gly Thr Gln Val Ala Val Ser Ser Gly
            115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 25
<211> LENGTH: 1071
<212> TYPE: DNA
<213> ORGANISM: Artificial Sequence
<220> FEATURE:
<223> OTHER INFORMATION: 5D-Fc binding agent

<400> SEQUENCE: 25

```
caggtgcaac tggttgaatc tggggggaggc ttggtacaac ctgggggatc cctgagactc      60
tcttgcgagg cctccggatt caccttggac tactatggca tcggctggtt ccgccagccc     120
ccagggaagg agcgggaggc cgtttcatac attagtgcca gtgcccggac catactgtac     180
gcagactctg tgaagggacg ctttaccatc tctagggaca atgccaaaaa tgctgtgtac     240
ctgcaaatga acagcctcaa gcgggaggat accgcagtgt actactgcgc gagacggcgc     300
ttctccgctt ctagcgtgaa tagatggctg gccgacgact acgacgtgtg gggacggggc     360
acacaggtgg ctgtctcgag cggatccgac aaaactcaca catgcccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
aagaccacgc ctcccgtgct ggactccgac ggctccttct tcctctatag caagctcacc     960
gtggacaaga gcaggtggca gcaggggaac gtcttctcat gctccgtgat gcatgaggct    1020
ctgcacaacc actacacgca gaagagcctc tccctgtctc cgggtaaatg a             1071
```

<210> SEQ ID NO 26
<211> LENGTH: 340
<212> TYPE: PRT
<213> ORGANISM: Artificial Sequence
<220> FEATURE:
<223> OTHER INFORMATION: E3-Fc binding agent

<400> SEQUENCE: 26

```
Gln Val Gln Leu Val Glu Ser Gly Gly Gly Leu Val Gln Thr Gly Gly
1               5                   10                  15

Ser Leu Arg Leu Ser Cys Ala Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser Gly
            100                 105                 110

Ser Asp Lys Thr His Thr Cys Pro Pro Cys Pro Ala Pro Glu Leu Leu
        115                 120                 125

Gly Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175
```

```
Val His Asn Ala Lys Thr Lys Pro Arg Glu Glu Gln Tyr Asn Ser Thr
            180                 185                 190
Tyr Arg Val Val Ser Val Leu Thr Val Leu His Gln Asp Trp Leu Asn
        195                 200                 205
Gly Lys Glu Tyr Lys Cys Lys Val Ser Asn Lys Ala Leu Pro Ala Pro
    210                 215                 220
Ile Glu Lys Thr Ile Ser Lys Ala Lys Gly Gln Pro Arg Glu Pro Gln
225                 230                 235                 240
Val Tyr Thr Leu Pro Pro Ser Arg Glu Glu Met Thr Lys Asn Gln Val
                245                 250                 255
Ser Leu Thr Cys Leu Val Lys Gly Phe Tyr Pro Ser Asp Ile Ala Val
            260                 265                 270
Glu Trp Glu Ser Asn Gly Gln Pro Glu Asn Asn Tyr Lys Thr Thr Pro
        275                 280                 285
Pro Val Leu Asp Ser Asp Gly Ser Phe Phe Leu Tyr Ser Lys Leu Thr
    290                 295                 300
Val Asp Lys Ser Arg Trp Gln Gln Gly Asn Val Phe Ser Cys Ser Val
305                 310                 315                 320
Met His Glu Ala Leu His Asn His Tyr Thr Gln Lys Ser Leu Ser Leu
                325                 330                 335
Ser Pro Gly Lys
            340

<210> SEQ ID NO 27
<211> LENGTH: 1023
<212> TYPE: DNA
<213> ORGANISM: Artificial Sequence
<220> FEATURE:
<223> OTHER INFORMATION: E3-Fc binding agent

<400> SEQUENCE: 27
caagttcagc tggtcgaatc cggggggcgga ctggtccaga caggggggctc cctgaggctc         60
tcctgtgcat cttccggaag catcgccggc ttcgagaccg tgacctggtc tcgccaggct        120
cccgggaagt ctctgcagtg gtcgcttcc atgactaaga ctaacaacga gatctactct        180
gactcagtga aaggccgctt catcatttct agagataacg ctaaaaacac agtgtatctg        240
cagatgaata gtctcaaacc tgaagacaca ggcgtgtatt tctgtaaggg tcctgagctg        300
agggggccagg gcatccaggt aacagtctcg agcggatccg acaaaactca cacatgccca        360
ccgtgcccag cacctgaact cctgggggga ccgtcagtct tcctcttccc cccaaaaccc        420
aaggacaccc tcatgatctc ccggacccct gaggtcacat gcgtggtggt ggacgtgagc        480
cacgaagacc ctgaggtcaa gttcaactgg tacgtggacg gcgtggaggt gcataatgcc        540
aagacaaagc cgcgggagga gcagtacaac agcacgtacc gtgtggtcag cgtcctcacc        600
gtcctgcacc aggactggct gaatggcaag gagtacaagt gcaaggtctc caacaaagcc        660
ctcccagccc ccatcgagaa aaccatctcc aaagccaaag gcagccccg agaaccacag        720
gtgtacaccc tgcccccatc ccgggaggag atgaccaaga accaggtcag cctgacctgc        780
ctggtcaaag gcttctatcc cagcgacatc gccgtggagt gggagagcaa tgggcagccg        840
gagaacaact acaagaccac gcctcccgtg ctggactccg acggctcctt cttcctctat        900
agcaagctca ccgtggacaa gagcaggtgg cagcagggga acgtcttctc atgctccgtg        960
atgcatgagg ctctgcacaa ccactacacg cagaagagcc tctccctgtc tccgggtaaa       1020
tga                                                                     1023
```

<210> SEQ ID NO 28
<211> LENGTH: 350
<212> TYPE: PRT
<213> ORGANISM: Artificial Sequence
<220> FEATURE:
<223> OTHER INFORMATION: AA6-Fc binding agent

<400> SEQUENCE: 28

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Gly Ser Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350
```

<210> SEQ ID NO 29
<211> LENGTH: 1053

<212> TYPE: DNA
<213> ORGANISM: Artificial Sequence
<220> FEATURE:
<223> OTHER INFORMATION: AA6-Fc binding agent

<400> SEQUENCE: 29

```
caactgcagc tggtagagac aggggcggc ttagttcagc ctggagggtc tctcagactg      60
tcatgcgctg cctctggctt taccttcagt gactacgtga tgacatgggt ccgccaagct    120
ccagggaagg ggcctgagtg gatcgctact attaatacag atggcagcac aatgcgggac    180
gactccacaa aggggcggtt caccatttcc agagacaacg ccaagaatac tctgtacctt    240
cagatgacca gtctgaaacc cgaggacact gctctgtact attgtgcaag aggccgggtg    300
atctctgctt ccgctatcag aggcgcagta aggggccctg aacacaagt aactgtctcg    360
agcggatccg acaaaactca cacatgccca ccgtgcccag cacctgaact cctgggggga    420
ccgtcagtct tcctcttccc cccaaaaccc aaggacaccc tcatgatctc ccggacccct    480
gaggtcacat gcgtggtggt ggacgtgagc acgaagacc ctgaggtcaa gttcaactgg    540
tacgtggacg gcgtggaggt gcataatgcc aagacaaagc cgcgggagga gcagtacaac    600
agcacgtacc gtgtggtcag cgtcctcacc gtcctgcacc aggactggct gaatggcaag    660
gagtacaagt gcaaggtctc caacaaagcc ctcccagccc ccatcgagaa aaccatctcc    720
aaagccaaag gcagccccg agaaccacag gtgtacaccc tgcccccatc ccgggaggag    780
atgaccaaga accaggtcag cctgacctgc ctggtcaaag gcttctatcc cagcgacatc    840
gccgtggagt gggagagcaa tgggcagccg gagaacaact acaagaccac gcctcccgtg    900
ctggactccg acggctcctt cttcctctat agcaagctca ccgtggacaa gagcaggtgg    960
cagcagggga acgtcttctc atgctccgtg atgcatgagg ctctgcacaa ccactacacg   1020
cagaagagcc tctccctgtc tccgggtaaa tga                                1053
```

<210> SEQ ID NO 30
<211> LENGTH: 356
<212> TYPE: PRT
<213> ORGANISM: Artificial Sequence
<220> FEATURE:
<223> OTHER INFORMATION: AH3-Fc binding agent

<400> SEQUENCE: 30

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Pro Leu Ser Pro Tyr
            100                 105                 110

Gly Lys Asp Asp Trp Gly Lys Gly Thr Leu Val Thr Val Ser Ser Gly
        115                 120                 125

Ser Asp Lys Thr His Thr Cys Pro Pro Cys Pro Ala Pro Glu Leu Leu
    130                 135                 140
```

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 31
<211> LENGTH: 1071
<212> TYPE: DNA
<213> ORGANISM: Artificial Sequence
<220> FEATURE:
<223> OTHER INFORMATION: AH3-Fc binding agent

<400> SEQUENCE: 31
caggtacagc tggtggagac ggggggaggg ctggtacaac aggcgggtc actgaggctt      60 tcctgtgccg catctgggtt cacactggat tattcgtcca tagggtggtt tcggcaggct     120
cctggcaaag agcgtgaggg gtctcatgt attagtagta gtggtgatag cacaaagtac      180
gccgattccg taaagggccg gtttacaacc tccagggata atgctaagaa caccgtatat     240
ctccagatga actctctgaa gcccgacgat acggccgtat attactgtgc ggctttcagg     300
gcgactatgt gcggcgtgtt ccctctgagc ccttacggca aggacgactg gggcaagggg     360
accctggtga ccgtctcgag cggatccgac aaaactcaca catgcccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780

| | | |
|---|---|---|
| cccccatccc gggaggagat gaccaagaac caggtcagcc tgacctgcct ggtcaaaggc | 840 |
| ttctatccca gcgacatcgc cgtggagtgg gagagcaatg ggcagccgga gaacaactac | 900 |
| aagaccacgc ctcccgtgct ggactccgac ggctccttct tcctctatag caagctcacc | 960 |
| gtggacaaga gcaggtggca gcaggggaac gtcttctcat gctccgtgat gcatgaggct | 1020 |
| ctgcacaacc actacacgca gaagagcctc tccctgtctc cgggtaaatg a | 1071 |

<210> SEQ ID NO 32
<211> LENGTH: 498
<212> TYPE: PRT
<213> ORGANISM: Artificial Sequence
<220> FEATURE:
<223> OTHER INFORMATION: AH3-5D-Fc binding agent

<400> SEQUENCE: 32

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Gly Gly Gly Ser Gly Gly Gly Ser Gly Gly Gly Ser Gln Val
    130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
        195                 200                 205

Arg Phe Thr Ile Ser Arg Asp Asn Ala Lys Asn Ala Val Tyr Leu Gln
    210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser Gly Ser Asp
            260                 265                 270

Lys Thr His Thr Cys Pro Pro Cys Pro Ala Pro Glu Leu Leu Gly Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320
```

```
Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys

<210> SEQ ID NO 33
<211> LENGTH: 1497
<212> TYPE: DNA
<213> ORGANISM: Artificial Sequence
<220> FEATURE:
<223> OTHER INFORMATION: AH3-5D-Fc binding agent

<400> SEQUENCE: 33
caggtacagc tggtggagac ggggggaggg ctggtacaac aggcgggtc actgaggctt      60
tcctgtgccg catctgggtt cacactggat tattcgtcca tagggtggtt tcggcaggct     120
cctggcaaag agcgtgaggg ggtctcatgt attagtagta gtggtgatag cacaaagtac     180
gccgattccg taaagggccg gtttacaacc tccagggata tgctaagaa caccgtatat      240
ctccagatga actctctgaa gcccgacgat acggccgtat attactgtgc ggctttcagg     300
gcgactatgt gcggcgtgtt ccctctgagc ccttacggca aggacgactg ggcaagggg      360
accctggtga ccgtatcctc aggcggtgga gggtctggtg ggggaggctc aggggggtgga   420
ggcagccagg tgcaactggt tgaatctggg ggaggcttgg tacaacctgg gggatccctg     480
agactctctt gcgaggcctc cggattcacc ttggactact atggcatcgg ctggttccgc     540
cagcccccag ggaaggagcg ggaggccgtt tcatacatta gtgccagtgc ccggaccata     600
ctgtacgcag actctgtgaa gggacgcttt accatctcta gggacaatgc caaaaatgct     660
gtgtacctgc aaatgaacag cctcaagcgg aggataccg cagtgtacta ctgcgcgaga     720
cggcgcttct ccgcttctag cgtgaataga tggctggccg acgactacga cgtgtgggga    780
cggggcacac aggtggctgt ctcgagcgga tccgacaaaa ctcacacatg cccaccgtgc     840
ccagcacctg aactcctggg gggaccgtca gtcttcctct tccccccaaa acccaaggac     900
accctcatga tctcccggac ccctgaggtc acatgcgtgg tggtggacgt gagccacgaa     960
gaccctgagg tcaagttcaa ctggtacgtg gacggcgtgg aggtgcataa tgccaagaca    1020
```

```
aagccgcggg aggagcagta acaacagcacg taccgtgtgg tcagcgtcct caccgtcctg    1080
caccaggact ggctgaatgg caaggagtac aagtgcaagg tctccaacaa agccctccca    1140
gcccccatcg agaaaaccat ctccaaagcc aaagggcagc cccgagaacc acaggtgtac    1200
accctgcccc catcccggga ggagatgacc aagaaccagg tcagcctgac ctgcctggtc    1260
aaaggcttct atcccagcga catcgccgtg gagtgggaga gcaatgggca gccggagaac    1320
aactacaaga ccacgcctcc cgtgctggac tccgacggct ccttcttcct ctatagcaag    1380
ctcaccgtgg acaagagcag gtggcagcag gggaacgtct tctcatgctc cgtgatgcat    1440
gaggctctgc acaaccacta cacgcagaag agcctctccc tgtctccggg taaatga      1497
```

<210> SEQ ID NO 34
<211> LENGTH: 476
<212> TYPE: PRT
<213> ORGANISM: Artificial Sequence
<220> FEATURE:
<223> OTHER INFORMATION: AA6-E3-Fc binding agent

<400> SEQUENCE: 34

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Gly Gly Gly Ser Gly Gly
        115                 120                 125

Gly Gly Ser Gly Gly Gly Ser Gln Val Gln Leu Val Glu Ser Gly
    130                 135                 140

Gly Gly Leu Val Gln Thr Gly Gly Ser Leu Arg Leu Ser Cys Ala Ser
145                 150                 155                 160

Ser Gly Ser Ile Ala Gly Phe Glu Thr Val Thr Trp Ser Arg Gln Ala
                165                 170                 175

Pro Gly Lys Ser Leu Gln Trp Val Ala Ser Met Thr Lys Thr Asn Asn
            180                 185                 190

Glu Ile Tyr Ser Asp Ser Val Lys Gly Arg Phe Ile Ile Ser Arg Asp
        195                 200                 205

Asn Ala Lys Asn Thr Val Tyr Leu Gln Met Asn Ser Leu Lys Pro Glu
    210                 215                 220

Asp Thr Gly Val Tyr Phe Cys Lys Gly Pro Glu Leu Arg Gly Gln Gly
225                 230                 235                 240

Ile Gln Val Thr Val Ser Ser Gly Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
```

```
                    275                 280                 285
Thr Cys Val Val Val Asp Val Ser His Glu Asp Pro Glu Val Lys Phe
                290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                325                 330                 335
Val Leu His Gln Asp Trp Leu Asn Gly Lys Glu Tyr Lys Cys Lys Val
                340                 345                 350
Ser Asn Lys Ala Leu Pro Ala Pro Ile Glu Lys Thr Ile Ser Lys Ala
                355                 360                 365
Lys Gly Gln Pro Arg Glu Pro Gln Val Tyr Thr Leu Pro Pro Ser Arg
                370                 375                 380
Glu Glu Met Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                405                 410                 415
Glu Asn Asn Tyr Lys Thr Thr Pro Pro Val Leu Asp Ser Asp Gly Ser
                420                 425                 430
Phe Phe Leu Tyr Ser Lys Leu Thr Val Asp Lys Ser Arg Trp Gln Gln
                435                 440                 445
Gly Asn Val Phe Ser Cys Ser Val Met His Glu Ala Leu His Asn His
450                 455                 460
Tyr Thr Gln Lys Ser Leu Ser Leu Ser Pro Gly Lys
465                 470                 475

<210> SEQ ID NO 35
<211> LENGTH: 1431
<212> TYPE: DNA
<213> ORGANISM: Artificial Sequence
<220> FEATURE:
<223> OTHER INFORMATION: AA6-E3-Fc binding agent

<400> SEQUENCE: 35
caactgcagc tggtagagac agggggcggc ttagttcagc ctggagggtc tctcagactg      60
tcatgcgctg cctctggctt taccttcagt gactacgtga tgcatgggt ccgccaagct     120 ccagggaagg ggcctgagtg gatcgctact attaatacag atggcagcac aatgcgggac     180
gactccacaa aggggcggtt caccatttcc agagacaacg ccaagaatac tctgtacctt     240
cagatgacca gtctgaaacc cgaggacact gctctgtact attgtgcaag aggccgggtg     300
atctctgctt ccgctatcag aggcgcagta aggggccctg aacacaggt aaccgtttca     360 tccgggggag cgggttcagg cggtgggga tctggcgggg gtggatccca agttcagctg     420
gtcgaatccg ggggcggact ggtccagaca gggggctccc tgaggctctc ctgtgcatct     480
tccggaagca tcgccggctt cgagaccgtg acctggtctc gccaggctcc cgggaagtct     540
ctgcagtggg tcgcttccat gactaagact aacaacgaga tctactctga ctcagtgaaa     600
ggccgcttca tcatttctag agataacgct aaaaacacag tgtatctgca gatgaatagt     660
ctcaaacctg aagacacagg cgtgtatttc tgtaagggtc tgagctgag gggcagggc      720 atccaggtaa cagtctcgag cggatccgac aaaactcaca catgcccacc gtgcccagca     780
cctgaactcc tggggggacc gtcagtcttc ctcttccccc caaaacccaa ggacaccctc     840
atgatctccc ggacccctga ggtcacatgc gtggtggtgg acgtgagcca cgaagaccct     900
gaggtcaagt tcaactggta cgtggacggc gtggaggtgc ataatgccaa gacaaagccg     960
```

-continued

```
cgggaggagc agtacaacag cacgtaccgt gtggtcagcg tcctcaccgt cctgcaccag    1020
gactggctga atggcaagga gtacaagtgc aaggtctcca acaaagccct cccagccccc    1080
atcgagaaaa ccatctccaa agccaaaggg cagccccgag aaccacaggt gtacaccctg    1140
cccccatccc gggaggagat gaccaagaac caggtcagcc tgacctgcct ggtcaaaggc    1200
ttctatccca gcgacatcgc cgtggagtgg gagagcaatg ggcagccgga gaacaactac    1260
aagaccacgc ctcccgtgct ggactccgac ggctccttct tcctctatag caagctcacc    1320
gtggacaaga gcaggtggca gcaggggaac gtcttctcat gctccgtgat gcatgaggct    1380
ctgcacaacc actacacgca gaagagcctc tccctgtctc cgggtaaatg a             1431
```

<210> SEQ ID NO 36
<211> LENGTH: 457
<212> TYPE: PRT
<213> ORGANISM: Artificial Sequence
<220> FEATURE:
<223> OTHER INFORMATION: AH3-IgG1-heavy chain

<400> SEQUENCE: 36

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
```

```
                        275                 280                 285
Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                        325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                    405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 37
<211> LENGTH: 1374
<212> TYPE: DNA
<213> ORGANISM: Artificial Sequence
<220> FEATURE:
<223> OTHER INFORMATION: AH3-IgG1-heavy chain

<400> SEQUENCE: 37
caggtacagc tggtggagac ggggggaggg ctggtacaac caggcgggtc actgaggctt      60
tcctgtgccg catctgggtt cacactggat tattcgtcca tagggtggtt tcggcaggct     120
cctggcaaag agcgtgaggg gtctcatgt attagtagta gtggtgatag cacaaagtac      180
gccgattccg taaagggccg gtttacaacc tccagggata atgctaagaa caccgtatat     240
ctccagatga actctctgaa gcccgacgat acggccgtat attactgtgc ggctttcagg     300
gcgactatgt gcggcgtgtt ccctctgagc ccttacggca aggacgactg gggcaagggg     360
accctggtga ccgtctcgag tgcgtcgacc aagggcccat cggtcttccc gctagcaccc     420
tcctccaaga gcacctctgg gggcacagcg gccctgggct gcctggtcaa ggactacttc     480
cccgaacctg tgacggtctc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga gagttgagcc caaatcttgt gacaaaactc acacatgccc accgtgccca     720
gcacctgaac tcctgggggg accgtcagtc ttcctcttcc cccaaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccagcc    1020
```

```
cccatcgaga aaaccatctc caaagccaaa gggcagcccc gagaaccaca ggtgtacacc    1080
ctgcccccat cccgggagga gatgaccaag aaccaggtca gcctgacctg cctggtcaaa    1140
ggcttctatc ccagcgacat cgccgtggag tgggagagca atgggcagcc ggagaacaac    1200
tacaagacca cgcctcccgt gctggactcc gacggctcct tcttcctcta tagcaagctc    1260
accgtggaca agagcaggtg gcagcagggg aacgtcttct catgctccgt gatgcatgag    1320
gctctgcaca accactacac gcagaagagc ctctccctgt ccccgggtaa atga          1374
```

```
<210> SEQ ID NO 38
<211> LENGTH: 457
<212> TYPE: PRT
<213> ORGANISM: Artificial Sequence
<220> FEATURE:
<223> OTHER INFORMATION: 5D-IgG1-heavy chain

<400> SEQUENCE: 38

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300
```

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Glu Glu Met
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
450                 455

<210> SEQ ID NO 39
<211> LENGTH: 1374
<212> TYPE: DNA
<213> ORGANISM: Artificial Sequence
<220> FEATURE:
<223> OTHER INFORMATION: 5D-IgG1-heavy chain

<400> SEQUENCE: 39
caggtgcaac tggttgaatc tggggggaggc ttggtacaac tgggggatc cctgagactc     60 tcttgcgagg cctccggatt caccttggac tactatggca tcggctggtt ccgccagccc    120
ccagggaaga gcggggaggc cgtttcatac attagtgcca gtgcccggac catactgtac    180
gcagactctg tgaagggacg ctttaccatc tctagggaca tgccaaaaa tgctgtgtac    240 ctgcaaatga acagcctcaa gcgggaggat accgcagtgt actactgcgc gagacggcgc    300
ttctccgctt ctagcgtgaa tagatggctg gccgacgact acgacgtgtg ggacggggc    360 acacaggtgg ctgtctcgag cgcgtcgacc aagggcccat cggtcttccc gctagcaccc    420
tcctccaaga gcacctctgg gggcacagcg gccctgggct gcctggtcaa ggactacttc    480
cccgaacctg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga gagttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggagga gatgaccaag aaccaggtca gcctgacctg cctggtcaaa   1140
ggcttctatc ccagcgacat cgccgtggag tgggagagca tgggcagcc ggagaacaac   1200

| | | | | |
|---|---|---|---|---|
| tacaagacca | cgcctcccgt | gctggactcc | gacggctcct | tcttcctcta tagcaagctc | 1260 |
| accgtggaca | agagcaggtg | gcagcagggg | aacgtcttct | catgctccgt gatgcatgag | 1320 |
| gctctgcaca | accactacac | gcagaagagc | ctctccctgt | ccccgggtaa atga | 1374 |

```
<210> SEQ ID NO 40
<211> LENGTH: 228
<212> TYPE: PRT
<213> ORGANISM: Artificial Sequence
<220> FEATURE:
<223> OTHER INFORMATION: AA6-IgG1-kappa chain

<400> SEQUENCE: 40

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys
225

<210> SEQ ID NO 41
<211> LENGTH: 687
<212> TYPE: DNA
<213> ORGANISM: Artificial Sequence
<220> FEATURE:
<223> OTHER INFORMATION: AA6-IgG1-kappa chain

<400> SEQUENCE: 41
```

| | | | | |
|---|---|---|---|---|
| caactgcagc | tggtagagac | aggggggcggc | ttagttcagc | ctggagggtc tctcagactg | 60 |
| tcatgcgctg | cctctggctt | taccttcagt | gactacgtga | tgacatgggt ccgccaagct | 120 |
| ccagggaagg | ggcctgagtg | gatcgctact | attaatacag | atggcagcac aatgcgggac | 180 |
| gactccacaa | aggggcggtt | caccatttcc | agagacaacg | ccaagaatac tctgtaccct | 240 |

-continued

```
cagatgacca gtctgaaacc cgaggacact gctctgtact attgtgcaag aggccgggtg    300
atctctgctt ccgctatcag aggcgcagta aggggccctg aacacaagt aactgtctcg    360 agccgtacgg tggctgcacc atctgtcttc atcttcccgc catctgatga gcagttgaaa    420
tctggaactg cctctgttgt gtgcctgctg aataacttct atcccagaga ggccaaagta    480
cagtggaagg tggataacgc cctccaatcg ggtaactccc aggagagtgt cacagagcag    540
gacagcaagg acagcaccta cagcctcagc agcaccctga cgctgagcaa agcagactac    600
gagaaacaca agtctacgc ctgcgaagtc acccatcagg gcctgagctc gcccgtcaca    660
aagagcttca cagggggaga gtgttga                                        687
```

<210> SEQ ID NO 42
<211> LENGTH: 218
<212> TYPE: PRT
<213> ORGANISM: Artificial Sequence
<220> FEATURE:
<223> OTHER INFORMATION: E3-IgG1-kappa chain

<400> SEQUENCE: 42

```
Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 43
<211> LENGTH: 657
<212> TYPE: DNA
<213> ORGANISM: Artificial Sequence
<220> FEATURE:
<223> OTHER INFORMATION: E3-IgG1-kappa chain

<400> SEQUENCE: 43

-continued

```
caagttcagc tggtcgaatc cggggcgga ctggtccaga caggggctc cctgaggctc      60
tcctgtgcat cttccggaag catcgccggc ttcgagaccg tgacctggtc tcgccaggct   120
cccgggaagt ctctgcagtg ggtcgcttcc atgactaaga ctaacaacga gatctactct   180
gactcagtga aaggccgctt catcatttct agagataacg ctaaaaacac agtgtatctg   240
cagatgaata gtctcaaacc tgaagacaca ggcgtgtatt tctgtaaggg tcctgagctg   300
aggggccagg gcatccaggt aacagtctcg agccgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca cagggagga gtgttga      657
```

<210> SEQ ID NO 44
<211> LENGTH: 599
<212> TYPE: PRT
<213> ORGANISM: Artificial Sequence
<220> FEATURE:
<223> OTHER INFORMATION: AH3-5D-IgG1 heavy chain

<400> SEQUENCE: 44

```
Gln Val Gln Leu Val Glu Thr Gly Gly Gly Leu Val Gln Pro Gly Gly
  1               5                  10                  15

Ser Leu Arg Leu Ser Cys Ala Ala Ser Gly Phe Thr Leu Asp Tyr Ser
             20                  25                  30

Ser Ile Gly Trp Phe Arg Gln Ala Pro Gly Lys Glu Arg Glu Gly Val
         35                  40                  45

Ser Cys Ile Ser Ser Gly Asp Ser Thr Lys Tyr Ala Asp Ser Val
     50                  55                  60

Lys Gly Arg Phe Thr Thr Ser Arg Asp Asn Ala Lys Asn Thr Val Tyr
 65                  70                  75                  80

Leu Gln Met Asn Ser Leu Lys Pro Asp Asp Thr Ala Val Tyr Tyr Cys
                 85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Gly Gly Gly Ser Gly Gly Gly Ser Gly Gly Gly Ser Gln Val
    130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
        195                 200                 205

Arg Phe Thr Ile Ser Arg Asp Asn Ala Lys Asn Ala Val Tyr Leu Gln
    210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255
```

Asp Val Trp Gly Arg Gly Thr Gln Val Ala Val Ser Ser Ala Ser Thr
            260                 265                 270

Lys Gly Pro Ser Val Phe Pro Leu Ala Pro Ser Ser Lys Ser Thr Ser
        275                 280                 285

Gly Gly Thr Ala Ala Leu Gly Cys Leu Val Lys Asp Tyr Phe Pro Glu
    290                 295                 300

Pro Val Thr Val Ser Trp Asn Ser Gly Ala Leu Thr Ser Gly Val His
305                 310                 315                 320

Thr Phe Pro Ala Val Leu Gln Ser Ser Gly Leu Tyr Ser Leu Ser Ser
                325                 330                 335

Val Val Thr Val Pro Ser Ser Ser Leu Gly Thr Gln Thr Tyr Ile Cys
            340                 345                 350

Asn Val Asn His Lys Pro Ser Asn Thr Lys Val Asp Lys Arg Val Glu
        355                 360                 365

Pro Lys Ser Cys Asp Lys Thr His Thr Cys Pro Pro Cys Pro Ala Pro
    370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
            420                 425                 430

Gly Val Glu Val His Asn Ala Lys Thr Lys Pro Arg Glu Glu Gln Tyr
        435                 440                 445

Asn Ser Thr Tyr Arg Val Val Ser Val Leu Thr Val Leu His Gln Asp
    450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Glu Glu Met Thr Lys
            500                 505                 510

Asn Gln Val Ser Leu Thr Cys Leu Val Lys Gly Phe Tyr Pro Ser Asp
        515                 520                 525

Ile Ala Val Glu Trp Glu Ser Asn Gly Gln Pro Glu Asn Asn Tyr Lys
    530                 535                 540

Thr Thr Pro Pro Val Leu Asp Ser Asp Gly Ser Phe Phe Leu Tyr Ser
545                 550                 555                 560

Lys Leu Thr Val Asp Lys Ser Arg Trp Gln Gln Gly Asn Val Phe Ser
                565                 570                 575

Cys Ser Val Met His Glu Ala Leu His Asn His Tyr Thr Gln Lys Ser
            580                 585                 590

Leu Ser Leu Ser Pro Gly Lys
        595

<210> SEQ ID NO 45
<211> LENGTH: 1800
<212> TYPE: DNA
<213> ORGANISM: Artificial Sequence
<220> FEATURE:
<223> OTHER INFORMATION: AH3-5D-IgG1 heavy chain

<400> SEQUENCE: 45
caggtacagc tggtggagac gggggggaggg ctggtacaac caggcgggtc actgaggctt        60

| | | |
|---|---|---|
| tcctgtgccg catctgggtt cacactggat tattcgtcca tagggtggtt tcggcaggct | 120 | |
| cctggcaaag agcgtgaggg ggtctcatgt attagtagta gtggtgatag cacaaagtac | 180 | |
| gccgattccg taaagggccg gtttacaacc tccagggata atgctaagaa caccgtatat | 240 | |
| ctccagatga actctctgaa gcccgacgat acggccgtat attactgtgc ggctttcagg | 300 | |
| gcgactatgt gcggcgtgtt ccctctgagc ccttacggca aggacgactg gggcaagggg | 360 | |
| accctggtga ccgtatcctc aggcggtgga gggtctggtg ggggaggctc aggggggtgga | 420 | |
| ggcagccagg tgcaactggt tgaatctggg ggaggcttgg tacaacctgg gggatccctg | 480 | |
| agactctctt gcgaggcctc cggattcacc ttggactact atggcatcgg ctggttccgc | 540 | |
| cagcccccag ggaaggagcg ggaggccgtt tcatacatta gtgccagtgc ccggaccata | 600 | |
| ctgtacgcag actctgtgaa gggacgcttt accatctcta gggacaatgc caaaaatgct | 660 | |
| gtgtacctgc aaatgaacag cctcaagcgg aggataccga gtgtacta ctgcgcgaga | 720 | |
| cggcgcttct ccgcttctag cgtgaataga tggctggccg acgactacga cgtgtgggga | 780 | |
| cggggcacac aggtggctgt ctcgagcgcg tcgaccaagg gcccatcggt cttcccgcta | 840 | |
| gcaccctcct ccaagagcac ctctgggggc acagcggccc tgggctgcct ggtcaaggac | 900 | |
| tacttccccg aacctgtgac ggtctcgtgg aactcaggcg ccctgaccag cggcgtgcac | 960 | |
| accttcccgg ctgtcctaca gtcctcagga ctctactccc tcagcagcgt ggtgaccgtg | 1020 | |
| ccctccagca gcttgggcac ccagacctac atctgcaacg tgaatcacaa gcccagcaac | 1080 | |
| accaaggtgg acaagagagt tgagcccaaa tcttgtgaca aaactcacac atgcccaccg | 1140 | |
| tgcccagcac ctgaactcct ggggggaccg tcagtcttcc tcttcccccc aaaacccaag | 1200 | |
| gacaccctca tgatctcccg gacccctgag gtcacatgcg tggtggtgga cgtgagccac | 1260 | |
| gaagaccctg aggtcaagtt caactggtac gtggacggcg tggaggtgca taatgccaag | 1320 | |
| acaaagccgc gggaggagca gtacaacagc acgtaccgtg tggtcagcgt cctcaccgtc | 1380 | |
| ctgcaccagg actggctgaa tggcaaggag tacaagtgca aggtctccaa caaagccctc | 1440 | |
| ccagccccca tcgagaaaac catctccaaa gccaagggc agccccgaga accacaggtg | 1500 | |
| tacaccctgc ccccatcccg ggaggagatg accaagaacc aggtcagcct gacctgcctg | 1560 | |
| gtcaaaggct tctatcccag cgacatcgcc gtggagtggg agagcaatgg gcagccggag | 1620 | |
| aacaactaca agaccacgcc tcccgtgctg gactccgacg gctccttctt cctctatagc | 1680 | |
| aagctcaccg tggacaagag caggtggcag caggggaacg tcttctcatg ctccgtgatg | 1740 | |
| catgaggctc tgcacaacca ctacacgcag aagagcctct ccctgtcccc gggtaaatga | 1800 | |

<210> SEQ ID NO 46
<211> LENGTH: 354
<212> TYPE: PRT
<213> ORGANISM: Artificial Sequence
<220> FEATURE:
<223> OTHER INFORMATION: AA6-E3-IgG1 light chain

<400> SEQUENCE: 46

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
            85                  90                  95

Arg Gly Arg Val Ile Ser Ala Ser Ala Ile Arg Gly Ala Val Arg Gly
        100                 105                 110

Pro Gly Thr Gln Val Thr Val Ser Ser Gly Gly Gly Ser Gly Gly
        115                 120                 125

Gly Gly Ser Gly Gly Gly Ser Gln Val Gln Leu Val Glu Ser Gly
    130                 135                 140

Gly Gly Leu Val Gln Thr Gly Gly Ser Leu Arg Leu Ser Cys Ala Ser
145                 150                 155                 160

Ser Gly Ser Ile Ala Gly Phe Glu Thr Val Thr Trp Ser Arg Gln Ala
                165                 170                 175

Pro Gly Lys Ser Leu Gln Trp Val Ala Ser Met Thr Lys Thr Asn Asn
            180                 185                 190

Glu Ile Tyr Ser Asp Ser Val Lys Gly Arg Phe Ile Ile Ser Arg Asp
        195                 200                 205

Asn Ala Lys Asn Thr Val Tyr Leu Gln Met Asn Ser Leu Lys Pro Glu
210                 215                 220

Asp Thr Gly Val Tyr Phe Cys Lys Gly Pro Glu Leu Arg Gly Gln Gly
225                 230                 235                 240

Ile Gln Val Thr Val Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 47
<211> LENGTH: 1065
<212> TYPE: DNA
<213> ORGANISM: Artificial Sequence
<220> FEATURE:
<223> OTHER INFORMATION: AA6-E3-IgG1 light chain

<400> SEQUENCE: 47
caactgcagc tggtagagac aggggcggc ttagttcagc tggagggtc tctcagactg     60 tcatgcgctg cctctggctt taccttcagt gactacgtga tgacatgggt ccgccaagct    120
ccagggaagg ggcctgagtg gatcgctact attaatacag atggcagcac aatgcgggac    180
gactccacaa aggggcggtt caccatttcc agagacaacg ccaagaatac tctgtacctt    240
cagatgacca gtctgaaacc cgaggacact gctctgtact attgtgcaag aggccgggtg    300
atctctgctt ccgctatcag aggcgcagta aggggccctg gaacacaggt aaccgtttca    360

```
tccgggggag gcggttcagg cggtgggga tctggcgggg gtggatccca agttcagctg    420
gtcgaatccg ggggcggact ggtccagaca gggggctccc tgaggctctc ctgtgcatct    480
tccggaagca tcgccggctt cgagaccgtg acctggtctc gccaggctcc cgggaagtct    540
ctgcagtggg tcgcttccat gactaagact aacaacgaga tctactctga ctcagtgaaa    600
ggccgcttca tcatttctag agataacgct aaaaacacag tgtatctgca gatgaatagt    660
ctcaaacctg aagacacagg cgtgtatttc tgtaagggtc tgagctgag ggcagggc      720 atccaggtaa cagtctcgag ccgtacggtg gctgcaccat ctgtcttcat cttcccgcca    780
tctgatgagc agttgaaatc tggaactgcc tctgttgtgt gcctgctgaa taacttctat    840
cccagagagg ccaaagtaca gtggaaggtg ataacgccc tccaatcggg taactcccag    900
gagagtgtca cagagcagga cagcaaggac agcacctaca gcctcagcag cacccctgacg   960 ctgagcaaag cagactacga gaaacacaaa gtctacgcct gcgaagtcac ccatcagggc   1020
ctgagctcgc ccgtcacaaa gagcttcaac aggggagagt gttga                   1065
```

<210> SEQ ID NO 48
<211> LENGTH: 127
<212> TYPE: PRT
<213> ORGANISM: Artificial Sequence
<220> FEATURE:
<223> OTHER INFORMATION: VHH peptide monomer 5D

<400> SEQUENCE: 48

```
Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser
        115                 120                 125
```

<210> SEQ ID NO 49
<211> LENGTH: 381
<212> TYPE: DNA
<213> ORGANISM: Artificial Sequence
<220> FEATURE:
<223> OTHER INFORMATION: VHH peptide monomer 5D

<400> SEQUENCE: 49

```
caggtgcagc tcgtggagtc aggtggaggc ttggtgcagc tgggggggtc tctgagactc     60
tcctgtgaag cctctggatt cacttttgat tattatggta tagctggtt ccgccagccc    120 ccagggaagg agcgcgaggc ggtctcatat attagtgcca gtgcccgtac gatattgtat    180
gcagattccg tgaagggccg atttaccatc tccagagaca atgccaagaa cgcggtgtat    240
ctacaaatga acagcctgaa acgtgaggac acggctgtct attactgtgc gaggcggcga    300
ttctccgcgt ctagtgttaa tagatggctt gccgacgact atgacgtctg ggtcgggg     360
```

```
acccaggtcg cggtgtcctc a                                                    381
```

<210> SEQ ID NO 50
<211> LENGTH: 111
<212> TYPE: PRT
<213> ORGANISM: Artificial Sequence
<220> FEATURE:
<223> OTHER INFORMATION: VHH peptide monomer E3

<400> SEQUENCE: 50

```
Gln Val Gln Leu Val Glu Ser Gly Gly Gly Leu Val Gln Thr Gly Gly
1               5                   10                  15

Ser Leu Arg Leu Ser Cys Ala Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser
            100                 105                 110
```

<210> SEQ ID NO 51
<211> LENGTH: 333
<212> TYPE: DNA
<213> ORGANISM: Artificial Sequence
<220> FEATURE:
<223> OTHER INFORMATION: VHH peptide monomer E3

<400> SEQUENCE: 51

```
caggtgcagc tcgtggagtc gggcggaggc ttggtgcaga ctggggggtc tctgagactc      60
tcctgtgcat cctctggaag tatcgccggt ttcgaaaccg tgacctggtc ccgccaggct     120
cctggaaagt cgctccagtg gtcgcatcg atgactaaaa ctaataacga gatctattca     180
gactccgtga agggccgatt catcatctcc agagacaacg ccaagaatac ggtgtatcta     240
caaatgaaca gcctgaaacc tgaggacaca ggcgtctatt tttgtaaagg tcctgagttg     300 agggggccagg ggatccaggt caccgtctcc tcg                                  333
```

<210> SEQ ID NO 52
<211> LENGTH: 121
<212> TYPE: PRT
<213> ORGANISM: Artificial Sequence
<220> FEATURE:
<223> OTHER INFORMATION: VHH peptide monomer AA6

<400> SEQUENCE: 52

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
```

```
                65                  70                  75                  80
Gln Met Thr Ser Leu Lys Pro Glu Asp Thr Ala Leu Tyr Tyr Cys Ala
                    85                  90                  95

Arg Gly Arg Val Ile Ser Ala Ser Ala Ile Arg Gly Ala Val Arg Gly
                100                 105                 110

Pro Gly Thr Gln Val Thr Val Ser Ser
                115                 120

<210> SEQ ID NO 53
<211> LENGTH: 363
<212> TYPE: DNA
<213> ORGANISM: Artificial Sequence
<220> FEATURE:
<223> OTHER INFORMATION: VHH peptide monomer AA6

<400> SEQUENCE: 53
cagttgcagc tcgtggagac agggggaggc ttggtgcagc ctgggggtc tctgagactc      60 tcctgtgcag cctctggatt cacgttcagt gactacgtca tgacctgggt ccgccaggct    120
ccaggaaagg ggcccgaatg gatcgcaact attaatacgg acggtagcac gatgcgtgat    180
gactccacaa aaggccgatt caccatctcc agagacaacg ccaagaacac actgtatctg    240
caaatgacca gcctgaaacc ggaggacacg gccctgtatt actgtgcgag aggccgcgtg    300
atctccgcct ccgcgataag aggggcggtt aggggcccgg ggacccaggt caccgtctcc    360
tca                                                                  363

<210> SEQ ID NO 54
<211> LENGTH: 126
<212> TYPE: PRT
<213> ORGANISM: Artificial Sequence
<220> FEATURE:
<223> OTHER INFORMATION: VHH peptide monomer AH3

<400> SEQUENCE: 54

Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
                20                  25                  30

Ile Gly Trp Phe Arg Gln Ala Pro Gly Lys Glu Arg Glu Gly Val Ser
            35                  40                  45

Cys Ile Ser Ser Ser Gly Asp Ser Thr Lys Tyr Ala Asp Ser Val Lys
        50                  55                  60

Gly Arg Phe Thr Thr Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Ala Phe Arg Ala Thr Met Cys Gly Val Phe Pro Leu Ser Pro Tyr Gly
                100                 105                 110

Lys Asp Asp Trp Gly Lys Gly Thr Leu Val Thr Val Ser Ser
            115                 120                 125

<210> SEQ ID NO 55
<211> LENGTH: 378
<212> TYPE: DNA
<213> ORGANISM: Artificial Sequence
<220> FEATURE:
<223> OTHER INFORMATION: VHH peptide monomer AH3

<400> SEQUENCE: 55
```

```
caggtgcagc tcgtggagac gggggggcttg gtgcagcctg gggggtctct gagactctcc      60
tgtgcagcct ctggattcac tttggattat tcgtccatag ctggttccg ccaggccca        120 gggaaggagc gtgagggggt ctcatgtatt agtagtagtg gtgatagcac aaagtatgca     180
gactccgtga agggccgatt caccacctcc agagacaacg ccaagaacac ggtgtatctg     240
caaatgaaca gcctgaaacc tgacgacaca gccgtttatt actgtgcagc ttttagggcg     300
actatgtgcg gcgtgttccc ccttagcccc tacggcaagg acgactgggg caaagggacc     360
ctggtcaccg tctcctca                                                    378
```

<210> SEQ ID NO 56
<211> LENGTH: 15
<212> TYPE: PRT
<213> ORGANISM: Artificial Sequence
<220> FEATURE:
<223> OTHER INFORMATION: Flexible linker 1

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 45
<212> TYPE: DNA
<213> ORGANISM: Artificial Sequence
<220> FEATURE:
<223> OTHER INFORMATION: Flexible linker 1

<400> SEQUENCE: 57

```
ggcggtggtg gctctggtgg cggcggttcc ggtggcggtg gcagc                      45
```

<210> SEQ ID NO 58
<211> LENGTH: 15
<212> TYPE: PRT
<213> ORGANISM: Artificial Sequence
<220> FEATURE:
<223> OTHER INFORMATION: Flexible linker 2

<400> SEQUENCE: 58

Gly Gly Gly Gly Ser Gly Gly Gly Gly Ser Gly Gly Gly Gly Ser
1               5                   10                  15

<210> SEQ ID NO 59
<211> LENGTH: 45
<212> TYPE: DNA
<213> ORGANISM: Artificial Sequence
<220> FEATURE:
<223> OTHER INFORMATION: Flexible linker 2

<400> SEQUENCE: 59

```
ggtggaggcg gttcaggcgg aggtggctct ggcggtggcg gttcc                      45
```

<210> SEQ ID NO 60
<211> LENGTH: 15
<212> TYPE: PRT
<213> ORGANISM: Artificial Sequence
<220> FEATURE:
<223> OTHER INFORMATION: Flexible linker 3

<400> SEQUENCE: 60

Gly Gly Gly Gly Ser Gly Gly Gly Gly Ser Gly Gly Gly Gly Ser
1               5                   10                  15

<210> SEQ ID NO 61

```
<211> LENGTH: 45
<212> TYPE: DNA
<213> ORGANISM: Artificial Sequence
<220> FEATURE:
<223> OTHER INFORMATION: Flexible linker 3

<400> SEQUENCE: 61
ggcggtggtg gctctggtgg cggcggttcc ggtggcggtg gcagc         45

<210> SEQ ID NO 62
<211> LENGTH: 259
<212> TYPE: PRT
<213> ORGANISM: Artificial Sequence
<220> FEATURE:
<223> OTHER INFORMATION: 5D-E3 heterodimer

<400> SEQUENCE: 62
```

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Glu Thr Asn Ser Leu Lys Arg Glu Asp Thr Ala Val Tyr
                85                  90                  95

Tyr Cys Ala Arg Arg Phe Ser Ala Ser Ser Val Asn Arg Trp Leu
            100                 105                 110

Ala Asp Asp Tyr Asp Val Trp Gly Arg Gly Thr Gln Val Ala Val Ser
            115                 120                 125

Ser Gly Gly Gly Gly Ser Gly Gly Gly Gly Ser Gly Gly Gly Gly Ser
        130                 135                 140

Gln Val Gln Leu Val Glu Ser Gly Gly Gly Leu Val Gln Thr Gly Gly
145                 150                 155                 160

Ser Leu Arg Leu Ser Cys Ala Ser Ser Gly Ser Ile Ala Gly Phe Glu
                165                 170                 175

Thr Val Thr Trp Ser Arg Gln Ala Pro Gly Lys Ser Leu Gln Trp Val
            180                 185                 190

Ala Ser Met Glu Thr Thr Lys Thr Asn Asn Glu Ile Tyr Ser Asp Ser
        195                 200                 205

Val Lys Gly Arg Phe Ile Ile Ser Arg Asp Asn Ala Lys Asn Thr Val
    210                 215                 220

Tyr Leu Gln Met Glu Thr Asn Ser Leu Lys Pro Glu Asp Thr Gly Val
225                 230                 235                 240

Tyr Phe Cys Lys Gly Pro Glu Leu Arg Gly Gln Gly Ile Gln Val Thr
                245                 250                 255

Val Ser Ser

```
<210> SEQ ID NO 63
<211> LENGTH: 759
<212> TYPE: DNA
<213> ORGANISM: Artificial Sequence
<220> FEATURE:
<223> OTHER INFORMATION: 5D-E3 heterodimer

<400> SEQUENCE: 63
```

```
caggtgcagc tcgtggagtc aggtggaggc ttggtgcagc ctgggggtc tctgagactc    60
tcctgtgaag cctctggatt cactttggat tattatggta taggctggtt ccgccagccc   120
ccagggaagg agcgcgaggc ggtctcatat attagtgcca gtgcccgtac gatattgtat   180
gcagattccg tgaagggccg atttaccatc tccagagaca tgccaagaa cgcggtgtat   240
ctacaaatga acagcctgaa acgtgaggac acggctgtct attactgtgc gaggcggcga   300
ttctccgcgt ctagtgttaa tagatggctt gccgacgact atgacgtctg ggtcggggg   360
acccaggtcg cggtgtcctc aggcggtggt ggctctggtg gcggcggttc cggtggcggt   420
ggcagccagg tgcagctcgt ggagtcgggc ggaggcttgg tgcagactgg ggggtctctg   480
agactctcct gtgcatcctc tggaagtatc gccggtttcg aaaccgtgac ctggtcccgc   540
caggctcctg gaaagtcgct ccagtgggtc gcatcgatga ctaaaactaa taacgagatc   600
tattcagact ccgtgaaggg ccgattcatc atctccagag acaacgccaa gaatacggtg   660
tatctacaaa tgaacagcct gaaacctgag gacacaggcg tctattttg taaaggtcct   720
gagttgaggg gccaggggat ccaggtcacc gtctcctcg                          759
```

<210> SEQ ID NO 64
<211> LENGTH: 272
<212> TYPE: PRT
<213> ORGANISM: Artificial Sequence
<220> FEATURE:
<223> OTHER INFORMATION: AH3-AA6 heterodimer

<400> SEQUENCE: 64

```
Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
            20                  25                  30

Ile Gly Trp Phe Arg Gln Ala Pro Gly Lys Glu Arg Glu Gly Val Ser
        35                  40                  45

Cys Ile Ser Ser Ser Gly Asp Ser Thr Lys Tyr Ala Asp Ser Val Lys
    50                  55                  60

Gly Arg Phe Thr Thr Ser Arg Asp Asn Ala Lys Asn Thr Val Tyr Leu
65                  70                  75                  80

Gln Met Glu Thr Asn Ser Leu Lys Pro Asp Asp Thr Ala Val Tyr Tyr
                85                  90                  95

Cys Ala Ala Phe Arg Ala Thr Met Glu Thr Cys Gly Val Phe Pro Leu
            100                 105                 110

Ser Pro Tyr Gly Lys Asp Asp Trp Gly Lys Gly Thr Leu Val Thr Val
        115                 120                 125

Ser Ser Gly Gly Gly Gly Ser Gly Gly Gly Ser Gly Gly Gly Gly
    130                 135                 140

Ser Gln Leu Gln Leu Val Glu Thr Gly Gly Leu Val Gln Pro Gly
145                 150                 155                 160

Gly Ser Leu Arg Leu Ser Cys Ala Ala Ser Gly Phe Thr Phe Ser Asp
                165                 170                 175

Tyr Val Met Glu Thr Thr Trp Val Arg Gln Ala Pro Gly Lys Gly Pro
            180                 185                 190

Glu Trp Ile Ala Thr Ile Asn Thr Asp Gly Ser Thr Met Glu Thr Arg
        195                 200                 205

Asp Asp Ser Thr Lys Gly Arg Phe Thr Ile Ser Arg Asp Asn Ala Lys
    210                 215                 220
```

Asn Thr Leu Tyr Leu Gln Met Glu Thr Thr Ser Leu Lys Pro Glu Asp
225                 230                 235                 240

Thr Ala Leu Tyr Tyr Cys Ala Arg Gly Arg Val Ile Ser Ala Ser Ala
            245                 250                 255

Ile Arg Gly Ala Val Arg Gly Pro Gly Thr Gln Val Thr Val Ser Ser
        260                 265                 270

<210> SEQ ID NO 65
<211> LENGTH: 786
<212> TYPE: DNA
<213> ORGANISM: Artificial Sequence
<220> FEATURE:
<223> OTHER INFORMATION: AH3-AA6 heterodimer

<400> SEQUENCE: 65
caggtgcagc tcgtggagac gggggggcttg gtgcagcctg gggggtctct gagactctcc      60
tgtgcagcct ctggattcac tttggattat tcgtccatag gctggttccg ccaggcccca     120
gggaaggagc gtgaggggt ctcatgtatt agtagtagtg gtgatagcac aaagtatgca     180
gactccgtga agggccgatt caccacctcc agagacaacg ccaagaacac ggtgtatctg     240
caaatgaaca gcctgaaacc tgacgacaca gccgtttatt actgtgcagc ttttagggcg     300
actatgtgcg gcgtgttccc ccttagcccc tacggcaagg acgactgggg caaagggacc     360
ctggtcaccg tctcctcagg cggtggtggc tctggtggcg gcggttccgg tggcggtggc     420
agccagttgc agctcgtgga gacagggggga ggcttggtgc agcctggggg gtctctgaga     480
ctctcctgtg cagcctctgg attcacgttc agtgactacg tcatgacctg ggtccgccag     540
gctccaggaa agggggcccga atggatcgca actattaata cggacggtag cacgatgcgt     600
gatgactcca caaaggccg attcaccatc tccagagaca cgccaagaa cacactgtat     660 ctgcaaatga ccagcctgaa accggaggac acggccctgt attactgtgc gagaggccgc     720
gtgatctccg cctccgcgat aagagggcg gttagggccc cggggaccca ggtcaccgtc     780
tcctca                                                                 786

<210> SEQ ID NO 66
<211> LENGTH: 6
<212> TYPE: PRT
<213> ORGANISM: Artificial Sequence
<220> FEATURE:
<223> OTHER INFORMATION: six-histidine tag

<400> SEQUENCE: 66

His His His His His His
1               5

<210> SEQ ID NO 67
<211> LENGTH: 13
<212> TYPE: PRT
<213> ORGANISM: Artificial Sequence
<220> FEATURE:
<223> OTHER INFORMATION: E-tag for protein purification

<400> SEQUENCE: 67

Gly Ala Pro Val Pro Tyr Pro Asp Pro Leu Glu Pro Arg
1               5                   10